US008940488B2

(12) United States Patent
Aburatani et al.

(10) Patent No.: US 8,940,488 B2
(45) Date of Patent: Jan. 27, 2015

(54) CANCER DIAGNOSIS AND TREATMENT OF CANCER USING ANTI-ROBO 1 ANTIBODY

(75) Inventors: Hiroyuki Aburatani, Tokyo (JP);
Yoshitaka Hippo, Huntington, NY (US);
Akira Watanabe, Tokyo (JP); Masashi Fukayama, Tokyo (JP); Yukio Ito, Tokyo (JP); Masahiro Arai, Tokyo (JP);
Hirotaka Ito, Tokyo (JP); Toshihiko Ohtomo, Shizuoka (JP); Shin-ichi Funahshi, Shizuoka (JP); Yasuko Kinoshita, Kanagawa (JP)

(73) Assignees: Hiroyuki Aburatani, Tokyo (JP);
Perseus Proteomics Inc., Tokyo (JP);
Chugai Seiyaku Kabushiki Kaisha, Tokyo (JP)

( * ) Notice: Subject to any disclaimer, the term of this patent is extended or adjusted under 35 U.S.C. 154(b) by 59 days.

(21) Appl. No.: 11/547,534
(22) PCT Filed: Mar. 31, 2005
(86) PCT No.: PCT/JP2005/006838
§ 371 (c)(1),
(2), (4) Date: Apr. 13, 2007
(87) PCT Pub. No.: WO2005/095981
PCT Pub. Date: Oct. 13, 2005

(65) Prior Publication Data
US 2007/0212359 A1    Sep. 13, 2007

(30) Foreign Application Priority Data

Mar. 31, 2004  (JP) ................. 2004-102862
Aug. 4, 2004  (JP) ................. 2004-227899
Jan. 11, 2005  (JP) ................. 2005-004024

(51) Int. Cl.
G01N 33/53    (2006.01)
G01N 33/574   (2006.01)
G01N 33/576   (2006.01)

(52) U.S. Cl.
CPC ........ *G01N 33/57438* (2013.01); *G01N 33/576* (2013.01); *G01N 33/57415* (2013.01); *G01N 33/57419* (2013.01); *G01N 33/57423* (2013.01); *G01N 33/57446* (2013.01); *C07K 2317/732* (2013.01); *C07K 2317/734* (2013.01)
USPC ......................................... 435/7.1; 435/7.23

(58) Field of Classification Search
None
See application file for complete search history.

(56) References Cited

FOREIGN PATENT DOCUMENTS

| WO | WO 98/48051 | 10/1998 |
|---|---|---|
| WO | WO 99/20764 | 4/1999 |
| WO | WO 01/00828 | 1/2001 |
| WO | WO 01/46697 | 6/2001 |
| WO | WO 01/57207 | 8/2001 |
| WO | WO 01/92581 | 12/2001 |
| WO | WO 02/04514 | 1/2002 |
| WO | WO 02/14500 | 2/2002 |
| WO | 0229103 | 4/2002 ............... C12Q 1/68 |
| WO | WO 02/29103 | 4/2002 |
| WO | WO 03/029488 | 4/2003 |
| WO | 03/075860 | 9/2003 |

OTHER PUBLICATIONS

Boyd (The Basic Science of Oncology, 1992, McGraw-Hill, Inc., p. 379).*
Xian et al. (Proc. Natl. Acad. Sci. USA Dec. 2001 94: 15062-15066).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No:850).*
Kaiser (Science, 2006, 313: 1370).*
Benedict et al (J. Exp. Medicine, 2001, 193(1) 89-99).*
Jiang et al (JBC, 2003, 278(7) 4763-4769).*
Matsushita et al (FEBS Letters, 1999, vol. 443, pp. 348-352).*
Singh et al (Glycobiology, 2001, vol. 11, pp. 587-592).*
Tockman et al (Cancer Res., 1992, 52:2711s-2718s).*
NP_002932 (Mar. 19, 1999).*
NP_598334 (Mar. 26, 2002).*
Harlow and Lane (Antibodies: A Laboratory Manual, Cold Spring Harbor Laboratory N.Y. 1988, Ch. 14: 553-612).*
Harlow and Lane (Antibodies: A Laboratory Manual, 1988, p. 76).*
Prasad et al., Slit protein-mediated inhibition of CXCR4-induced chemotactic and chemoinvasive signaling pathways in breast cancer cells, : J Biol Chem. Mar. 5, 2004; 279(10): pp. 9115-9124.
Wang et al.,Induction of tumor angiogenesis by Slit-Robo signaling and inhibition of cancer growth by blocking Robo activity, Cancer Cell. Jul. 2003, 4(1): pp. 9-29.
Translation of the International Preliminary Report on Patentability dated Mar. 1, 2007 issued for corresponding International Patent Application No. PCT/JP2005/006838.
Office Action issued on Jul. 30, 2012 for corresponding Korean application No. 10-2006-7022602, and English translation thereof.
NCBI GenBankAccess. No. NM_002941.1 (Dec. 19, 2001).
NCBI GenBankAccess. No. NM_133631.1 (Mar. 26, 2002).
Extended European Search Report issued on Aug. 4, 2010 in connection with corresponding European Patent Application No. 10003419.8.
Kulasingam≠§, Vathany, et al., "Proteomics Analysis of Conditioned Media from Three Breast Cancer Cell Lines", Molecular & Cellular Proteomics 6.11, pp. 1997-2011, 2007.
Gröne, Jörn, et al., "Robo1/Robo4: Differential expression of angiogenic markers in colorectal cancer", Oncology Reports 15: pp. 1437-1443, 2006.

* cited by examiner

*Primary Examiner* — Peter J Reddig
(74) *Attorney, Agent, or Firm* — Sterne, Kessler, Goldstein & Fox P.L.L.C.

(57) ABSTRACT

A method for diagnosing cancer comprising detecting ROBO1 protein is disclosed. In addition, a method for treating a disease caused by abnormal cell growth comprising administrating an antibody that binds to ROBO1, as well as a pharmaceutical composition, a cell growth inhibitor and an anticancer agent comprising an antibody that binds to ROBO1 as an active ingredient are disclosed. Further, a method for inducing cell damages in a ROBO1 expressing cell and a method for inhibiting the growth of a ROBO1 expressing cell by bringing a ROBO1 expressing cell into contact with an antibody that binds to ROBO1, are disclosed. Furthermore, a method for monitoring progression of hepatitis by detecting ROBO1 protein is disclosed.

22 Claims, 17 Drawing Sheets

CANCER DIAGNOSIS AND TREATMENT OF CANCER USING ANTI-ROBO 1 ANTIBODY

CROSS-REFERENCES

The present invention relates to methods for the diagnosis and treatment of cancer and a method for monitoring progression of hepatitis, as well as to a cell growth inhibitor and an anticancer agent.

BACKGROUND

In genetic screening studies of *drosophila*, ROBO1 has been identified as a molecule regulating the midline crossing of axons, and has been reported to work as a receptor for the Slit protein in subsequent studies (Kidd et al., Cell, 92, 205-215, 1998, Wang et al., Cell, 96, 771-784, 1999, Kidd et al., Cell, 96, 785-794, 1999, Brose et al., 96, 795-806, 1999). In addition, regarding the relationship between ROBO1 and cancer, the chromosome region 3p12 where the human ROBO1 gene is present is highly defective in lung cancer, and expression is suppressed by methylation of the ROBO1 promoter region in breast cancer and kidney cancer, suggesting that ROBO1 gene can be a tumor suppressor gene (Dallol et al., Oncogene, 21, 3020-3028, 2000). Indeed, hyperplasia of tracheal epithelial cells was observed in mice by deleting the first immunoglobulin region present at the N-terminus of ROBO1, which is similar to the minimal defect in the ROBO1 gene identified in lung cancer patients (Xian J et al., PNAS, 98, 15062-15066, 2001). Conversely, it has been reported that ROBO1 was expressed in new blood vessels of cancers, and that increased expression of Slit2, a ligand for ROBO1, on the cancer cells induces cancer neovascularization to direct cancer growth (Wang et al., Cancer Cell, 4, 19-29, 2003).

Meanwhile, the expression of the Slit2 gene, which is a ligand for ROBO1, is also suppressed in a number of cancer types by methylation or the like, and overexpression of Slit2 or addition of Slit2 induces a growth inhibition and apoptosis in lung cancer, breast cancer and large intestine cancer cells. These observation suggests that Slit2, a ligand for ROBO1, is also thought to be a tumor suppressor gene (Dallol et al., Cancer Research, 62, 5874-5880, 2002, Dallol et al., Cancer Research, 63, 1054-1058, 2003). However, it is not clear in this report through which receptor Slit2 exerts its effect in inhibiting the cell growth, thus the relationship between ROBO1 and cancer has not been absolutely clear.

Cancer is the most common cause of death in Japan. Among them, primary hepatocellular cancer is one type of cancer with poor prognosis, representing the third leading case of death (13%) in male and the fourth (9.0%) in female in 2001 (excerpt from "Population Dynamics Statistics", Statistics and Information Department, Minster's Secretariat, Ministry of Health, Labour and Welfare). The number of chronic patients caused by viral infection is on the rise year after year and many of them lead to hepatic cirrhosis and then to hepatocellular cancers. Extremely strong demands exist for a diagnostic procedure at an early stage in the progression from hepatic cirrhosis to hepatocellular cancer and for a treatment of hepatocellular cancer. It is believed that without a groundbreaking solution, the number of deaths will follow an increasing trend in the 10 to 15 years to come.

Current hepatocellular cancer diagnostic procedure comprises a comprehensive evaluation based on biochemical data such as the serum value of GOP/GTP, alkaline phosphatase, albumin and the like, or a tumor marker AFP (a-fetoprotein), and diagnostic imaging. Then, if necessary, a small amount of tissue fragment is taken by needle biopsy for pathological judgment to confirm the diagnosis. Currently, tumor markers are mainly used for the diagnosis of hepatocellular cancer. The positive rate of alpha fetoprotein (AFP), which is the most common marker, is 60 to 70 percent in hepatocellular cancer patients, although it is sometimes also positive in chronic liver disease patients or pregnant female. Another hepatic cancer tumor marker PIVKA-II is positive in less than 50 percent of the patient, and the specificity for hepatocellular cancer is thought to be higher than AFP. Mainly these two examinations are currently in practice. In either case, false positive or double negative cases exist, thus a tumor marker with high specificity is needed.

Histological examination of the sample collected by needle biopsy is an important test for confirmed diagnosis of liver diseases. In particular, as the quantity of specimen may be limited, a more definite diagnosis technique is required. It is desired in the art to develop an antibody against an antigen specifically expressed in hepatic cancer to allow for not only pathological characteristics but also identification of hepatocellular cancer from a non-cancer tissue at an early stage.

In the current situation of diagnosis and monitoring of liver disease, progression from inflammation to fibrosis and malignant transformation are diagnosed by examination with multiple markers and examination by biopsy. In many hepatic cancer patients, the progression occurs from viral infection to hepatitis, chronic hepatitis, hepatic cirrhosis and then hepatic cancer. Consequently, a simple method for diagnosis and monitoring of liver diseases will be useful, not only in terms of healthcare economy, but also in mitigating the burden on the patients and in obtaining accurate medical guidelines.

Regarding treatment of hepatocellular cancer, many medical facilities are centered mainly on three types of therapy: surgical removal, transcatheter arterial embolization therapy, and percutaneous ethanol injection therapy. Either method has advantages and disadvantages, and even when transcatheter arterial embolization therapy is selected, which has a relatively broad application range and survival advantages, the rate of complete cure is currently thought to be on the order of 10%. Thus there is a great demand for a novel therapy.

Targeted therapy by monoclonal antibody against cancer specific tumor antigen provides a better outcome in breast cancer and in lymphoma and the like through an action mechanism different from conventional chemotherapy, although no clinical application has done for hepatocellular cancers yet. The action mechanisms of these antibody drugs include antibody dependent cytotoxicity (ADCC) via effector cells and complement-dependent cytotoxicity (CDC) via the complement, agonistic action by the function of the antibody itself, and the neutralization capability of the antibody. Recently molecular therapies have been applied in clinical sites. An antibody drug therapy which applies these molecular therapies and targets to a neoplasm-specifically expressed molecule found on hepatic cancer cells is expected to be developed in the future.

The following are documents related to the present invention: WO99/20764; WO98/48051; WO01/46697; WO03/29488; WO01/00828; WO01/57207; WO01/92581; WO02/04514; WO02/14500; WO02/29103.

SUMMARY OF INVENTION

An object of the present invention is to provide a novel method for diagnosing and treating cancer, as well as a novel cell growth inhibitor and anticancer agent, and to provide a method for diagnosing and monitoring liver disease.

The present inventors discovered that ROBO1 was highly expressed in cancer cells, such as hepatocellular cancer, lung cancer, breast cancer, uterine cancer, gastric cancer, brain tumor, large intestine cancer and the like. In addition, they measured the complement-dependent cytotoxicity (CDC) of the anti-ROBO1 antibody, and found that the anti-ROBO1 antibody had a CDC activity against ROBO1 expressing cells. They also found that the concentration of ROBO1 in blood increased with the progression of liver diseases. From the above observations, the present inventors discovered the effectiveness of the anti-ROBO1 antibody in the diagnosis, prevention and treatment of cancers overexpressing ROBO1, such as hepatocellular cancer, and achieved a method for diagnosing and monitoring liver diseases.

The present invention provides a method for diagnosing cancer comprising detecting ROBO1 protein. In the method of the present invention, preferably the extracellular region of the ROBO1 protein is detected. The method of the present invention is carried out preferably using an antibody that recognizes ROBO1 protein. Preferably, in the method of the present invention, ROBO1 protein in the blood, serum or plasma, or ROBO1 protein isolated from a cell is detected.

In another aspect, the present invention provides a method for diagnosing cancer comprising the steps of:
(a) collecting a sample from a subject; and
(b) detecting ROBO1 protein contained in the collected sample.

In another aspect, the present invention provides a kit for diagnosing cancer, comprising an antibody that binds to ROBO1 protein. Preferably, the cancer is hepatocellular cancer. Also, in the kit of the present invention, the antibody preferably binds to the extracellular region of the ROBO1 protein.

In another aspect, the present invention provides a pharmaceutical composition comprising an antibody that binds to ROBO1 as an active ingredient. The present invention also provides a cell growth inhibitor comprising an antibody that binds to ROBO1 as an active ingredient. The present invention also provides an anticancer agent comprising an antibody that binds to ROBO1 as an active ingredient. Preferably, the antibody that binds to ROBO1 has cytotoxicity. The cancer is preferably a hepatocellular cancer.

In another aspect, the present invention provides a method for treating a disease caused by abnormal cell growth, comprising administrating to a patient in need of such treatment a pharmaceutical composition comprising an antibody that binds to ROBO1 as an active ingredient. The present invention also provides a method for treating cancer, comprising administrating to a patient in need of such treatment a pharmaceutical composition comprising an antibody that binds to ROBO1 as an active ingredient. Preferably, the cancer is hepatocellular cancer.

In another aspect, the present invention provides a method for inducing cell damages in a ROBO1 expressing cell by bringing a ROBO1 expressing cell into contact with an antibody that binds to ROBO1. The present invention also provides a method for inhibiting the growth of a ROBO1 expressing cell by bringing a ROBO1 expressing cell into contact with an antibody that binds to ROBO1. Preferably, the antibody that binds to ROBO1 has cytotoxicity. Preferably, the ROBO1 expressing cell is a cancer cell.

In still another aspect, the present invention provides an antibody that binds to ROBO1 and has cytotoxicity against a ROBO1 expressing cell.

In another aspect, the present invention provides a kit for monitoring the progression of hepatitis comprising an anti-ROBO1 antibody. Preferably, the anti-ROBO1 antibody specifically recognizes ROBO1. Preferably, the kit of the present invention predicts the progression from hepatitis or hepatic cirrhosis to hepatic cancer. In a preferred embodiment, the kit of the present invention contains a first anti-ROBO1 antibody immobilized on a support and a second anti-ROBO1 antibody labeled with a labeling substance.

In still another aspect, the present invention provides a method for monitoring the progression of hepatitis by measuring ROBO1 in a test sample. Preferably, the ROBO1 in the test sample is measured using an anti-ROBO1 antibody. Preferably, the anti-ROBO1 antibody specifically recognizes ROBO1. Preferably, the test sample is blood, serum or plasma. Preferably, the monitoring method of the present invention predicts the progression from hepatitis or hepatic cirrhosis to hepatic cancer. In a preferred embodiment, the monitoring method of the present invention is carried out using a first anti-ROBO1 antibody immobilized on a support and a second anti-ROBO1 antibody labeled with a labeling substance.

DESCRIPTION OF DRAWINGS

FIG. 1a: ROBO1 gene expression analysis in normal tissues/non-cancer sites; FIG. 1b: ROBO1 gene expression analysis in clinical samples; FIG. 1c: ROBO1 gene expression analysis in cancer cell lines;

DETAILED DESCRIPTION OF INVENTION

Figure 1:
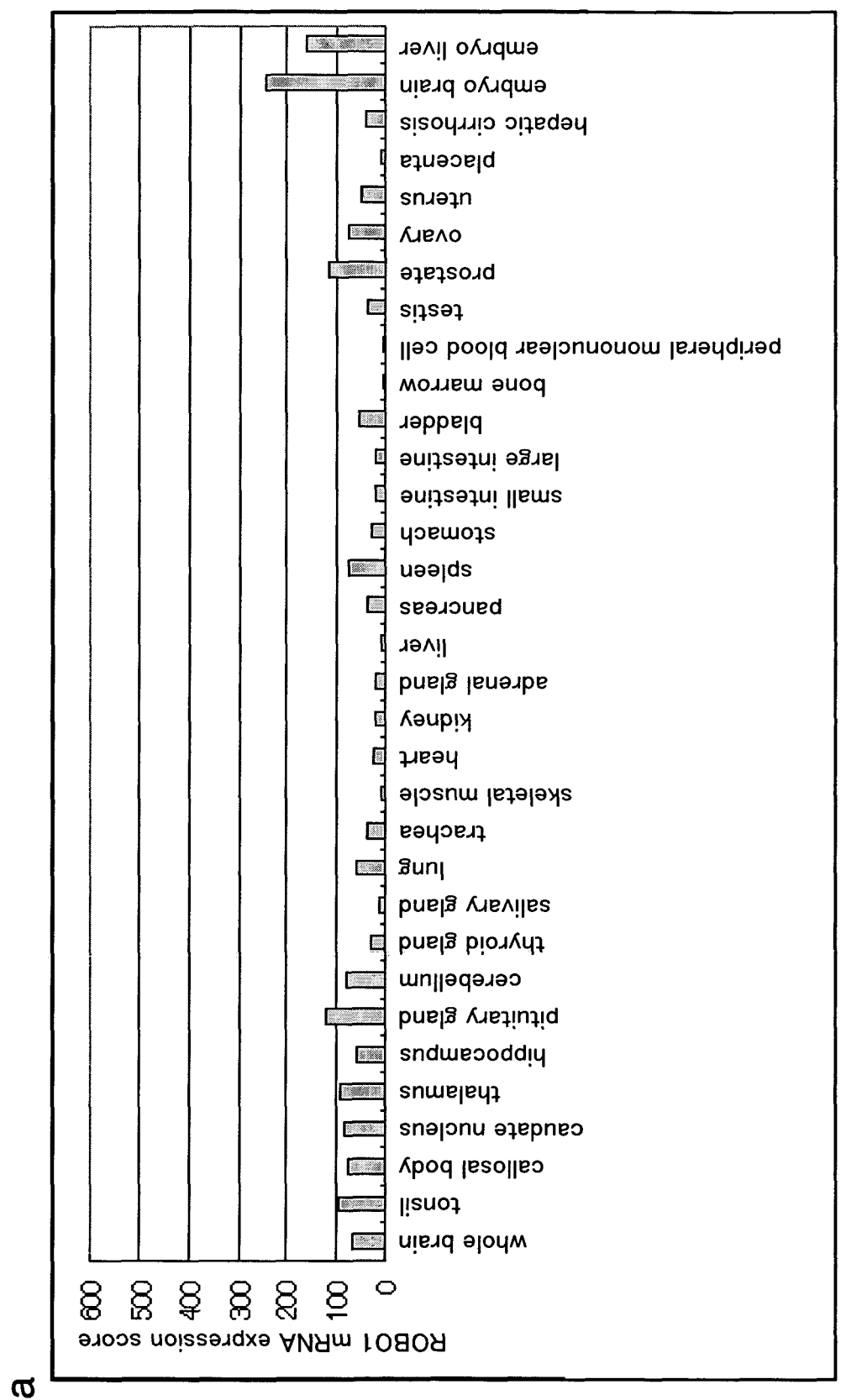
FIG. 1 shows the results of ROBO1 gene expression analysis using GeneChip U133.
Figure 1:
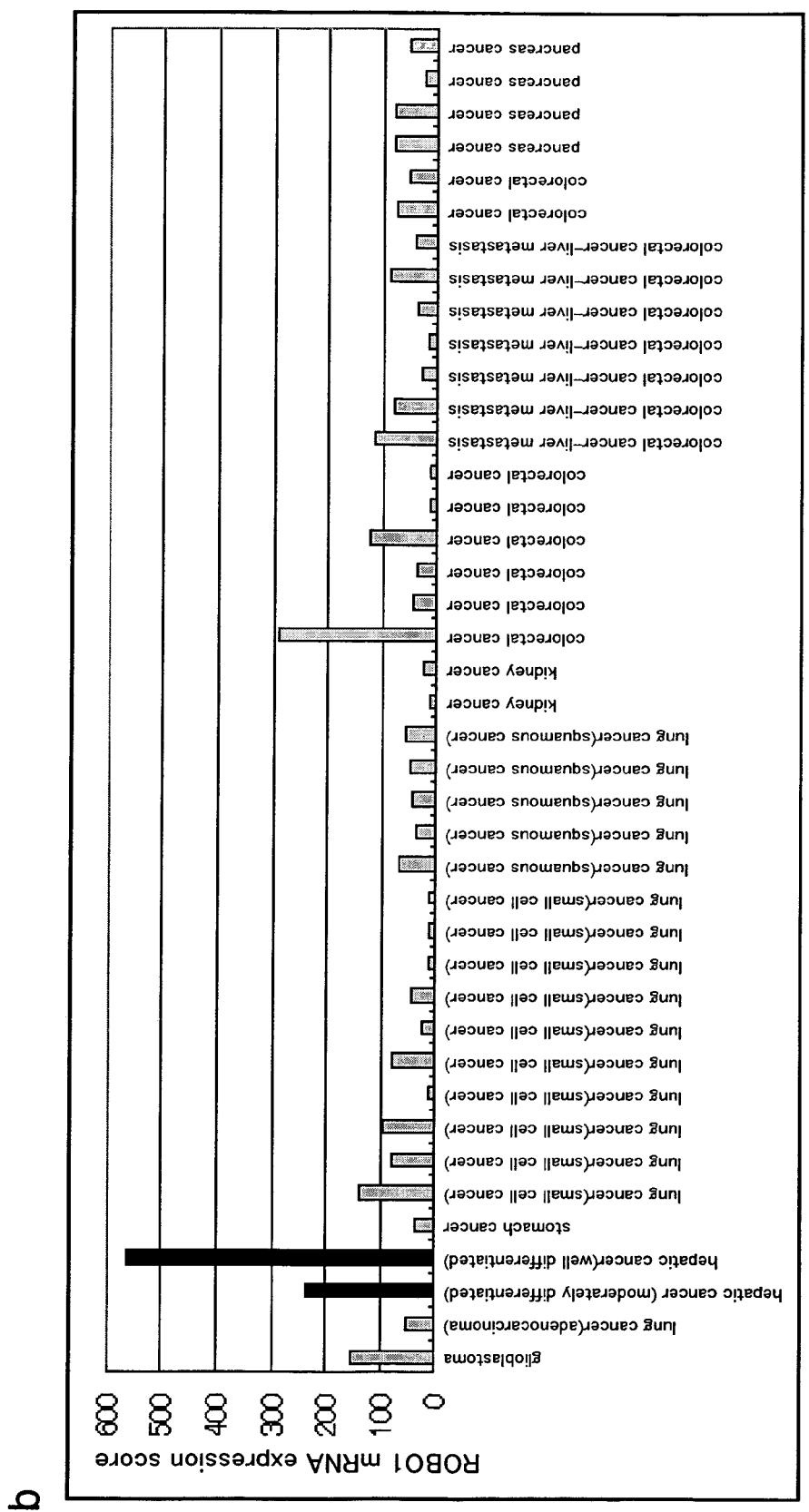
Figure 1:
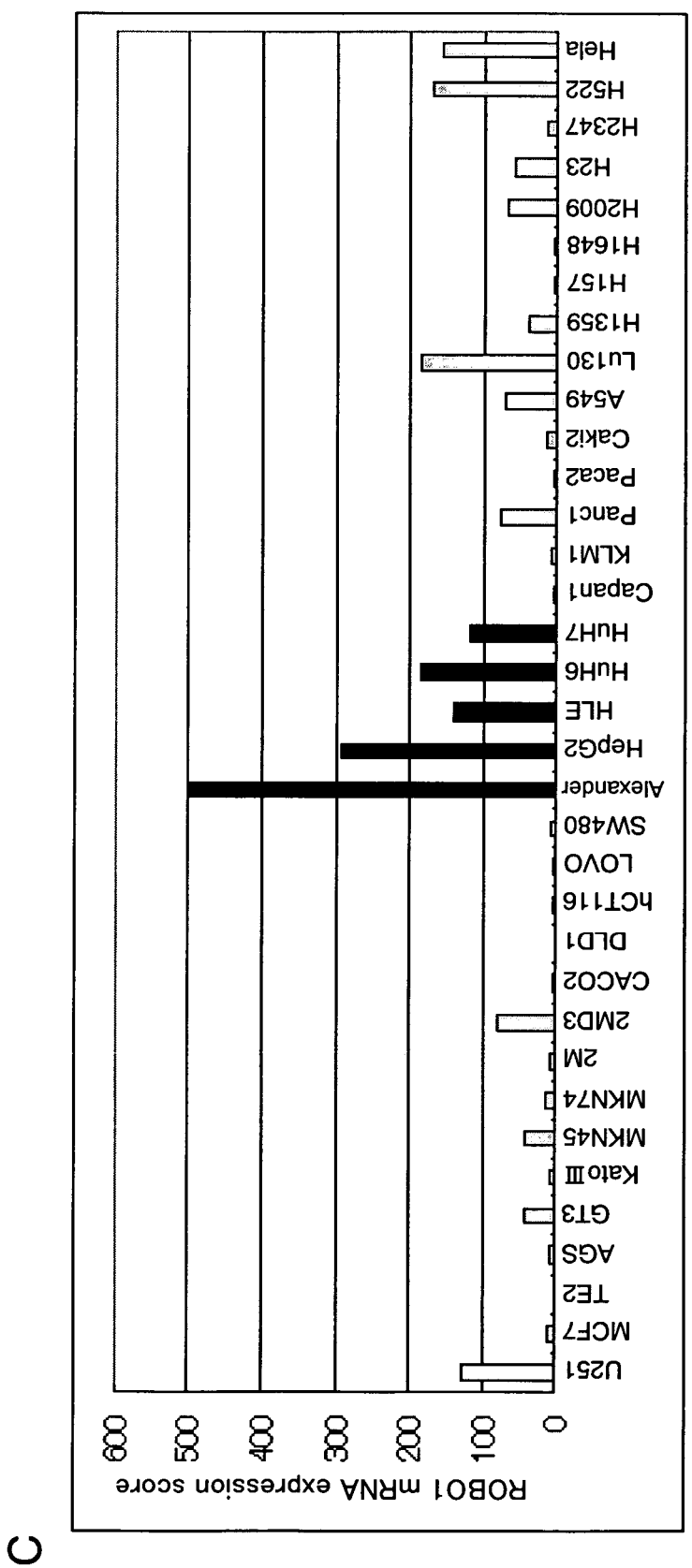

The method of the present invention is characterized by the detection of ROBO1 protein. ROBO1 (Roundabout 1) is an axon guidance receptor protein, and its amino acid sequence and the gene sequence coding therefor are disclosed in GenBank ID NM_002941 (SEQ ID NOs: 9 and 10) for variant 1, and GenBank ID NM_133631 (SEQ ID NOs: 11 and 12) for variant 2. In the present invention, ROBO1 protein is meant to include both the full length protein and fragments thereof. A fragment is a polypeptide containing any region of the ROBO1 protein, and may not have the function of the natural ROBO1 protein. Examples of fragments include, but are not limited to, a fragment containing an extracellular region of the ROBO1 protein. The extracellular region of the ROBO1 protein corresponds to positions 1-859 in the amino acid sequence of SEQ ID NO: 11. In addition, the membrane spanning region corresponds to positions 860-880 in the amino acid sequence of SEQ ID NO: 11 (Sundaresan, et al., Molecular and Cellular Neuroscience 11, 29-35, 1998).

In the present invention, the expression of ROBO1 was found to be enhanced at both the genetic level and the protein level with extremely high frequencies in hepatocellular cancer. In addition, the analysis of clinical samples and cancer cells line of other cancer species suggested that the enhanced expression was shown not only in hepatocellular cancer, but also in lung cancer, breast cancer, uterine cancer, gastric cancer, brain tumor, large intestine cancer and the like. It was also shown that immunohistological diagnosis can be carried out using a monoclonal antibody specific to ROBO1. In addition, ROBO1 was found to be shedded in vivo, and a soluble ROBO1 (sROBO1) was present in the blood of cancer patients, indicating that sROBO1 is useful as a serodiagnosis marker of cancer.

Detection of ROBO1

ROBO1 protein detected in the present invention is preferably human ROBO1 protein, but any ROBO1 may be used in the invention, including, but is not limited to, canine ROBO1, feline ROBO1, mouse ROBO1 and hamster ROBO1.

In the present invention, detection may be quantitative or non-quantitative. Examples of non-quantitative detection include measurement as to merely whether ROBO1 protein is present, measurement as to whether a given quantity or more ROBO1 protein is present, measurement comparing the amount of ROBO1 protein with other sample (for instance, control sample). Examples of quantitative detection include measurement of ROBO1 protein concentration, measurement of ROBO1 protein quantity, and the like.

Test samples are not particularly limited as long as they may contain ROBO1 protein, and are preferably those collected from the bodies of living organisms such as mammals, more preferably those collected from humans. Specific examples of test samples include, for instance, blood, interstitial tissue fluid, plasma, extravascular fluid, cerebrospinal fluid, synovial fluid, pleural fluid, serum, lymph, saliva, urine and the like, preferably blood, serum, or plasma. Preferably, the test samples used in the present invention also include those derived from the original test samples, such as the culture solution of cells collected from the body of a living organism.

The cancer to be diagnosed is not particularly limited and may be any cancer, including hepatic cancer, pancreatic cancer, lung cancer, large intestine cancer, breast cancer, kidney cancer, brain tumor, uterine cancer, lung cancer, gastric cancer, prostate gland cancer, leukemia, lymphoma and the like. Hepatic cancer is preferred, and hepatocellular cancer is more preferred.

In the present invention, when ROBO1 protein is detected in a test sample, and the amount of ROBO1 protein detected is determined to be higher than a negative control or a healthy subject, the subject is determined as having cancer or as having high potentiality to develop cancer.

In addition, progression of a liver disease can be monitored by measuring the concentration of ROBO1 protein in a patient having the liver disease.

A preferred embodiment of the diagnosis method of the present invention is detection of ROBO1 protein released from cells and present in blood. Particularly preferably, a fragment containing the extracellular region of the ROBO1 protein is detected.

Method for detecting ROBO1 protein contained in a test sample is not limited, but preferably include, detection by an immunological method using an anti-ROBO1 antibody. Examples of immunological methods include, for instance, radioimmunoassay, enzyme immunoassay, fluorescence immunoassay, luminescence immunoassay, immunoprecipitation method, immunonephelometry, Western blot, immunostaining, immunodiffusion method and the like, preferably enzyme immunoassay, and particularly preferably enzyme-linked immunosorbent assay (ELISA) (for instance, sandwich ELISA). The immunological methods such as ELISA can be carried out by those skilled in the art according to well known methods.

For instance, general detection of ROBO1 protein in a test sample using an anti-ROBO1 antibody may be carried out by immobilizing an anti-ROBO1 antibody on a support, adding a test sample, incubating the sample to bind ROBO1 protein to the anti-ROBO1 antibody, washing, and detecting the ROBO1 protein bound to the support via the anti-ROBO1 antibody.

Examples of supports used for immobilizing anti-ROBO1 antibody in the present invention may include, for instance, insoluble polysaccharides such as agarose and cellulose, synthetic resins such as silicon resin, polystyrene resin, polyacrylamide resin, nylon resin and polycarbonate resin, and insoluble supports such as glass. The support may be used in the form of beads or plates. In case of beads, a column may be filled with the beads. In case of plates, multi-well plate (96-well multi-well plate or the like), biosensor chip and the like can be used. For binding the anti-ROBO1 antibody to the support, conventional binding methods may be used, such as chemical bond or physical adsorption. Commercially available supports may be used for these purposes.

Binding of anti-ROBO1 antibody to ROBO1 protein is conventionally carried out in a buffer solution, such as phosphate buffer solution, Tris buffer solution, citric acid buffer solution, borate buffer solution, carbonate buffer solution, and the like. In addition, regarding incubation conditions, for instance, incubation for 1 hour to 24 hours at 4° C. to room temperature is carried out under conventionally used conditions. The procedure may optionally contain a washing step using a buffer solution containing a surfactant such as Tween 20 or the like, as long as it does not prevent binding of the anti-ROBO1 antibody to ROBO1 protein.

In the ROBO1 protein detection method of the present invention, a control sample may be prepared in addition to the test sample to be tested for ROBO1 protein. Examples of control samples include a negative control sample that does not contain ROBO1 protein, and a positive control sample that contains ROBO1 protein. In this case, the ROBO1 protein can be detected in the test sample by comparison with results obtained from the negative control sample without ROBO1 protein, and results obtained from the positive control sample with ROBO1 protein. In addition, a series of control samples with increment in concentration is prepared and a standard curve is established from the detection result for each control sample. ROBO1 protein contained in a test sample may be quantitatively determined from the numerical value for the test sample based on the standard curve.

In a preferred embodiment, the ROBO1 protein bound to the support via the anti-ROBO1 antibody is detected using an anti-ROBO1 antibody labeled with a labeling substance. For instance, a test sample is brought into contact with an anti-ROBO1 antibody immobilized on a support, and after washing, ROBO1 is detected using a labeled antibody that specifically recognizes the ROBO1 protein.

The labeling of an anti-ROBO1 antibody can be carried out by generally known methods. Labeling substances well known to those skilled in the art may be used, for example, fluorescent dyes, enzymes, coenzymes, chemiluminescent substances. Examples of the labeling substance include radioisotopes ($^{32}P$, $^{14}C$, $^{125}I$, $^{3}H$, $^{131}I$ and the like), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin and the like. Preferably, when using biotin as a labeling substance, a biotinylated antibody is added and then avidin conjugated with an enzyme such as alkaline phosphatase is added. Well known methods can be used for preparing a conjugation of the labeling substance and the anti-ROBO1 antibody, such as, the glutaraldehyde method, the maleimide method, the pyridyl disulphide method and the periodic acid method.

In a specific example, a solution containing anti-ROBO1 antibody is added to a support, such as a plate having the anti-ROBO1 antibody immobilized onto the support. After washing the plate, it is blocked with, for instance, BSA, gelatine, albumin or the like, to prevent non-specific binding of proteins. The plate is washed again, and a test sample is added to the plate. After incubation, the plate is washed, and a labeled anti-ROBO1 antibody is added. After an adequate incubation, the plate is washed and the labeled anti-ROBO1 antibody remaining on the plate is detected. The detection can be carried out by methods well known to those skilled in the art. For instance, in the case of labeling by a radioactive substance, it may be detected by liquid scintillation or the RIA method. In the case of labeling by an enzyme, a substrate is added and the enzymatic modification of the substrate, for instance color development, can be detected using a photometer. Examples of substrates include 2,2-azinobis(3-ethylbenzothiazolin-6-sulfonic acid) diammonium salt (ABTS), 1,2-phenylene diamine(ortho-phenylene diamine), 3,3',5,5'-tetramethylbenzin (TMB) and the like. In the case of a fluorescent substance, it may be detected with a spectrofluorimeter.

In a particularly preferred embodiment of the present invention, ROBO1 protein is detected using a biotin-labeled anti-ROBO1 antibody and avidin.

In a specific example, a solution containing anti-ROBO1 antibody is added to a support to immobilize the anti-ROBO1 antibody to the support, such as a plate. After washing the plate, it is blocked with, for instance, BSA or the like, to prevent non-specific binding of proteins. The plate is washed again, and a test sample is added to the plate. After incubation, the plate is washed, and a biotinylated anti-ROBO1 antibody is added. After an adequate incubation, the plate is washed, and avidin conjugated with an enzyme such as alkaline phosphatase or peroxidase is added. After incubation, the plate is washed, a substrate corresponding to the enzyme conjugated to avidin is added, and the ROBO1 protein is detected with the enzymatic modification of the substrate as the indicator.

In another preferred embodiment of the present invention, ROBO1 protein may be detected using one or more species of a primary antibody that specifically recognizes the ROBO1 protein, and one or more species of a secondary antibody that specifically recognizes the primary antibody.

For instance, a test sample is brought into contact with one or more species of an anti-ROBO1 antibody immobilized on a support, incubated and washed. Then the ROBO1 protein bound is detected with a primary anti-ROBO1 antibody and one or more species of a secondary antibody that specifically recognizes the primary antibody. In this case, the secondary antibody is preferably labeled with a labeling substance.

In another embodiment of the present invention, ROBO1 protein is detected using agglutination reaction. In this method, ROBO1 can be detected using a carrier sensitized with an anti-ROBO1 antibody. Any carriers may be used as carriers to be sensitized with the antibody, as long as they are insoluble, do not provoke non-specific reactions, and are stable. For instance, carriers include latex particles, bentonite, collodion, kaolin, immobilized sheep red blood cell and the like, preferably latex particles. For instance, polystyrene latex particles, styrene-butadiene copolymer latex particles, polyvinyl toluene latex particles may be used as latex particles. Polystyrene latex particles is preferred. The sensitized particles are mixed with a sample and stirred for a predetermined length of time. Since the higher the concentration of anti-ROBO1 antibody contained in the sample, the larger the degree of agglutination of the particles become, ROBO1 can be detected by direct observation of the agglutination. Also the turbidity due to agglutination may be measured with a spectrophotometer.

In another embodiment of the present invention, ROBO1 protein may be detected using a biosensor that employs, for instance, the surface plasmon resonance phenomenon. A biosensor that utilizes surface plasmon resonance phenomenon is able to detect protein-protein interaction in real time as a surface plasmon resonance signal, with a small amount of protein without labeling. For instance, binding of ROBO1 protein to anti-ROBO1 antibody can be detected using a biosensor such as the BIAcore (manufactured by Amersham Biosciences). In a specific example, a test sample is brought into contact with a sensor chip where an anti-ROBO1 antibody has been immobilized, and ROBO1 protein binding to anti-ROBO1 antibody can be detected as a variation in the resonance signal.

The detection method of the present invention may be automated using a variety of automatic examination apparatus, allowing examination for a number of samples to be carried out at once.

It is also an object of the present invention to provide a diagnosis drug or kit for detecting ROBO1 protein in a test sample for the diagnosis of cancer. Such a diagnosis drug or kit contains at least an anti-ROBO1 antibody. If the diagnosis drug or kit is based on an EIA method, such as the ELISA method, a carrier for immobilizing the antibody may be included, and the antibody may be pre-bound to the carrier. If the diagnosis drug or kit is based on an agglutination method using a carrier such as latex, a carrier with adsorbed antibody may be included. In addition, the kit may suitably contain a blocking solution, a reaction solution, a reaction stop solution, a reagent for processing a sample, and the like.

Preparation of Anti-ROBO1 Antibody

The anti-ROBO1 antibody used in the present invention specifically binds to ROBO1 protein, regardless of the origin, type (monoclonal, polyclonal) and shape thereof. Well known antibodies such as mouse antibodies, rat antibodies, human antibodies, chimeric antibodies, and humanized antibodies may be used in the invention. The antibody may be a polyclonal antibody, but a monoclonal antibody is preferred.

The anti-ROBO1 antibody used in the present invention can be obtained as a polyclonal or monoclonal antibody using well known means. In particular, monoclonal antibodies that are derived from a mammal are preferred as the anti-ROBO1 antibody used in the present invention. Monoclonal antibodies derived from a mammal include those produced by hybridoma, and those produced by a host that has been transformed with an expression vector containing the antibody gene by a genetic engineering method.

A monoclonal antibody-producing hybridoma can be prepared basically using well known techniques, in the following way. An animal is immunized with ROBO1 as a sensitizing antigen according to a conventional immunization method. Immunocytes from the animal is fused with a well known parental cell by a conventional cell fusion method, and screening for an antibody-producing monoclonal cell by a conventional screening method.

Specifically, a monoclonal antibody may be prepared in the following way. First, ROBO1 is expressed and used as a sensitizing antigen to generate antibodies. The gene/amino acid sequence of ROBO1 is disclosed in the GenBank Accession Number BF059159 (NM_133631). The gene coding for ROBO1 is inserted into a well known expression vector system and transformed a suitable host cell. The human ROBO1 protein of interest is purified from the host cell or the culture supernatant by a well known method. Alternatively, natural ROBO1 may also be purified and used.

Next, the purified ROBO1 protein is used as a sensitizing antigen. Alternatively, a partial peptide from ROBO1 can also be used as a sensitizing antigen. In this case, the partial peptide may be obtained by chemical synthesis based on the amino acid sequence of the human ROBO1, or by expression of a portion of the ROBO1 gene inserted into an expression vector, or by degradation of the natural ROBO1 with a protease. The region and size of ROBO1 to be used as the partial peptide is not limited.

The type of mammals to be immunized with the sensitizing antigen are not particularly limited but is preferably selected based on the compatibility with the parental cell used for cell fusion. In general, rodents, for instance, mouse, rat and hamster, or rabbit, monkey and the like are used.

An animal is immunized with the sensitizing antigen according to a well known method. In general, a mammal is immunize by injecting the sensitizing antigen intraperitoneally or subcutaneously into the mammal. Specifically, a sensitizing antigen is suitably diluted and suspended in PBS (Phosphate-Buffered Saline), physiological saline or the like, and mixed with a suitable amount of conventional adjuvant, for instance Freund complete adjuvant as desired. A mammal is administered with the emulsion several times every 4 to 21 days. A suitable carrier may also be used with the sensitizing antigen during immunization. If a partial peptide with a particularly small molecular is used as the sensitizing antigen, it is desirable to conjugate the peptide with a carrier protein such as albumin and keyhole limpet hemocyanin before immunization.

After a mammal is immunized as described above and the increase in the desired antibody level in the serum is observed, the immunocytes are taken out from the mammal and are subjected to cell fusion. Preferred immunocytes include, in particular, the spleen cells.

A mammalian myeloma cell may also be used as a parent cell for cell fusion with the immunocyte. Preferably, known variety cell lines are used as the myeloma cell such as P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), and R210 (Galfre, G. et al., Nature (1979) 277, 131-133).

The cell fusion of the immunocyte and the myeloma cell may be effected principally according to a known method such as a method of Kohler and Milstein et al. (Kohler, G. and Milstein, C., Methods Enzymol. (1981) 73, 3-46).

More specifically, the cell fusion is carried out in a conventional nutritional medium in the presence of, for example, a cell fusion-promoting agent. The cell fusion-promoting agent include, for example, polyethyleneglycol (PEG), Sendai virus (HVJ) or the like. An auxiliary agent such as dimethylsulfoxide can also be used to increase the fusion efficiency as needed.

The ratio of the number of the immunocyte to the myeloma cell to be used may be appropriately determined. For example, the number of the immunocyte is preferred to be set at 1 to 10 times that of the myeloma cell. The culture medium to be used in the above-mentioned cell fusion includes culture media suitable for the growth of the above-mentioned myeloma cell line, for example, RPMI 1640 culture medium and MEM culture medium, and a standard culture medium which is used for this type of cell culture. A serum supplement such as fetal calf serum (FCS) may be used in combination.

In cell fusion, predetermined number of the immunocytes and myeloma cells are thoroughly mixed in the culture medium, a PEG solution previously heated to about 37oC (for example, an average molecular weight of about 1000 to 6000) is added at a concentration of 30 to 60% (w/v) and mixed to form a desired fusion cell (hybridoma). Then, the process of sequential addition of an appropriate culture medium, centrifugation and removal of a supernatant is repeated to remove the cell fusion agent and those which are undesirable for the growth of the hybridoma.

The resulting hybridoma is then selected by culturing it in a standard selection culture medium such as HAT culture medium (a culture medium containing hypoxanthine, aminopterin, and thymidine). The cultivation in the above-mentioned HAT culture medium is continued for sufficient time (usually from several days to several weeks) so that cells other than the desired hybridoma (non-fused cells) will die. Then, a hybridoma that produces a desired antibody is screened and monocloned by a standard limiting dilution method.

Note that the antibody that recognizes ROBO1 can also be prepared using the method described in International Publication WO03/104453.

A desired antibody may be screened and monocloned by a known screening method based on an antigen-antibody reaction. For example, an antigen is bound to a support such as beads made of polystyrene or the like or a commercially available 96-well microtiter plate, then a culture supernatant of hybridoma is added. After the support is washed, an enzyme-labeled secondary antibody or the like is added to determine whether or not a desired antibody reacting with the sensitizing antigen is contained in the culture supernatant. The hybridoma that produces a desired antibody can be cloned by a limiting dilution method or the like. The antigen used for immunization may be used in the screening procedure.

In addition to the method where an animal other than human is immunized with an antigen to obtain a hybridoma, it is also possible to sensitize a human lymphocyte in vitro with ROBO1, and the resulting sensitized lymphocyte is fused with a human myeloma cell having the ability to divide permanently, whereby a desired human antibody having the activity of binding to ROBO1 can be obtained (see JP-B-1-59878). Alternatively, ROBO1 is administered to a transgenic animal having the repertoire of all the genes for human antibody to obtain a cell producing the anti-ROBO1 antibody. The cell is immortalized and a human antibody against ROBO1 may be obtained from the immortalized cell (see International Patent Application Nos. WO 94/25585, WO 93/12227, WO 92/03918 and WO 94/02602).

The thus prepared hybridoma that produces a monoclonal antibody can be subcultured in a standard culture medium, or can be stored for a long period of time in liquid nitrogen.

In order to obtain a monoclonal antibody from the hybridoma, the hybridoma is cultured according to a standard method and an antibody is obtained as the culture supernatant. Alternatively, the hybridoma is administered to and grown in a mammal compatible with the hybridoma and an antibody is obtained from the ascites of the mammal. The former method is suitable for obtaining high-purity antibodies, whereas the latter is suitable for mass production of antibodies.

According to the present invention, a recombinant monoclonal antibody produced by genetic engineering techniques can also be used as a monoclonal antibody. The antibody gene is cloned from the hybridoma, incorporated into an appropriate vector and introduced into the host cell to produce a recombinant-type monoclonal antibody (see, for example, Vandamme, A. M. et al., Eur. J. Biochem. (1990) 192, 767-775, 1990). Specifically, mRNA encoding the variable (V) region of the anti-ROBO1 antibody is isolated from the hybridoma producing the anti-ROBO1 antibody. The isolation of mRNA is carried out by a known method such as guanidine ultracentrifugation (Chirgwin, J. M. et al. Biochemistry (1979) 18, 5294-5299) or the AGPC method (Chomczynski, P. et al., Anal. Biochem. (1987) 162, 156-159) to prepare total RNA, and then a desired mRNA is prepared by using an mRNA Purification Kit (manufactured by Pharmacia). Alternatively, mRNA can be directly prepared by using a Quick-Prep mRNA Purification Kit (manufactured by Pharmacia).

cDNA coding for the V region of the antibody is synthesized from the resulting mRNA by using a reverse transcriptase. The synthesis of the cDNA is carried out by using, for example, AMV Reverse Transcriptase First-strand cDNA Synthesis Kit (manufactured by Seikagaku Kogyo). Alternatively, cDNA may be synthesized and amplified by the 5'-RACE method (Frohman, M. A. et al., Proc. Natl. Acad. Sci. USA (1988) 85, 8998-9002, Belyavsky, A. et al., Nucleic Acids Res. (1989) 17, 2919-2932) using a 5'-Ampli FINDER RACE Kit (manufactured by Clontech), PCR and the like.

The desired DNA fragment is purified from the resulting PCR product and ligated with a vector DNA. Then a recombinant vector is constructed therefrom and introduced into *E. coli* or the like, and a colony is selected, whereby a desired recombinant vector is prepared. The nucleotide sequence of the desired DNA is checked by a known method such as the dideoxy nucleotide chain termination method. Once the desired DNA encoding the V region of the anti-ROBO1 antibody is obtained, and the DNA is incorporated into an expression vector containing DNA encoding the constant region (C region) of a desired antibody.

In order to produce the anti-ROBO1 antibody to be used in the present invention, the antibody gene is incorporated into an expression vector so as to be expressed under the control of the expression regulatory region, for example, an enhancer or a promoter. Subsequently, a host cell is transformed with the expression vector, and the antibody is expressed in the cell.

The antibody gene may be expressed in the cell by separately introducing DNAs encoding the heavy chain (H chain) and the light chain (L chain) of the antibody into expression vectors and co-transforming a host cell with the vectors; or by introducing DNAs encoding the H chain and the L chain into a single expression vector and transforming a host cell with the vector (see WO 94/11523).

When an antibody gene is isolated and introduced into a suitable host to produce an antibody, a combination of suitable host and expression vector can be used. Eucaryotic cells to be used as a host include animal cells, plant cells and fungal cells. Known animal cells include (1) mammalian cells, for instance, CHO, COS, myeloma, BHK (baby hamster kidney), HeLa and Vero, (2) amphibian cells, for instance, *Xenopus laevis* oocyte, or (3) insect cells, for instance, sf9, sf21, Tn5 and the like. Known plant cells include the *Nicotiana* genus, for instance, those derived from *Nicotiana tabacum*, which is grown in callus culture. Known fungal cells include yeast, for instance, the *Saccharomyces* genus such as *Saccharomyces serevisiae*, filamentous fungus, for instance, the *Aspergillus* genus such as *Aspergillus niger*, and the like. When using a prokaryotic cell, a production system using bacterial cell are available. Known bacterial cells include *Escherichia coli* (*E. coli*) and *Bacillus subtilis*. The target antibody gene is introduced into these cells by transformation, and the antibody may be obtained by culturing the transformed cells in vitro.

In addition to the above host cells, a transgenic animal can be used for the production of a recombinant antibody. For example, an antibody gene is inserted into the middle of a gene encoding a protein produced specifically into milk (such as goat β-casein) to prepare a fusion gene. A DNA fragment containing the fusion gene comprising the antibody gene is injected into a goat's embryo, which is then introduced into a female goat. A desired antibody can be obtained from milk produced by a transgenic goat which is born from the goat that had received the embryo or offspring thereof. To increase the amount of milk containing the desired antibody produced by the transgenic goat, an appropriate hormone may be administered to the transgenic goat (Ebert, K. M. et al., Bio/Technology (1994) 12, 699-702).

In the present invention, an artificially modified recombinant antibody, for instance, a chimeric antibody, a humanized antibody, can be used with the aim of decreasing heterologous antigenicity against human. These modified antibodies can be prepared using a known method. A chimeric antibody is an antibody comprising the variable regions on the heavy chain and the light chain of an antibody from a mammal other than human, such as mouse, and the constant regions on the heavy chain and light chain from a human antibody. It is obtained by ligating the DNA coding for the variable region of the mouse antibody and the DNA coding for the constant region of the human antibody, and incorporating into an expression vector, and introducing a host for antibody production.

C regions from the human antibody is used as the C region in the chimeric antibody or the humanized antibody. For example, Cγ1, Cγ2, Cγ3 or Cγ4 can be used for the H chain, and Cκ or Cλ can be used for the L chain. The C region of the human antibody may be modified in order to improve the stability of the antibody itself or the production process.

A chimeric antibody is composed of the variable region of an antibody derived from a non-human mammal and the constant region derived from a human antibody. On the other hand, a humanized antibody is composed of the complementarity determining region of an antibody derived a non-human mammal, and the framework region and the constant region derived from a human antibody. Since the antigenicity of the humanized antibody is expected to be reduced in human body, the humanized antibody is useful as an active ingredient of a therapeutic agent of the present invention.

A humanized antibody, also referred to as a "reshaped humane antibody", is obtained by grafting the complementarity determining region (CDR) of an antibody from a non-human mammal, such as a mouse, into the complementarity determining region of a human antibody. Specifically, a DNA sequence designed to ligate a mouse antibody CDR to the framework region (FR) of a human antibody is synthesized by PCR using as primers several oligonucleotides constructed to have overlapping portions at the ends of both CDR and FR.

The obtained DNA is ligated with the DNA coding for the constant region of the human antibody, then incorporated into an expression vector, which is introduced into and expressed by a host to obtain the antibody (see European Patent EP 239400 and International Publication WO 96/02576).

The framework region of the human antibody to be ligated via the CDR is selected such that the complementarity determining region will form a favorable antigen-binding site. As necessary, amino acids in the framework region of an antibody variable region may be substituted, so that the complementarity determining region of a reshaped human antibody forms an appropriate antigen-binding site (Sato, K. et al., Cancer Res. (1993) 53, 851-856).

In addition, a method for obtaining a human antibody is also known. For instance, a human lymphocyte is sensitized with a desired antigen or a cell expressing the desired antigen in vitro, and sensitized lymphocyte is fused with a human myeloma cell, for instance U266, to obtain the desired human antibody capable of binding to the antigen (refer to Japanese Patent Publication No. H1-59878). In addition, a transgenic animal having the entirety of the repertoire of human antibody genes can be immunized with the desired antigen to obtain the desired human antibody (refer to International Publication WO 93/12227, WO 92/03918, WO 94/02602, WO 94/25585, WO 96/34096 and WO 96/33735). In addition, a technique where a human antibody is selected by panning from a human antibody library is also known. For instance, the variable region of the human antibody is expressed as a single chain antibody (scFv) on the surface of a phage by the phage display method, and a phage binding to the antigen is selected. The gene of the selected phage is analyzed to determine the sequence of the DNA coding for the variable region of the human antibody binding to the antigen. Once the DNA sequence of the scFv binding to the antigen is determined, a suitable expression vector containing the sequence can be prepared to produce the human antibody. These methods are well known, and described in International Publication WO 92/01047, WO 92/20791, WO 93/06213, WO 93/11236, WO 93/19172, WO 95/01438 and WO 95/15388.

The antibody to be used in the present invention is not limited to the whole antibody molecule and may be a fragment of the antibody or a modified fragment thereof as long as it binds to ROBO1, including a divalent antibody and a monovalent antibody. Examples of the fragment of the antibody include Fab, F(ab')2, Fv, Fab/c having one Fab and a full Fc, and a single chain Fv (scFv) where the Fv of the H chain and the L chain are linked via an appropriate linker.

Specifically, an antibody is treated with an enzyme such as papain or pepsin to provide a fragment of the antibody. Alternatively, a gene encoding such an antibody fragment is constructed and introduced into an expression vector, and the antibody fragment is expressed in a suitable host cell (see, for example, Co, M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

The scFv can be obtained by linking the H chain V region and the L chain V region of an antibody. In the scFv, the H chain V region and the L chain V region are preferably linked via a linker, preferably a peptide linker (Huston, J. S. et al., Proc. Natl. Acad. Sci. U.S.A. (1988) 85, 5879-5883). The H chain V region and the L chain V region in scFv may be derived from any antibody described as an antibody in this specification. For example, any single chain peptide having 2 to 25 amino acid residues may be used as the peptide linker for ligating the V regions. DNA encoding scFv can be obtained by amplifying a fragment by PCR using as a template a DNA portion encoding all or a desired amino acid sequence of the sequences of DNA encoding the H chain or the H chain V region of the above-mentioned antibody and DNA encoding the L chain or the L chain V region of the above-mentioned antibody with a primer pair that defines the both ends thereof. Then the fragment is amplified with a combination of DNA encoding a peptide linker portion and a primer pair which defines both ends to be ligated to the H chain and the L chain. Once DNA encoding scFv is prepared, an expression vector containing the DNA and a host cell transformed with the expression vector can be obtained according to a standard method. The scFv can be obtained from such a host according to a standard method. These antibody fragments can be produced in a host by obtaining the gene thereof in the same manner as described above and by allowing it to be expressed.

A modified antibody conjugated with any of a variety of molecules such as polyethylene glycol (PEG) can also be used in the invention. It is also possible to conjugate the antibody with a cytotoxic agent, such as a radioisotope, a chemotherapeutic agent and a cell-derived cytotoxin. Such a modified antibody can be obtained by chemically modifying the antibody obtained as above. Methods of modifying an antibody have already been established in the art. The term "antibody" in the present invention also encompasses such a modified antibody.

Further, the antibody to be used in the present invention may be a bispecific antibody. The bispecific antibody may have antigen-binding sites that recognize different epitopes on the ROBO1 molecule. Alternatively, one of which may recognize ROBO1, and the other may recognize a cytotoxic agent, such as a radioactive substance, a chemotherapeutic agent or a cell-derived toxin. In this case, the cytotoxic agent can directly act on a cell expressing ROBO1 to specifically damage the tumor cells to inhibit the proliferation of the tumor cells. The bispecific antibody can also be produced by ligating an HL pair of two types of antibodies, or by fusing hybridomas producing different monoclonal antibodies to provide a fusion cell producing the bispecific antibody. Furthermore, the bispecific antibody can also be produced by genetic engineering techniques.

Antibodies can be expressed from the antibody gene constructed as described above by a known method. In the case of a mammalian cell, the gene can be expressed by operably linking a conventional useful promoter, an antibody gene to be expressed and a poly A signal at the 3'-downstream of the gene. A promoter/enhancer includes, for example, a human cytomegalovirus immediate early promoter/enhancer.

Further, examples of the promoter/enhancer used for expressing antibodies to be used in the present invention include, for example, viral promoter/enhancers such as retrovirus, polyoma virus, adenovirus and simian virus 40 (SV40), mammalian promoter/enhancers such as human elongation factor 1α (HEF1α).

Antibodies can be readily expressed by the method of Mulligan et al. (Nature (1979) 277, 108) when SV40 promoter/enhancer is used, and by the method of Mizushima et al. (Nucleic Acids Res. (1990) 18, 5322) when HEF1α promoter/enhancer is used.

In the case of *E. coli*, the gene can be expressed by operably linking a conventional useful promoter, a signal sequence for antibody secretion and an antibody gene to be expressed. A promoter includes, for example, lacZ promoter and araB promoter. The gene can be expressed by the method of Ward et al. (Nature (1989) 341, 544-546; FASEB J. (1992) 6, 2422-2427) when the lacZ promoter is used, and by the method of Better et al. (Science (1988) 240, 1041-1043) when the araB promoter is used.

A signal sequence for antibody secretion may be used for producing the antibody in the periplasm of *E. coli*, such as pelB signal sequence (Lei, S. P. et al., J. Bacteriol. (1987) 169, 4379). After isolating the antibody produced in the periplasm, the antibody is appropriately refolded for use.

A replication origin may be derived from SV40, polyoma virus, adenovirus, bovine papilloma virus (BPV). To amplify the gene copy number in a host cell system, the expression vector may contain as a selection marker the aminoglycoside transferase (APH) gene, the thymidine kinase (TK) gene, the *E. coli* xanthine guaninephosphoribosyl transferase (Ecogpt) gene, the dihydrofolate reductase (dhfr) gene or the like.

Any expression system, for example, a eukaryotic cell or a prokaryotic cell can be used for producing the antibody to be used in the present invention. Examples of the eukaryotic cell include established animals cells such as mammalian cells, insect cells, filamentous fungus cells, and yeast cells and the like. Examples of the prokaryotic cell include bacteria cells such as *E. coli* cells.

The antibody to be used in the present invention is preferably expressed in a mammalian cell such as a CHO, COS, myeloma, BHK, Vero, or Hela cell.

Subsequently, the transformed host cell is cultured in vitro or in vivo to produce a desired antibody. The host cell may be cultured according to a known method. For example, DMEM, MEM, RPMI1640 and IMDM can be used as a culture medium, and a serum supplement such as fetal calf serum (FCS) may be used in combination.

The thus expressed and produced antibody can be purified using known methods conventionally applied in protein purification. For example, the antibody can be isolated and purified by appropriately selecting and combining affinity columns such as Protein A column, chromatography columns, besides the above-mentioned, filters, ultra filtration, salting-out, dialysis and the like (Antibodies A Laboratory Manual, Ed Harlow, David Lane, Cold Spring Harbor Laboratory, 1988).

The antigen binding activity of the antibody may be measured by a known method (Antibodies A Laboratory Manual. Ed Harlow, David Lane, Cold Spring Harbor Laboratory, 1988) by, for instance, ELISA (enzyme linked immunosorbent assay), EIA (enzyme immuno assay), RIA (radioimmuno assay) or immunofluorescence.

Pharmaceutical Composition

In another aspect, the invention features a pharmaceutical composition comprising an antibody that binds to ROBO1 as an active ingredient. In addition, the present invention features a cell growth inhibitor, in particular an anticancer agent, comprising an antibody that binds to ROBO1 as an active ingredient.

In the present invention, the term "comprising an antibody that binds to ROBO1 as an active ingredient" means comprising an anti-ROBO1 antibody as a major active component, and is not meant to restrict the content ratio of the anti-ROBO1 antibody.

The antibody contained in the cell growth inhibitor of the present invention is not particularly limited, as long as it binds to ROBO1. Preferably, it is an antibody that binds specifically to ROBO1, and more preferably, it is an antibody that has cytotoxicity. In addition, the antibody used in the present invention may be an antibody with a modified glycosyl chain. It is known that cytotoxicity of an antibody can be increased by modifying its glycosyl chain. For instance, antibodies with modified glycosylation (WO99/54342 and the like), antibodies that are deficient in fucose added to the glycosyl chain (WO00/61739, WO02/31140 and the like)), antibodies having a glycosyl chain with a bisecting GlcNAc (WO02/79255 and the like) are known as those having modified glycosyl chain.

In the present invention, for instance, the cytotoxicity includes antibody-dependent cell-mediated cytotoxicity (ADCC) activity, complement-dependent cytotoxicity (CDC) activity, and the like. In the present invention, CDC activity means a cytotoxicity caused by the complement system. ADCC activity means that when a specific antibody attaches to the cell surface antigen of the target cell, an Fcγ receptor carrier cell (immune cell, etc.) binding to the Fc portion thereof via the Fcγ receptor damages the target cell.

An anti-ROBO1 antibody can be tested for its ADCC activity or CDC activity by well known methods (for instance, Current protocols in Immunology, Chapter 7. Immunologic studies in humans, Editor, John E, Coligan et al., John Wiley & Sons, Inc., (1993) and the like).

Specifically, first, effector cells, complement solution, and target cells are prepared.

(1) Preparation of Effector Cells

Spleen is extirpated from a CBA/N mouse or the like, and spleen cells are separated in RPMI1640 culture medium (manufactured by GIBCO). After washing in the same culture medium containing 10% fetal bovine serum (FBS, manufactured by HyClone), the cells are adjusted at a concentration of $5 \times 10^6$/ml, to prepare effector cells.

(2) Preparation of Complement Solution

Baby Rabbit Complement (manufactured by CEDARLANE) is diluted 10-fold in a culture medium (manufactured by GIBCO) containing 10% FBS, to prepare a complement solution.

(3) Preparation of Target Cell

Cells expressing ROBO1 (cells transformed with a gene coding for ROBO1, hepatic cancer cells, lung cancer cells, breast cancer cells, uterine cancer cells, gastric cancer cells, large intestine cancer cells, and the like) are radioactively labeled by incubating with 0.2 mCi of sodium chromate-$^{51}$Cr (manufactured by Amersham Pharmacia Biotech) in a DMEM culture medium containing 10% FBS for one hour at 37° C. After radioactive labeling, cells are washed three times with RPMI1640 culture medium containing 10% FBS, and adjusted at a concentration of 2×10$^5$/ml to prepare the target cells.

Next, the ADCC activity or the CDC activity is measured. In the case of ADCC activity measurement, 50 μl each of target cell and anti-ROBO1 antibody are added to a 96-well U bottom plate (manufactured by Beckton Dickinson), and incubated on ice for 15 minutes. Thereafter, 100 μl of effector cell are added and incubated in a carbon dioxide incubator for 4 hours. The final concentration of antibody is 0 or 10 μg/ml. After the culture, 100 μl of supernatant is collected, and the radioactivity is measured with a gamma counter (COBRAII AUTO-GAMMA, MODEL D5005, manufactured by Packard Instrument Company). The cytotoxicity (%) can be determined according to the equation:

$$(A-C)/(B-C)\times 100$$

wherein A represents the radioactivity (cpm) in a sample, B represents the radioactivity (cpm) in a sample where 1% NP-40 (manufactured by Nakarai) has been added, and C represents the radioactivity (cpm) of a sample containing the target cells only.

Meanwhile, in the case of CDC activity measurement, 50 μl each of target cell and anti-ROBO1 antibody are added to a 96-well flat-bottomed plate (manufactured by Becton Dickinson), and incubated on ice for 15 minutes. Thereafter, 100 μl of complement solution is added, and incubated in a carbon dioxide incubator for 4 hours. The final concentration of antibody is 0 or 3 μg/ml. After the culture, 100 μl of supernatant is collected, and the radioactivity is measured with a gamma counter. The cytotoxicity can be determined in the same way as in the ADCC activity.

Cells of which proliferation is inhibited by the anti-ROBO1 antibody are not particularly limited as long as they express ROBO1, and are preferably cancer cells, and more preferably hepatic cancer cells, lung cancer cells, breast cancer cells, uterine cancer cells, gastric cancer cells, brain tumor cells and large intestine cancer cells. The anti-ROBO1 antibody can be used for the purpose of treating and preventing diseases attributable to cell proliferation, for instance, hepatocellular cancer, lung cancer, breast cancer, uterine cancer, gastric cancer, brain tumor, large intestine cancer and the like.

The cell growth inhibitor and anticancer agent of the present invention may be administered orally or parenterally. Preferably it is administered parenterally in the form of, for example, injectable formulation, nasal administration formulation, pulmonary administration formulation, percutaneous administration formulation. An injectable formulation may be administered systemically or locally, for instance, by intravenous injection, intramuscular injection, intraperitoneal injection, subcutaneous injection, and the like. The administration route may be suitably selected according to the age of the patient and the symptoms. The dose may be selected within the range of 0.0001 mg to 1000 mg per kg body weight per administration. Alternatively, the dose may be selected for instance within the range of 0.001 to 100000 mg/body per patient. However, the therapeutic agent of the present invention is not limited to these doses.

The cell growth inhibitor and anticancer agent of the present invention can be formulated according to conventional methods (for instance, Remington's Pharmaceutical Science, latest edition, Mark Publishing Company, Easton, U.S.A), and may also contain pharmaceutically acceptable carriers and additives, for example, but not limited to, surfactant, diluent, colorant, perfume, preservative, stabilizer, buffer, suspending agent, isotonization agent, bonded, disintegrant, lubricant, fluidity promoting agent, flavoring agent and the like. Specific examples include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatine, medium chain fatty acid triglyceride, polyoxyethylene hardened castor oil 60, white sugar, carboxymethyl cellulose, corn starch, inorganic salt, and the like.

In addition, the present invention provides a method for inducing damages in a ROBO1 expressing cell and a method for inhibiting cell growth by contacting a ROBO1 expressing cell with an antibody that binds to ROBO1. The antibody that binds to ROBO1 to be contained in the cell growth inhibitor of the present invention is as described above. The cell that is bound by the anti-ROBO1 antibody is not particularly limited as long as the cell is expressing ROBO1, preferably a cancer cell, more preferably a hepatic cancer cell, a lung cancer cell, a breast cancer cell, a uterine cancer cell, a gastric cancer cell, a brain tumor cell and a large intestine cancer cell.

All the contents of the patent references and other references explicitly referred to in this description are incorporated herein by reference. In addition, the entire contents of the specification and the drawings of Japanese Patent Application Nos. 2004-102862, 2004-227899 and 2005-004024, which are the basic applications for the priority of the present application, are incorporated herein by reference.

EXAMPLES

The present invention will be described in further detail with the following examples; however these examples are not to limit the scope of the present invention.

Example 1 mRNA Expression Analysis of ROBO1 in Various Types of Cancer 1-1. ROBO1 Gene Expression Analysis Using Gene Chip To search for genes for which the expression is enhanced in cancer cells, various RNAs as well as total RNAs shown in Table 1 were prepared from various extracted tissues by conventional method using ISOGEN (manufactured by Nippon Gene) and analyzed.

TABLE 1

Tissues and cell lines used for the ROBO1 gene expression analysis

| Tissue | Origin | Lot# | Tissue | Origin |
|---|---|---|---|---|
| whole brain | Clontech 64020-1 | 101041 | glioblastoma | clinical sample |
| tonsil | Clontech 6574-1 | 1030830 | lung cancer(adenocarcinoma) | clinical sample |
| callosal body | Clontech 6577-1 | 1010486 | hepatic cancer (moderately differentiated) | clinical sample |
| caudate nucleus | Clontech 6575-1 | 120289 | hepatic cancer(well differentiated) | clinical sample |
| thalamus | Clontech 6582-1 | 1070147 | stomach cancer | clinical sample |
| hippocampus | Clontech 6578-1 | 1050638 | lung cancer(small cell cancer) | clinical sample |
| pituitary gland | Clontech 6584-1 | 2010981 | lung cancer(small cell cancer) | clinical sample |

TABLE 1-continued

Tissues and cell lines used for the ROBO1 gene expression analysis

| | | | | |
|---|---|---|---|---|
| cerebellum | Clontech 64035-1 | 1010033 | lung cancer(small cell cancer) | clinical sample |
| thyroid gland | Stratagone 735040 | 510225 | lung cancer(small cell cancer) | clinical sample |
| salivary gland | Clontech 64026-1 | 1011322 | lung cancer(small cell cancer) | clinical sample |
| lung | clinical sample | 14887 | lung cancer(small cell cancer) | clinical sample |
| trachea | Clontech 64091-1 | 1010201 | lung cancer(small cell cancer) | clinical sample |
| skeletal muscle | Ambion 7982 | 091P0101C | lung cancer(small cell cancer) | clinical sample |
| heart | Ambion 7966 | 110P43B | lung cancer(small cell cancer) | clinical sample |
| kidney | Ambion 7976 | 071P04B | lung cancer(small cell cancer) | clinical sample |
| adrenal gland | Clontech64096-1 | 2020671 | lung cancer(squamous cancer) | clinical sample |
| liver | clinical sample (Surgery) | N4 | lung cancer(squamous cancer) | clinical sample |
| pancreas | Ambion 7954 | 091P0104A | lung cancer(squamous cancer) | clinical sample |
| spleen | Ambion 7970 | 061P18A | lung cancer(squamous cancer) | clinical sample |
| stomach | clinical sample (Surgery) | MN15 | lung cancer(squamous cancer) | clinical sample |
| small intestine | Ambion 7984 | 091P0201A | kidney cancer | clinical sample |
| large intestine | Ambion 7986 | 071P10B | kidney cancer | clinical sample |
| bladder | Ambion 7990 | 81P0101A | colorectal cancer | clinical sample |
| bone marrow | Clontech64106-1 | 1110932 | colorectal cancer | clinical sample |
| peripheral mononuclear blood cell | clinical sample | — | colorectal cancer | clinical sample |
| testis | Clontech64027-1 | 6120257 | colorectal cancer | clinical sample |
| prostate | Ambion 7988 | 081P0103A | colorectal cancer | clinical sample |
| ovary | Ambion 7974 | 051P42A | colorectal cancer | clinical sample |
| uterus | Stratagene 735042 | 1100640 | colorectal cancer-liver metastasis | clinical sample |
| placenta | Ambion 7950 | 061P33B | colorectal cancer-liver metastasis | clinical sample |
| hepatic cirrhosis | clinical sample | — | colorectal cancer-liver metastasis | clinical sample |
| embryo brain | Clontech64094-1 | 2020902 | colorectal cancer-liver metastasis | clinical sample |
| embryo liver | CHEMICON356 | 21060678 | colorectal cancer-liver metastasis | clinical sample |
| | | | colorectal cancer-liver metastasis | clinical sample |
| | | | colorectal cancer-liver metastasis | clinical sample |
| | | | colorectal cancer | clinical sample |
| | | | colorectal cancer | clinical sample |
| | | | pancreas cancer | clinical sample |
| | | | pancreas cancer | clinical sample |
| | | | pancreas cancer | clinical sample |
| | | | pancreas cancer | clinical sample |

| Tissue | Number of Cases | Tumor | Cell line | Medium | Serum (%) |
|---|---|---|---|---|---|
| whole brain | 3 | brain tumor | U251 | DMEM | 10 |
| tonsil | 12 | breast cancer | MCF7 | RPMI1640 | 10 |
| callosal body | 3 | esophageal cancer | TE2 | RPMI1640 | 10 |
| caudate nucleus | 3 | stomach cancer | AGS | RPMI1640 | 10 |
| thalamus | 3 | | GT3 | DMEM | 10 |
| hippocampus | 1 | | Kato[I] | RPMI1640:DMEM = 1:1 | 10 |
| pituitary gland | 1 | | MKN45 | RPMI1640 | 10 |
| cerebellum | 1 | | MKN74 | RPMI1640 | 10 |
| thyroid gland | 1 | | 2M | DMEM | 10 |
| salivary gland | 1 | | 2MD3 | DMEM | 10 |
| lung | 1 | colorectal cancer | CACO2 | DMEM | 20 |
| trachea | 1 | | DLD1 | RPMI1640 | 10 |
| skeletal muscle | 1 | | hCT116 | McCoy5A | 10 |
| heart | 1 | | LOVO | HamF12:DMEM = 1:1 | 10 |
| kidney | 1 | | SW480 | RPMI1640 | 10 |
| adrenal gland | 1 | hepatic cancer | Alexander | DMEM | 10 |
| liver | 1 | | HepG2 | DMEM | 10 |
| pancreas | 1 | | HLE | DMEM | 10 |
| spleen | 1 | | HuH6 | DMEM | 10 |
| stomach | 1 | | HuH7 | DMEM | 10 |
| small intestine | 1 | pancreas cancer | Capan1 | DMEM | 20 |
| large intestine | 1 | | KLM1 | RPMI1640 | 10 |
| bladder | 1 | | Panc1 | RPMI1640 | 10 |
| bone marrow | 1 | | Paca2 | RPMI1640 | 10 |
| peripheral mononuclear blood cell | 1 | kidney cancer | Caki2 | RPMI1640 | 10 |
| testis | 1 | lung cancer | A549 | DMEM | 10 |
| prostate | 1 | | Lu130 | RPMI1640 | 10 |
| ovary | 1 | | H1359 | RPMI1640 | 10 |
| uterus | 1 | | H157 | RPMI1640 | 10 |
| placenta | 1 | | H1648 | HamF12:DMEM = 1:1 | 10 |
| hepatic cirrhosis | 1 | | H2009 | HamF12:DMEM = 1:1 | 10 |
| embryo brain | 1 | | H23 | RPMI1640 | 10 |
| embryo liver | 1 | | H2347 | RPMI1640 | 10 |
| | 1 | | H522 | RPMI1640 | 10 |
| | 1 | cervix cancer | Hela | DMEM | 10 |
| | 1 | | | | |
| | 1 | | | | |
| | 1 | | | | |

TABLE 1-continued

Tissues and cell lines used for the ROBO1 gene expression analysis 1
1
1

Gene expression analysis was carried out using 10 ng each of total RNAs, subjecting to GeneChip U133 (manufactured by Affymetrix) according to the Expression Analysis Technique Manual (manufactured by Affymetrix). Genes overexpressed in cancer cells was searched based on the mean value of the expression score set at 100 for total gene, it was apparent that expression was notably enhanced for ROBO1 mRNA (Probe ID: 213194_at HG-U133A), by 26-fold in moderately-differentiated hepatocellular cancer (236.4), and by 62-fold in poorly-differentiated hepatocellular cancer (563), compared to healthy liver (9.1). In addition, the expression of ROBO1 mRNA was also enhanced in large intestine cancer, with a two-fold enhancement or more in five out of eight cases in primary large intestine cancer, compared to healthy large intestine (21.4). In addition, enhancement was also marked in three out of seven cases in metastasizing hepatic cancer of large intestine cancer, compared to healthy liver and large intestine. One case where ROBO1 was enhanced two-fold or more compared to healthy lung was also present in pulmonary parvicellular cancer (FIG. 1a,b).

In the analyses in cancer cell lines, expression of ROBO1 showed a score of 100 in U251, which is a cell line derived from human brain tumor, Alexander, HLE, HuH6, HuH7 and HepG2, which are derived from a human hepatic cancer cell line, Lu1320 and H522, which are derived from a human lung cancer cell line, and Hela, which is derived from human uterine cervical cancer, and the like, suggesting that expression of ROBO1 is stimulated not only in hepatocellular cancer, large intestine cancer and lung cancer shown above, but also in a wide range of cancers such as brain tumor and uterine cervical cancer (FIG. 1c).

In addition, analyses were carried out in the same way as described above in well-differentiated, moderately-differentiated (attributed to HBV or HCV viral infection) and poorly-differentiated hepatocellular cancer for hepatocellular cancers, as well as for hepatitis site, hepatic cirrhosis site, which are non-cancer sites, and healthy liver, using GeneChip™ HG-U95B Target (manufactured by Affymetryx). Total RNA was prepared from extracted tissues each from three cases, and 5 µg each of total RNA from three cases were mixed and subjected to the GeneChip analysis. The values are shown with the mean value of the total chip score normalized to 100.

Figure 2:
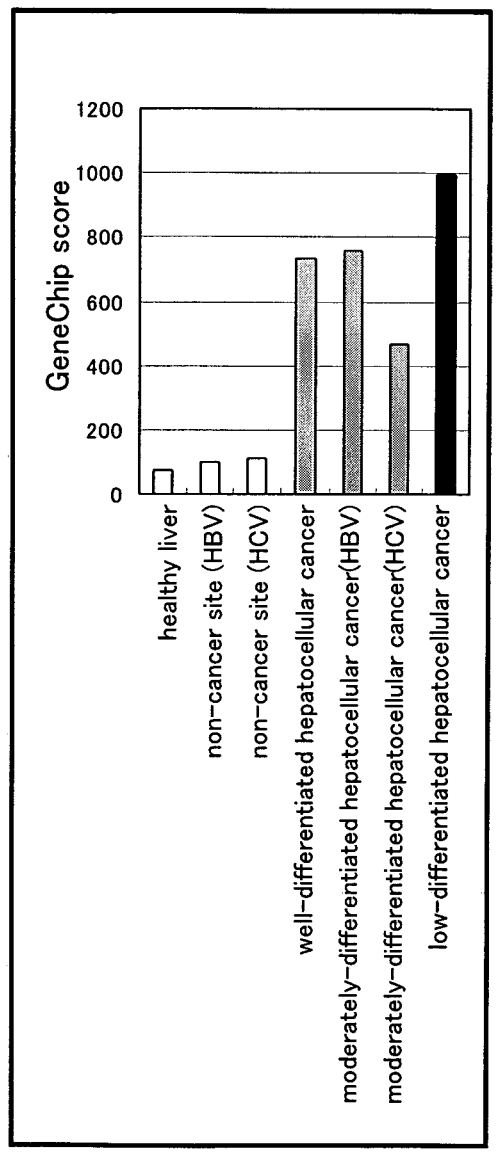
FIG. 2 shows the results of ROBO1 gene expression analysis using GeneChip U95.

As a result, the ROBO1 gene (Probe ID: 55461_at_HG-U95B) was expressed in an extremely low amount in healthy liver and non-cancer sites, while a remarkable increase in expression was observed in from well-differentiated hepatocellular cancer to poorly-differentiated hepatocellular cancer. It clearly shows that the expression was enhanced in hepatocellular cancer (FIG. 2).

Example 2

1-2. ROBO1 mRNA Expression Analysis by Quantitative PCR

Quantitative PCR was carried out using RNA prepared from healthy liver, hepatitis site, and hepatic cirrhosis site, as well as from tissue extirpated from hepatic cancer and from non-cancer site from the same tissue. PCR reaction was carried out with the iCycleriQ real time PCR analysis system (manufactured by BIO-RAD) using as the template DNA a single-stranded cDNA synthesized using the reverse transcriptase Superscript II (manufactured by GIBCO BRL) from the total RNA prepared from each tissue, to quantify the amount of expression of mRNA expression. The primer for ROBO1 was designed according to GenBank ID (NM_133631). Each 25 µL PCR reaction solution was prepared to contain 500 mM KCl, 100 mM Tris-HCl (pH8.3), 20 mM $MgCl_2$, 0.1% gelatine, 1.25 mM dNTPs (dATP, dCTP, dGTP, dTTP) each, 1 µL of each single-stranded cDNA, 5 pmol each of ROBO1 sense primer (SEQ ID NO: 1) and ROBO1 antisense primer (SEQ ID NO: 2), 0.75 µL of SYBR Green I (1000-fold diluted solution, manufactured by Takara Shuzo), 0.25 µL of recombinant Taq polymerase Mix (FG Pluthero, Rapid purification of high-activity Taq DNA polymerase, Nucl. Acids. Res. 1993 21: 4850-4851.). The reaction comprised of a primary denaturation for 3 minutes at 94° C., and 40 cycles of 15 seconds at 94° C., 15 seconds at 63° C., and 30 seconds at 72° C. The amount expressed in each authentic preparation was calculated using the software associated with the iCycler iQ real time analysis system. In addition, the amount of human β-actin gene expressed in individual RNA was also analyzed in the same way as described above using a sense primer (SEQ ID NO: 3) and an antisense primer (SEQ ID NO: 4) specific to human β-actin. The analysis result of ROBO1 was corrected with the analysis result of human β-actin (ROBO1/β-actin×100) and served as the amount of ROBO1 mRNA expressed.

As a result, similarly to the result from the GeneChip analysis, expression of ROBO1 mRNA was almost not observed in healthy liver and hepatitis site, as well as hepatic cirrhosis site; in contrast, the expression of ROBO1 mRNA was observed to be enhanced in a number of hepatocellular cancer sites. In particular, in comparisons of cancer site and non-cancer site within the same tissue, the expression was enhanced two-fold or more in 8 cases out of the 9 cases analyzed (Table 2).

TABLE 2

Rate of enhancement of ROBO1 gene expression by quantitative PCR analysis
Quantitative PCR analysis (versus beta-actin (%))

| Patient No. | Stage | Non-cancer site | Cancer Site | Expression increase rate |
|---|---|---|---|---|
| #1 | moderately-differentiated | 16 | 712 | 44.5 |
| #12 | moderately-differentiated | 62 | 488 | 7.9 |
| #15 | moderately-differentiated | 19 | 40 | 2.1 |
| #21 | moderately-differentiated | 19 | 64 | 3.4 |
| #30 | moderately-differentiated | 46 | 118 | 2.6 |
| #22 | poorly-differentiated | 16 | 304 | 19.0 |
| #104 | poorly-differentiated | N/A | 826 | |

TABLE 2-continued

Rate of enhancement of ROBO1 gene expression by
quantitative PCR analysis
Quantitative PCR analysis (versus beta-actin (%))

| Patient No. | Stage | Non-cancer site | Cancer Site | Expression increase rate |
|---|---|---|---|---|
| #108 | poorly-differentiated | 15 | 32 | 2.1 |
| #111 | poorly-differentiated | 161 | 43 | 0.3 |
| #115 | poorly-differentiated | 154 | 685 | 4.4 |
| | Pair with a difference of two-fold or more: | | 8 cases | |

Example 3

Preparation of Anti-ROBO1 Antibody

In order to test the possibility of detecting cancer using an anti-ROBO1 antibody, an anti-ROBO1 antibody was generated.

3-1. Preparation of Antigen 3-1-1. Isolation of ROBO1 cDNA

In order to carry out expression of ROBO1, a ROBO1 cDNA was first isolated as follows. A single stranded cDNA was prepared from Hep3B cell following the method described above, and used as a template in amplification by the PCR method using primer RBV2F-TA (SEQ ID NO: 5) and RBR-TA (SEQ ID NO: 6). Primer RBV2F-TA was designed to hybridize with the 5'-end of the ROBO1 gene (GenBank: NM_133631), and RBR-TA was designed to hybridize to the 3'-end. The PCR method was carried out by preparing the reaction solution according to protocols of the LA-PCR kit (TAKARA manufactured by), and comprised of a primary denaturation for two minutes at 95° C., and 30 cycles of 15 seconds at 94° C., 15 seconds at 63° C., and 5 minutes at 72° C., and then the last elongation reaction under conditions comprising 10 minutes at 72° C. As a result, a band near approximately 5 kbp corresponding to the predicted ROBO1 sequence was successfully detected. The specifically amplified fragment obtained by the PCR method was inserted into pcDNA3.1/V5-His TOPO (manufactured by Invitrogen) by the TA cloning method. The base sequence was examined by an established method to confirm that the isolated cDNA corresponded to ROBO1.

3-1-2. Preparation of Recombinant Baculovirus Expressing the N-Terminal Site of ROBO1

A region containing from the N-terminus to the first immuno globulin region (Ig1) of ROBO1 was expressed as a fusion protein with the membrane protein gp64 of the baculovirus with the ROBO1 cDNA isolated above as a template, the gene coding for the region containing from the N-terminus to the first immuno globulin region (Ig1) of ROBO1 was amplified by the PCR method using the RB_BVF primer (SEQ ID NO: 7) and the RB_BVR primer (SEQ ID NO: 8), and inserted into the pGEM-Te vector (manufactured by Promega). After verifying the base sequence by an established method, a gene fragment was digested with the restriction endonuclease KpnI and inserted into the pBucSurf vector (manufactured by Novagen) to construct a transfer vector ROBO1N/pBS. Then, 4 μg of ROBO1N/pBS was cut using the restriction endonuclease BplI (manufactured by Fermentas) and linearized and introduced together with Bac-N-Blue DNA into Sf9 cell according to the instructions of Invitrogen to prepare a recombinant baculovirus expressing a fusion protein of ROBO1-Ig1 and gp64.

The recombinant virus prepared as above was added to infect Sf9 cells ($2\times10^6$ cells/mL) at the MOI of 5, which were then cultured at 27° C. for 3 days. Budding baculoviruses (BV) expressing the fusion protein of ROBO1-Ig1 and gp64 were recovered from the culture supernatant after 3 days culture. The culture solution was centrifuged at 800×g for 15 minutes to remove cells and cell debris, then the recovered culture supernatant was centrifuged at 45,000×g for 30 minutes. The precipitate was resuspended in PBS, and cell components were removed by further centrifuging at 800×g. The supernatant was centrifuged again at 45,000×g, and the obtained precipitate was suspended with PBS to serve as the BV fraction to be used as antigen for immunization.

3-2. Preparation of Anti-ROBO1 Monoclonal Antibody

An anti-ROBO1 monoclonal antibody was generated using as antigen the ROBO1-Ig1 expressing BV prepared by the above method. ROBO1-Ig1 expressing BV corresponding to a protein amount of 1 mg suspended in PBS were mixed with 200 ng of pertussis toxin, and subcutaneously injected into a gp64 transgenic mouse (WO03/104453) as an initial immunization. In a subsequent immunization, only ROBO1-Ig1 expressing BV corresponding to a protein amount of 500 μg was injected subcutaneously. As a final immunization, 250 μg of ROBO1-Ig1 expressing BV was administered intravascularly. After 3 days, spleen cells were isolated from the mouse, and fused with mouse P3U1 cells by a conventional method to establish a hybridoma cell. A hybridoma cell producing anti-ROBO1 antibody was selected by ELISA, in which the antigen ROBO1-Ig1 expressing BV used for immunization was immobilized on a solid phase. For the ELISA method, ROBO1-Ig1 expressing BV was left for one day and night in a 96-well flat-bottomed plate (manufactured by Falcon) at 4° C. at a final concentration of 10 μg/ml, then blocked with TBS buffer solution containing 40% Block Ace reagent (manufactured by Dainippon Pharmaceutical Co., Ltd.). A hybridoma culture supernatant was added, and the reaction was let to take place at room temperature for one hour. Next, HRP labeled antimouse IgG antibody (manufactured by Jackson) was added at room temperature for 1 hour, washed 4 times, then 3,3',5,5'-tetramethylbenzin (TMB) reagent (manufactured by Sigma) was added at room temperature for one hour. The reaction was stopped with 0.5N sulfuric acid, and the optical density at 492 nm was measured with the microplate reader Multickan JX (manufactured by Labsystems).

As a result, hybridoma cells A7241A and A7225A were successfully established which produce a monoclonal antibody that binds to ROBO1. Each monoclonal antibody was prepared from the culture supernatant of the hybridoma cells by ammonium sulfate precipitation.

Example 4

Detection of ROBO1 Protein Molecule Using Anti-ROBO1 Antibody

In order to test the reactivity of the anti-ROBO1 antibody prepared by the above description, ROBO1 was detected using cell lysates from cell lines overexpressing ROBO1 and from various cancer cell lines. First, reactivity of the anti-ROBO1 antibody A7241A was verified by Western analysis using HEK293 cells forced to express ROBO1. The full length ROBO1 gene expression vector (ROBO1/pcDNA3.1) containing cDNA coding for ROBO1 inserted into pcDNA3.1/V5-H is TOPO (manufactured by Invitrogen) was used as an animal cell expression vector. Next, 1 μg of ROBO1/psDNA3.1 or pcDNA3.1 (Mock) as a negative control was introduced into 5×10⁴ COS7 cells or 2×10⁵ HEK293 cells using the FuGene6 reagent (manufactured by Roche Diagnostics), to express ROBO1 transiently. Cells were recovered three days after introduction of the expression vector, and the cultured cells were solubilized in the RIPA buffer solution (150 mM sodium chloride, 1% NP-40, 0.5% deoxycholic acid, 0.1% SDS, 50 mM tris-hydroxymethyl-aminomethane hydroxy aminomethane hydrochloride (pH 8.0)) to prepare a cell lysate.

Figure 3:
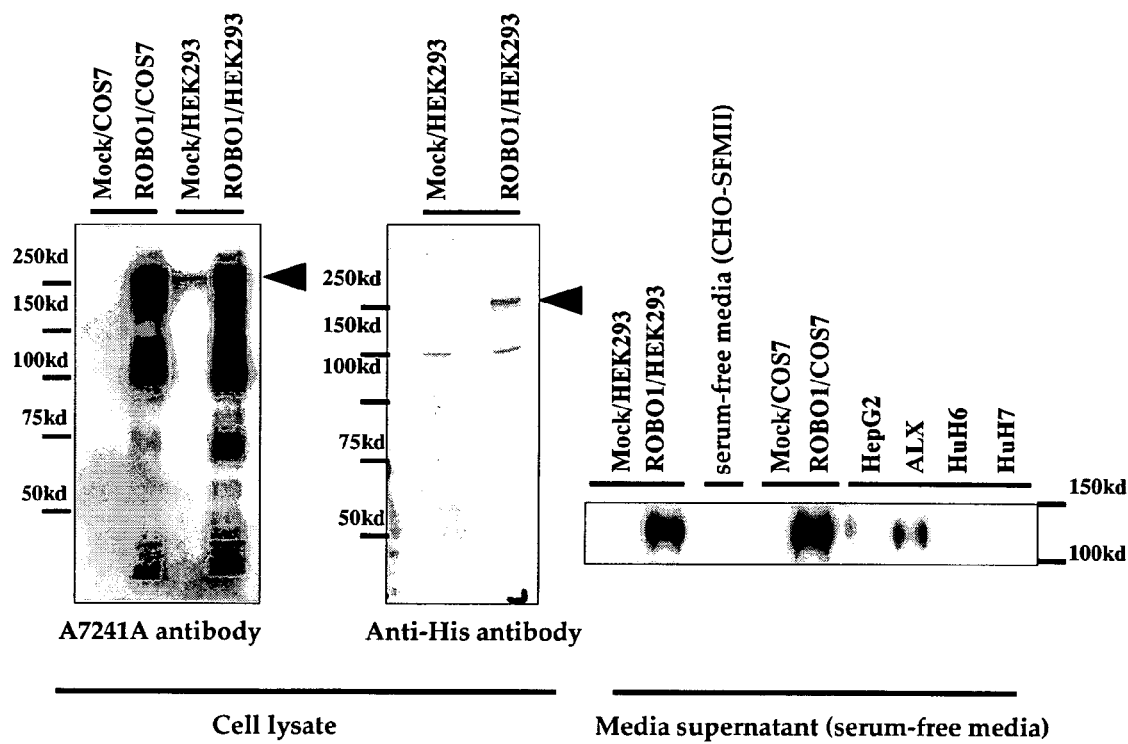
FIG. 3 shows the results of Western analysis of transient expression of full length ROBO1 gene in COS7 cell and HEK293 cell lysates, and the results of Western analysis in the supernatant of the culture thereof.

An amount corresponding to 3 µg of protein of each lysate was subjected to SDS-polyacrylamide gel. The proteins were separated by SDS-PAGE and transferred to Hybond-P (manufactured by Amersham Bioscience). Then, the protein was detected with ECL plus (manufactured by Amersham Bioscience) using an anti-H is antibody (manufactured by Sigma) or the A7241A antibody (1 µg/mL) as primary antibody, and using HRP labeled antimouse IgG antibody (manufactured by Jackson) as secondary antibody. A band of approximately 260 kD molecular weight reacting specifically with the anti-H is antibody was detected. This band was considered as the full length ROBO1. A band with the same molecular weight was also observed in the cell lysate using the anti-ROBO1 antibody A7241A. From the above results, the anti-ROBO1 antibody A7241A was shown to be capable of detecting a full length ROBO1 protein specifically. A few bands with small molecular weights were also detected for A7241A, but not detected with the anti-H is antibody, suggesting that they are degradation products lacking the C-terminus. Indeed, a band of approximately 120 kD molecular weight was detected in the culture supernatant (FIG. 3). Although the estimated molecular weight of full length ROBO1 is 190 kD, it was detected at a higher position (approximately 260 kD) than 250 kD of the prestained molecular weight markers (manufactured by Bio-Rad), probably due to modification of glycosyl chain. In addition, a band thought to be ROBO1 was also detected in the Mock test using HEK293 cell and pcDNA3.1. ROBO1 is thought to be expressed in HKE293 cells, which were derived from human embryo kidney, since ROBO1 is expressed during the fetal stage.

Figure 4:
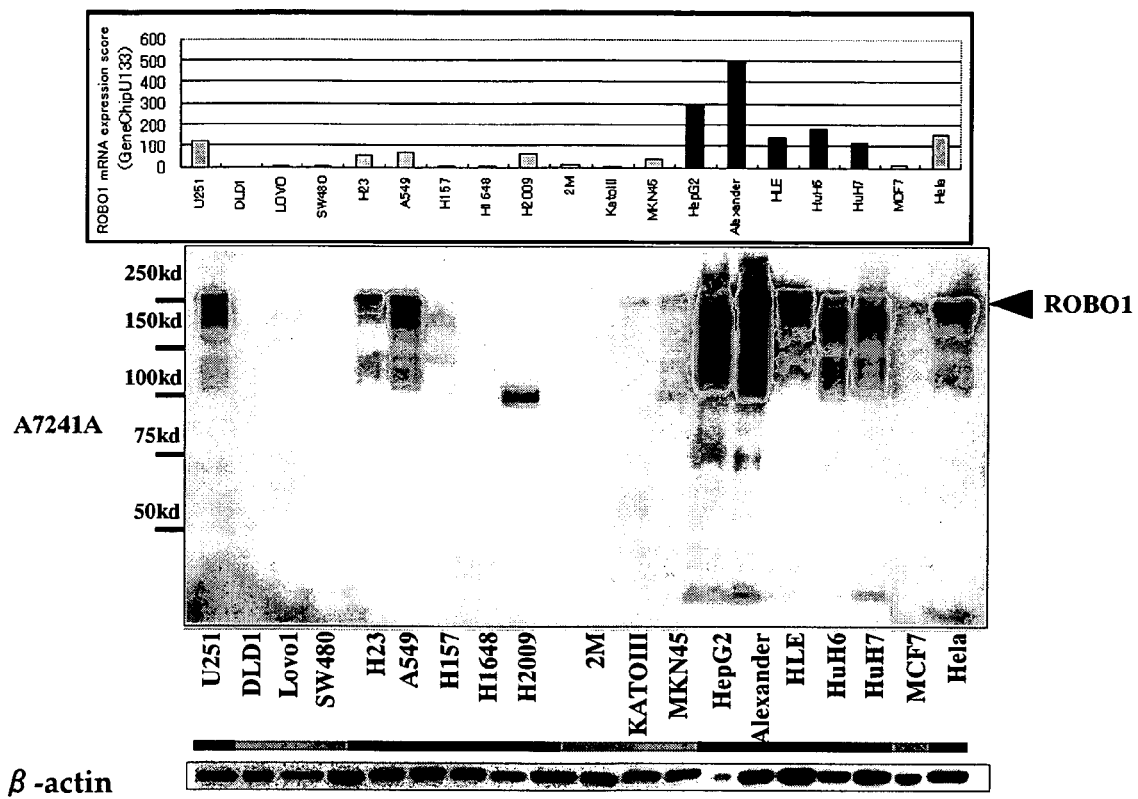
FIG. 4 shows the results of Western analysis of the hepatic cancer cell line lysate using anti-ROBO1 monoclonal antibody A7241A.

Next, Western analysis was carried out for cell lysates from various cancer cell lines. As a result, a band of approximately 260 kD molecular weight thought to be the full length ROBO1 was detected successfully only in the cell lines with a high mRNA expression score, which is consistent with the GeneChip U133 analysis results (FIG. 4). In addition, a plurality of bands with small molecular weights were detected in the same way, suggesting that, depending on the cell line, the number of links in a glycosyl chain is different, or ROBO1 with different molecular weights are present due to degradation or splicing.

It was examined whether soluble ROBO1 fragment can be detected in the culture supernatant of cancer cell lines expressing ROBO1. In the culture supernatant of a hepatic cancer cell line highly expressing ROBO1, a band with the same molecular weight as the culture supernatant of the overexpressing cells was also detected by the anti-ROBO1 antibody (FIG. 3).

From the above result, it was clear that the ROBO1 monoclonal antibody A7241A can specifically detect ROBO1, and that the degree of mRNA expression by the GeneChip analysis was consistent with the degree of ROBO1 protein expression. In addition, the examination using anti-ROBO1 antibody clearly showed that soluble ROBO1 fragment was present in the culture supernatant of ROBO1 expressing cell, strongly suggesting that the presence or the absence of cancer cell can be determined by detecting soluble ROBO1.

Example 5

Immunohistological Staining of Hepatocellular Cancer Tissue

Immunohistological staining analysis of clinical sample of hepatocellular cancer was carried out using anti-ROBO1 monoclonal antibody.

A section from a fixed paraffin embedded preparation of a hepatocellular cancer extirpated tissue sliced to 4 µm was mounted on a slide glass, and left at 37° C. for about 16 hours to dry extensively. The slide glass was deparaffinized by soaking three times in 100% xylene for 5 minutes each, then hydrophylized by soaking three times in 100% alcohol for 5 minutes and in 70% ethanol for 5 minutes. Then, after washing three times in 50 mM TBS buffer solution (50 mM Tris, pH 7.4, 150 mM NaCl) for 5 minutes, the antigen was activated by reacting in a citrate buffer (10 mM, pH 7.0) at 120° C. for 10 minutes. Following the activation of the antigen, the slide glass washed with a TBS buffer solution three times for 5 minutes each. Then, A7241A antibody diluted to 10 µg/mL was reacted at room temperature for one hour. Next, the endogenous peroxidase was inactivated with 0.3% hydrogen peroxide for 15 minutes at room temperature. After washing three more times with a TBS buffer solution, ENVISION+ kit/HRP (manufactured by DAKO) was added as the secondary antibody for one hour. After washing three times with TBS buffer solution for 5 minutes each, DAB (3,3'-diaminobenzidine tetrahydrochloride) was added for color development. Hematoxylin was used for contrast staining of the nucleus.

Figure 5:
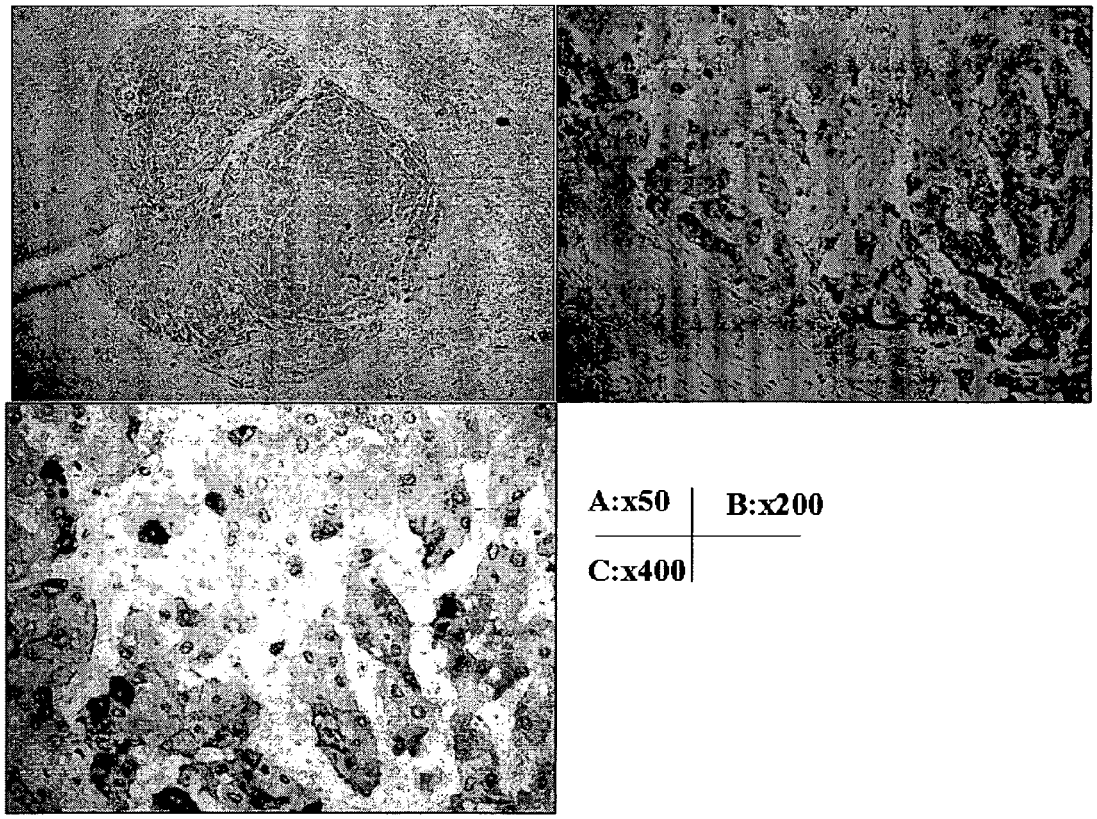
FIG. 5 shows the results of immunohistological staining analysis of hepatocellular cancer paraffin preparations using anti-ROBO1 monoclonal antibody A7241A.

As a result, as shown in FIG. 5, hepatocellular cancer tissue was stained specifically by the anti-ROBO1 antibody, indicating that the expression of ROBO1 protein was specifically stimulated in hepatocellular cancer. In addition, the anti-ROBO1 antibody was shown to be useful for the immunohistochemical diagnosis of cancers highly expressing ROBO1, such as hepatocellular cancer.

Example 6

Figure 6:
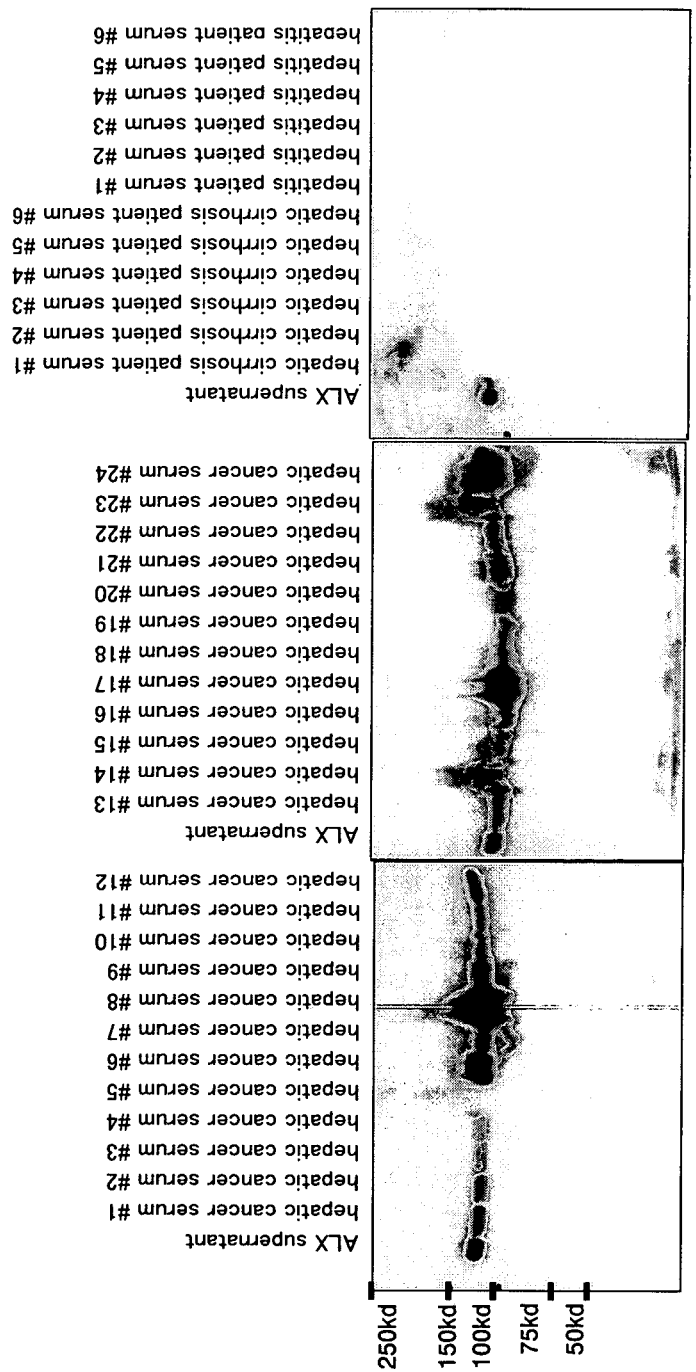
FIG. 6 shows the results of Western analysis of soluble ROBO1 in patient serum using anti-ROBO1 monoclonal antibody A7241A.

Detection of Soluble ROBO1 Protein (sROBO1) in the Serum of Hepatocellular Cancer Patient The results of Example 4 showed that a fragment of ROBO1 protein was released and existed as soluble ROBO1. From this fact, a soluble ROBO1 protein (sROBO1) is considered to be present in the serum of a patient with cancer expressing ROBO1 at a elevated level, such as a hepatocellular cancer, and is useful as a diagnosis marker. The presence of soluble ROBO1 in each serum from 24 hepatocellular cancer patients, 6 hepatic cirrhosis patients and 6 hepatitis patients was examined by a Western analysis using the A7241A antibody. The SDS-PAGE and the Western analysis were carried out as described above with 5 µl of each patient serum. The culture supernatant of the hepatic cancer cell line Alexander (ALX) was used as a positive control. As a result, as shown in FIG. 6, sROBO1 was detected in the serum of a hepatocellular cancer patient in 23 out of 24 cases, while it was not detected in the sera of hepatic cirrhosis and hepatitis patients. From these results, sROBO1 was shown to be present also in the serum of a patient with ROBO1-expressing cancer, and the detection of sROBO1 was shown to be extremely efficient as a serodiagnosis marker of ROBO1-expressing cancer, such as hepatocellular cancer.

27

Example 7

Preparation of Soluble ROBO1 (sROBO1-His)

A soluble ROBO1 with a His-tag added to the C-terminus of the extracellular region of ROBO1 (sROBO1-H is) was prepared as described below.

The gene coding for the extracellular region was amplified by the PCR method with ROBO1 cDNA as a template and using the primer RBV2F-TA (SEQ ID NO: 13) and the primer RB_SH_TA (SEQ ID NO: 14). The PCR product was directly inserted into the pBlueBack4.5-TOPO vector and the sequence was analyzed to generate a transfer vector sROBO1/pBB having the correct base sequence. A recombinant baculovirus was prepared using 4 µg of sROBO1/pBB by a similar method to Example 3.

Next, sROBO1-H is was prepared as described below. $2 \times 10^6$/mL of Sf9 cells were infected with the sROBO1-H is expressing recombinant baculovirus at an MOI of 5, cultured for 3 days at 27° C., and the culture supernatant was recovered. sROBO1-H is contained in the culture supernatant was purified using Ni-NTA superflow (QIAGEN) according to the enclosed protocol. The purification product was concentrated using Centircon-10 (manufactured by Amicon), and the buffer was exchanged to PBS to prepare sROBO1-His.

Example 8

Evaluation of Serum from sROBO1-Immunized Rabbit 8-1. Detection of ROBO1 Protein Molecule by Western Analysis The purified sROBO1 antigen (100 µg/0.5 mL/animal) suspended in PBS was mixed with 0.5 mL of Freund complete adjuvant (manufactured by DIFCO) to form an emulsion, and administered by subcutaneous injection to New Zealand White rabbits (10 weeks old females, manufactured by Clea Japan) as an initial immunization. Subsequently, with an interval of 2 weeks, a total of four immunizations were carried out by subcutaneous injections of an emulsion containing 100 µL/0.5 mL of purified sROBO1 antigen suspended in PBS mixed with 0.5 mL of Freund complete adjuvant. Blood was collected prior to immunization and after the third and the fourth immunization, and the increase in the levels of the antibody against sROBO1 was determined by the ELISA method. sROBO1 was immobilized on a solid phase onto an ELISA polystyrene plate, and a series of dilution of rabbit antiserum was added to the plate. The plate was reacted with horseradish peroxidase labeled antirabbit IgG antibody (manufactured by Cappel) and colored with 3,3',5,5'-tetramethylbenzidine reagent (TMB reagent; manufactured by Cytech) to assay the antibody titer. After the increase in the antibody level was observed, whole blood was collected to obtain anti-ROBO1 rabbit antiserum.

Figure 7:
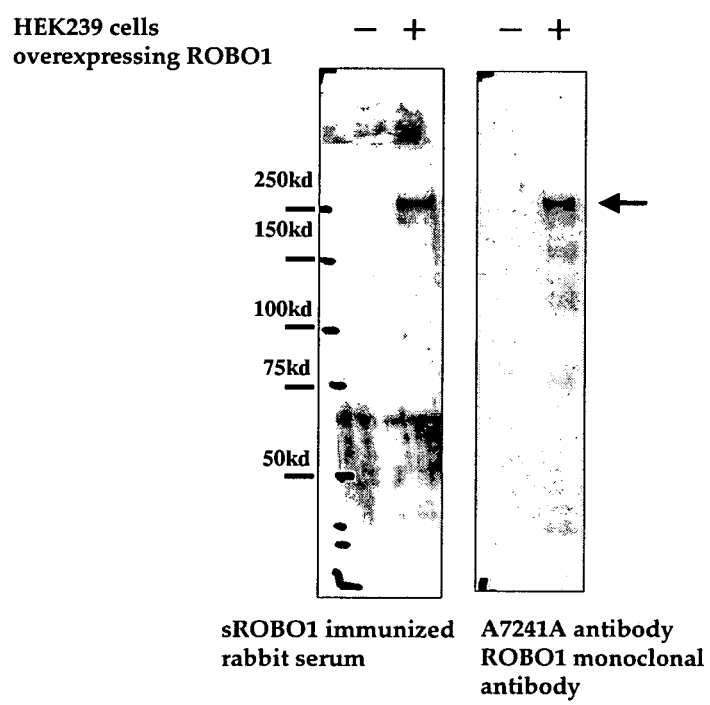
FIG. 7 shows the results of Western analysis of lysate of HEK293 cell forced to express the full length ROBO1 gene using sROBO1-immunized rabbit serum.

The full length ROBO1 molecule was detected by Western analysis using the serum from sROBO1 immunized rabbit. Cell lysate was prepared from HEK293 cell overexpressing a full length ROBO1 using RIPA buffer solution as described above, and an amount corresponding to 10 µg of protein was subjected to SDS-polyacrylamide gel. The proteins were separated and transferred to Hybond-P (manufactured by Amersham Bioscience). Then, the proteins were detected with ECL plus (manufactured by Amersham Bioscience) using a 100-fold diluted serum from sROBO1 immunized rabbit as primary antibody, and using HRP labeled antirabbit IgG antibody (manufactured by Amersham Bioscience) as secondary antibody. A band of approximately 260 kD molecular weight thought to be the full length ROBO1 molecule was detected, which was similarly to the positive control A7241A antibody (FIG. 7). From the above results, the serum from an sROBO1 immunized rabbit was shown to be capable of detecting the full length ROBO1 molecule by the Western analysis.

8-2. Detection of ROBO1 Protein by FACS Analysis

In order to evaluate whether serum from sROBO1 immunized rabbit could detect ROBO1 on the cell surface, FACS analysis was carried out using HEK293 cells forced to express ROBO1. HEK293 cells forced to express ROBO1 or negative control HEK293 cells were suspended in a FACS solution (PBS containing 1% albumin and 0.1% $NaN_3$). Serum from sROBO1 immunized rabbit was added to the cell suspension and let to react at 4° C. for 60 minutes. After washing twice with a FACS solution, FITC labeled antirabbit $F(ab)_2$ antibody (manufactured by DAKO) was added and let to react at 4° C. for 30 minutes. Then, the cells were washed twice with a FACS solution and analyzed by FACS with FACScalibur (manufactured by Beckton Dickinson) following the user manual. The anti-V5-tag antibody (manufactured by Invitrogen) was used as the positive control for the experiment, and the FITC labeled antimouse IgG antibody (manufactured by Jackson) was used as the secondary antibody. Since V5-tag was conjugated to the C terminus of the intracellular region of ROBO1, a FACS solution containing 0.1% saponin was used when the primary antibody was used, so that the antibody can detect the intracellular V5-tag.

Figure 8:
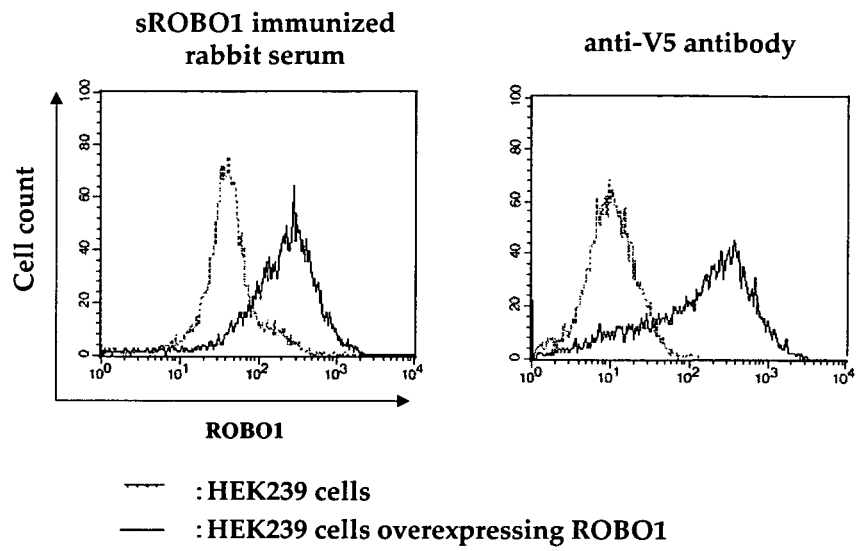
FIG. 8 shows the results of FACS analysis of lysate of HEK293 cell forced to express the full length ROBO1 gene using sROBO1-immunized rabbit serum.

The result is shown in FIG. 8. Similarly to the peak shift of the positive control anti-V5 antibody, a specific peak shift was also detected in the blood of sROBO1-immunized rabbit only in HEK293 cell forced to express ROBO1.

Figure 9:
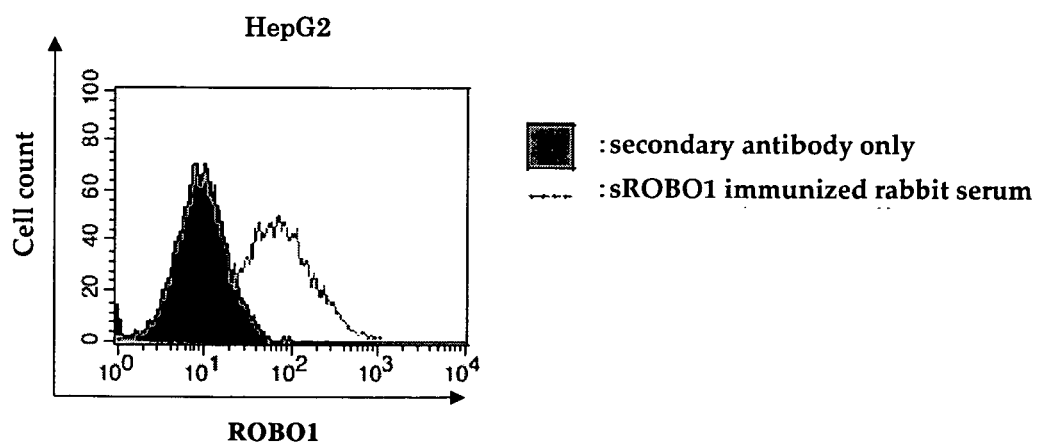
FIG. 9 shows the results of FACS analysis of lysate of HepG2 cell using sROBO1-immunized rabbit serum.

In addition, FACS analysis was carried out according to the same method as described above in hepatic cancer cell line HepG2 cells, which inherently express ROBO1, as shown in FIG. 9. A specific peak shift was observed in the serum of sROBO1 immunized rabbit, showing that ROBO1 molecule having the original structure on the cell surface could also be detected.

Example 9

Purification of Rabbit Anti-Human ROBO1 Polyclonal Antibody

Anti-human ROBO1 rabbit polyclonal antibody prepared from serum of sROBO1 immunized rabbit was purified by affinity chromatography with solid-phased ROBO1. A sROBO1-H is affinity column was prepared using CNBr-Activated Sepharose 4B (Amersham Pharmacia Biotech #17-0430-02) according to the enclosed text, and immobilizing 0.7 mg of purified sROBO1-H is antigen per 1 mL of gel, according to the enclosed documentation. Then, anti-ROBO1 rabbit polyclonal antibody was purified according to conventional methods from the rabbit serum obtained in Example 8.

Example 10

Establishment of ROBO1 Measurement System and Detection of ROBO1 in Blood by ELISA An ELISA detection system was constructed using the anti-ROBO1 rabbit polyclonal antibody obtained in Example 9. Anti-ROBO1 rabbit polyclonal antibody was diluted in PBS at a concentration of 5 µg/mL, and was dispensed into a 96-well immuno-plate, 50 µL per well each. After the plate was let to stand overnight at 2 to 8° C., the plate washed three times with PBS containing 0.05% Tween 20, and coated with 150 µL Immunoassay Stabilizer (ABI #10-601-001) per well for one hour. After the solution was discarded, the plate was dried at 37° C. for two hours to obtain a solid-phased anti- ROBO1 antibody plate. For the biotinylated anti-ROBO1 antibody used for detection, anti-ROBO1 rabbit polyclonal antibody and Sulfo-NHS-LC-Biotin (Pierce #21335) were prepared at 0.12 mg/mL and 46 µg/mL, respectively, using a 50 mM carbonate buffer solution at pH 8.5, and let to stand at room temperature for two hours. Unreacted biotin reagent was removed using PD-10 (Pharmacia #17-0851-01), and biotinylated anti-ROBO1 antibody was diluted to 1 µg/mL with PBS containing 30% calf serum. Biotinylated anti-ROBO1 antibody was detected using streptavidin labeled peroxidase (Vector #SA-5004) diluted at 3 µg/mL in tris-hydroxymethyl-aminomethane buffered physiological saline containing 30% calf serum. TMB reagent (Cytech #TM490041) was used as the substrate for peroxidase and TMB stop agent (Cytech #TSB999) was used as stop reagent for the substrate reaction.

ROBO1 concentration was measured in the sera from 72 cases of healthy subjects, 79 cases of hepatic cancer patients, 67 cases of hepatic cirrhosis/chronic hepatitis patients and 22 cases of other cancer patients. Purified sROBO1-H is was used as a standard for measuring ROBO1 concentrations. Serum or sROBO1-H is was diluted to 1/90 fold with tris-hydroxymethyl-aminomethane buffer solution containing 20% rabbit serum and 1% BSA, respectively, and 100 µL each was dispensed into each well of the antibody solid phased plate. After incubating at room temperature for two hours, 25 µL of biotinylated anti-ROBO1 antibody was dispensed into each well. After incubating at room temperature for two hours, the reaction solution was removed from the well, 100 µL each of streptavidin labeled peroxidase reagent was dispensed. After incubating at room temperature for 30 minutes, the plate was washed 5 times with PBS containing 0.05% Tween 20. 100 µL each of TMB reagent was added to each well, and incubated at room temperature for 30 minutes. 100 µL of TMB stop reagent was added, and the absorption at a wavelength of 450 nm was measured with an EIA plate reader (Corona Electric Co., #MTP-120) with a reference wavelength of 630 nm.

Figure 10:
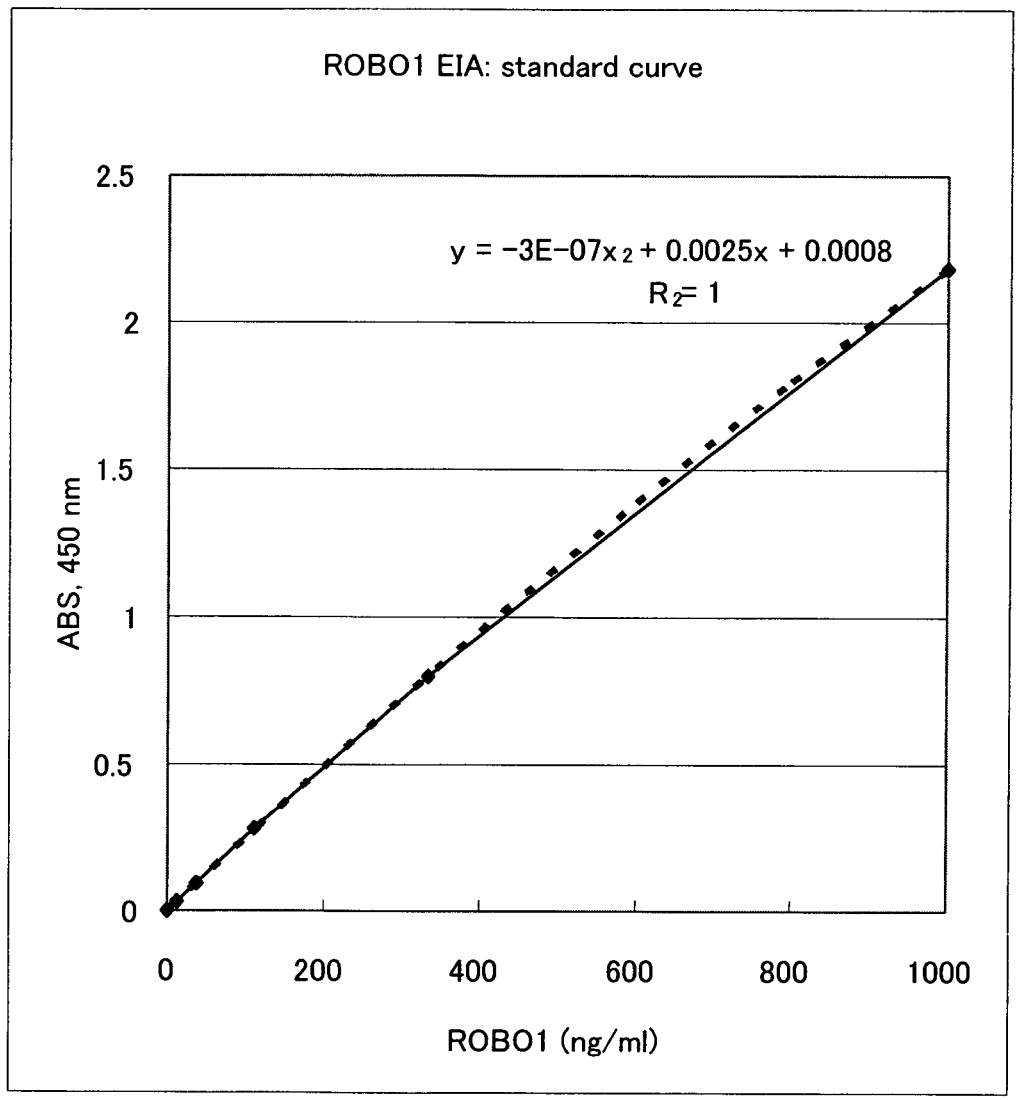
FIG. 10 shows a standard curve for ROBO1 measurement by enzyme immunoassay using rabbit anti-sROBO1 antibody.

As a result, a concentration-dependent increase of absorption was observed with sROBO1-His. The concentration in each serum was determined by regression to the standard absorption curve (FIG. 10). The results are shown in Tables 3, 4, 5 and 6.

TABLE 3

Concentration of ROBO1 in blood of healthy subjects

| | ID NO. | ROBO1 (ng/ml) |
|---|---|---|
| 1 | 1210 | 44 |
| 2 | 1211 | 44 |
| 3 | 1212 | 37 |
| 4 | 1213 | 39 |
| 5 | 1214 | 56 |
| 6 | 1215 | 39 |
| 7 | 1216 | 41 |
| 8 | 1217 | 38 |
| 9 | 1218 | 33 |
| 10 | 1219 | 38 |
| 11 | 1220 | 42 |
| 12 | 1221 | 41 |
| 13 | 1222 | 33 |
| 14 | 1223 | 39 |
| 15 | 1224 | 30 |
| 16 | 1225 | 38 |
| 17 | 1226 | 30 |
| 18 | 1227 | 44 |
| 19 | 1228 | 36 |
| 20 | 1229 | 37 |
| 21 | 1230 | 43 |
| 22 | 1231 | 44 |
| 23 | 1232 | 38 |
| 24 | 1233 | 40 |
| 25 | 1234 | 22 |
| 26 | 1235 | 26 |
| 27 | 1236 | 35 |
| 28 | 1237 | 40 |
| 29 | 1238 | 41 |
| 30 | 1239 | 42 |
| 31 | 1240 | 36 |
| 32 | 1241 | 45 |
| 33 | 1242 | 19 |
| 34 | 1243 | 35 |
| 35 | 1244 | 39 |
| 36 | 1245 | 36 |
| 37 | 1246 | 36 |
| 38 | 1247 | 39 |
| 39 | 1248 | 42 |
| 40 | 1249 | 27 |
| 41 | 1250 | 34 |
| 42 | 1251 | 34 |
| 43 | 1252 | 29 |
| 44 | 1253 | 30 |
| 45 | 1254 | 33 |
| 46 | 1255 | 23 |
| 47 | 1256 | 15 |
| 48 | 1257 | 28 |
| 49 | 1258 | 39 |
| 50 | 1259 | 41 |
| 51 | 1260 | 40 |
| 52 | 1261 | 43 |
| 53 | 1262 | 35 |
| 54 | 1263 | 34 |
| 55 | 1264 | 36 |
| 56 | 1265 | 34 |
| 57 | 1266 | 22 |
| 58 | 1267 | 21 |
| 59 | 1268 | 35 |
| 60 | 1269 | 31 |
| 61 | 1270 | 29 |
| 62 | 1271 | 27 |
| 63 | 1272 | 33 |
| 64 | 1273 | 28 |
| 65 | 1274 | 29 |
| 66 | 1275 | 36 |
| 67 | 1276 | 47 |
| 68 | 1277 | 41 |
| 69 | 1278 | 33 |
| 70 | 1279 | 38 |
| 71 | 1280 | 33 |
| 72 | 1281 | 56 |
| Mean | | 36 |
| SD | | 8 |
| Mean + 3SD | | 58 |
| Mean + 6SD | | 81 |

TABLE 4

Concentration of ROBO1 in blood of hepatic cancer patients

| ID NO. | AFP (ng/ml) | PIVKA (U/ml) | AFP-L3 (%) | ROBO1 (ng/ml) |
|---|---|---|---|---|
| 1 | 428 | 2647 | 1292 | | 75 |
| 2 | 442 | 1976 | | 31.8 | 163 |
| 3 | 275 | 1670 | 130 | 79.4 | 152 |
| 4 | 538 | 168 | | | 226 |
| 5 | 229 | 146 | | 30.6 | 196 |
| 6 | 381 | 125 | 17 | 11.6 | 170 |
| 7 | 159 | 101 | 13 | | 143 |
| 8 | 168 | 82.7 | | 2.4 | 112 |

TABLE 4-continued

Concentration of ROBO1 in blood of hepatic cancer patients

| ID NO. | AFP (ng/ml) | PIVKA (U/ml) | AFP-L3 (%) | ROBO1 (ng/ml) |
|---|---|---|---|---|
| 9 | 545 | 73.3 | | 17.9 | 176 |
| 10 | 585 | 60.7 | 50 | 49.4 | 58 |
| 11 | 42 | 56.3 | 10 | 12.6 | 83 |
| 12 | 512 | 48.5 | 41 | 47.1 | 70 |
| 13 | 360 | 47.9 | 10 | 3.9 | 83 |
| 14 | 356 | 39 | 1565 | | 76 |
| 15 | 520 | 36.9 | 10 | 7.2 | 81 |
| 16 | 66 | 34 | 89 | | 139 |
| 17 | 337 | 32.5 | | 1.7 | 79 |
| 18 | 510 | 30.6 | | 1.5 | 92 |
| 19 | 322 | 30 | 1824 | | 83 |
| 20 | 225 | 29 | 19 | | 80 |
| 21 | 231 | 28 | | | 160 |
| 22 | 314 | 28 | — | 2.1 | 103 |
| 23 | 350 | 26 | 18 | | 98 |
| 24 | 402 | 25 | 2117 | | 80 |
| 25 | 289 | 22 | 10 | 7.8 | 107 |
| 26 | 549 | 21 | 893 | | 75 |
| 27 | 155 | 21 | 26 | 5.8 | 80 |
| 28 | 527 | 19 | 14 | | 47 |
| 29 | 122 | 19 | 167 | | 60 |
| 30 | 151 | 17 | 559 | | 72 |
| 31 | 5 | 16.4 | | 8.8 | 100 |
| 32 | 481 | 14.2 | 315 | 2 | 129 |
| 33 | 330 | 14 | 91 | | 147 |
| 34 | 359 | 13 | 14 | | 37 |
| 35 | 196 | 12 | 10 | 2 | 152 |
| 36 | 425 | 11.9 | 892 | 0.5 | 157 |
| 37 | 28 | 10.7 | 31 | 2.4 | 92 |
| 38 | 271 | 10.1 | 13.8 | | 63 |
| 39 | 108 | 9 | 33 | | 57 |
| 40 | 453 | 8 | 12 | 0 | 105 |
| 41 | 346 | 7 | 10 | | 93 |
| 42 | 221 | 7 | 16 | 0 | 51 |
| 43 | 333 | 6.9 | 12 | 0 | 50 |
| 44 | 584 | 6.2 | 19 | 0 | 51 |
| 45 | 95 | 6 | 42 | 6.7 | 91 |
| 46 | 82 | 5.7 | 15 | 0 | 51 |
| 47 | 340 | 5.6 | 16 | 0 | 42 |
| 48 | 264 | 5 | 13 | | 83 |
| 49 | 4 | 5 | 26 | 0 | 52 |
| 50 | 130 | 4.8 | 15 | 0 | 58 |
| 51 | 23 | 4 | 14 | | 45 |
| 52 | 256 | 4 | 25 | — | 44 |
| 53 | 341 | 3 | | | 73 |
| 54 | 483 | 3 | 17 | | 41 |
| 55 | 466 | 3 | 15 | | 43 |
| 56 | 228 | 2 | 15 | | 36 |
| 57 | 36 | 1 | 14 | | 47 |
| 58 | 426 | | | | 56 |
| 59 | 251 | | | | 53 |
| 60 | 141 | | | | 53 |
| 61 | 230 | | | | 31 |
| 62 | 366 | | | | 27 |
| 63 | 452 | | | | 115 |
| 64 | 328 | | | | 111 |
| 65 | 429 | | 47 | | 111 |
| 66 | 507 | | | | 108 |
| 67 | 239 | | 15 | | 77 |
| 68 | 41 | | | | 70 |
| 69 | 203 | | 14 | | 67 |
| 70 | 50 | | | | 65 |
| 71 | 457 | | | | 64 |
| 72 | 266 | | | | 63 |
| 73 | 320 | | 21 | | 60 |
| 74 | 279 | | | | 50 |
| 75 | 255 | | | | 49 |
| 76 | 534 | | | | 47 |
| 77 | 395 | | | | 44 |
| 78 | 487 | — | — | — | 80 |
| 79 | 175 | — | | — | 56 |
| positive n | | 27 | 16 | 6 | 36 |
| positive % | | 46 | 30 | 18 | 46 |

Note:
Blanks in the table indicate "unmeasured".

TABLE 5

Concentration of ROBO1 in blood of hepatic cirrhosis and chronic hepatitis patients

| ID NO. | diagnosis | AFP (ng/ml) | PIVKA (U/ml) | AFP-L3 (%) | ROBO1 (ng/ml) |
|---|---|---|---|---|---|
| 1 | 791 | LC | 59.8 | | 9.8 | 112 |
| 2 | 515 | LC | 41 | — | — | 129 |
| 3 | 740 | LC | 36 | 16 | 2.1 | 95 |
| 4 | 71 | LC | 33 | | | 125 |
| 5 | 187 | LC | 24.4 | 12 | 5.6 | 107 |
| 6 | 443 | LC | 22 | — | — | 106 |
| 7 | 20 | LC | 20 | | | 94 |
| 8 | 777 | LC | 20 | | | 92 |
| 9 | 675 | LC | 17 | | | 95 |
| 10 | 601 | LC | 16 | 10 | — | 87 |
| 11 | 445 | LC | 13 | — | — | 88 |
| 12 | 378 | LC | 13 | 23 | — | 87 |
| 13 | 940 | LC | 9 | | | 75 |
| 14 | 628 | LC | 8 | | | 57 |
| 15 | 260 | LC | 6.3 | 10 | 0 | 61 |
| 16 | 245 | LC | 6 | 19 | — | 82 |
| 17 | 67 | LC | 6 | 18 | | 79 |
| 18 | 776 | LC | 6 | | | 61 |
| 19 | 932 | LC | 6 | 35 | | 58 |
| 20 | 137 | LC | 6 | | | 60 |
| 21 | 574 | LC | 6 | — | — | 50 |
| 22 | 220 | LC | 5.7 | | 0 | 87 |
| 23 | 533 | LC | 5 | | | 105 |
| 24 | 1165 | LC | 5 | | | 57 |
| 25 | 59 | LC | 5 | 11 | | 59 |
| 26 | 62 | LC | 4 | 11 | | 110 |
| 27 | 1149 | LC | 4 | 10 | | 101 |
| 28 | 80 | LC | 4 | — | — | 77 |
| 29 | 375 | LC | 4 | — | — | 48 |
| 30 | 878 | LC | 4 | | | 46 |
| 31 | 1128 | LC | 4 | | | 47 |
| 32 | 69 | LC | 3 | 10 | | 76 |
| 33 | 138 | LC | 3 | | | 74 |
| 34 | 513 | LC | 3 | — | — | 66 |
| 35 | 105 | LC | 3 | 12 | — | 54 |
| 36 | 570 | LC | 3 | | | 50 |
| 37 | 561 | LC | 2 | 13 | — | 40 |
| 38 | 1030 | LC | 2 | 14 | | 28 |
| 39 | 671 | LC | 1 | | | 87 |
| 40 | 1198 | LC | 1 | 26 | | 81 |
| 41 | 479 | LC | 1 | — | — | 59 |
| 42 | 172 | LC | 1 | 21 | — | 50 |
| 43 | 49 | LC | 1 | — | — | 47 |
| 44 | 409 | LC | 1 | — | — | 45 |
| 45 | 374 | LC | — | 12 | — | 105 |
| 46 | 222 | LC | — | — | — | 102 |
| 47 | 1143 | LC | | 11 | | 91 |
| 48 | 565 | LC | | | | 87 |
| 49 | 870 | LC | | 15 | | 83 |
| 50 | 380 | LC | | | | 80 |
| 51 | 193 | LC | | | | 76 |
| 52 | 169 | LC | | | | 66 |
| 53 | 921 | LC | | 10 | | 62 |
| 54 | 922 | LC | | 14 | | 50 |
| 55 | 691 | LC | | | | 48 |
| 56 | 981 | LC | | | | 30 |
| 57 | 116 | LC | | | | 66 |
| 58 | 1035 | LC | | 10 | | 53 |
| 59 | 192 | CH | 17 | | | 43 |

TABLE 5-continued

Concentration of ROBO1 in blood of hepatic cirrhosis and chronic hepatitis patients

|  | ID NO. | diag-nosis | AFP (ng/ml) | PIVKA (U/ml) | AFP-L3 (%) | ROBO1 (ng/ml) |
|---|---|---|---|---|---|---|
| 60 | 458 | CH | 15 |  |  | 43 |
| 61 | 379 | CH | 6 | 14 |  | 32 |
| 62 | 772 | CH | 4 | 14 |  | 28 |
| 63 | 421 | CH | 3 |  |  | 32 |
| 64 | 568 | CH | — | — | — | 39 |
| 65 | 1090 | CH |  | 13 |  | 33 |
| 66 | 302 | CH |  | 17 |  | 59 |
| 67 | 285 | CH |  |  |  | 45 |
|  |  | n | 8 | 0 | 0 | 15 |
|  |  | % | 15 | 0 | 0 | 22 |

Note:
Blanks in the table indicate "unmeasured".

TABLE 6

Concentration of ROBO1 in blood of cancer patients other than hepatic cancer

|  | ID number | diagnosis | ROBO1 (ng/ml) |
|---|---|---|---|
| 1 | 43 | leukemia | 27 |
| 2 | 58 | leukemia | 61 |
| 3 | 84 | leukemia | 56 |
| 4 | 182 | leukemia | 64 |
| 5 | 204 | leukemia | 52 |
| 6 | 159 | lung cancer | 128 |
| 7 | 161 | lung cancer | 57 |
| 8 | 76 | brain tumor | 15 |
| 9 | 29 | gallbladder cancer | 41 |
| 10 | 175 | cholangiocarcinoma | 53 |
| 11 | 168 | colorectal cancer | 50 |
| 12 | 68 | pancreas cancer | 54 |
| 13 | 71 | esophageal carcinoma | 10 |
| 14 | 106 | myeloma | 31 |
| 15 | 49 | stomach cancer | 1 |
| 16 | 50 | stomach cancer | 80 |
| 17 | 69 | stomach cancer | 43 |
| 18 | 70 | stomach cancer | 67 |
| 19 | 105 | stomach cancer | 18 |
| 20 | 113 | stomach cancer | 39 |
| 21 | 147 | stomach cancer | 128 |
| 22 | 48 | submandibular gland cancer | 30 |
|  | positive | n | 2 |
|  |  | % | 9.1 |

From the fact that the mean value and standard deviation 36 ng/mL and 8 ng/mL in the measurements of ROBO1 concentration in 72 cases of healthy subject sera, 81 ng/mL, that is mean value+(6× standard deviation), was taken as the cutoff value. As a result, all the cases of healthy subject serum samples were below this cutoff value; in contrast, 46% (36 cases out of 79 cases) of hepatic cancer patient samples, 22% (15 cases out of 67 cases) of hepatic cirrhosis/chronic hepatitis patient samples and 9% (2 cases out of 22 cases) of other cancer patient samples showed not less than the cutoff value, indicating ROBO1 positive. The positive rate of AFP, which is generally used as a diagnostic marker for hepatic cancer, was 46% (27 cases out of 59 cases) and 15% (8 cases out of 52 cases) in hepatic cancer patient samples and hepatic cirrhosis/chronic hepatitis patient samples, respectively. thus the sensitivity and specificity in hepatic cancer diagnosis were approximately equivalent between AFP and ROBO1. Meanwhile, 10 out of 32 cases of AFP negative hepatic cancer patient samples showed ROBO1 positive, and PIVKA was also negative in 5 cases of these 10 cases. It suggests that hepatic cancer can be diagnosed with ROBO1 even in the cases that could not be diagnosed as hepatic cancer by existing diagnostic methods. In fact, the positive rate was 46% by AFP alone, while it was 63% by a combination with ROBO1.

The above results showed that ROBO1 measurement system has an approximately equivalent capability to the existing AFP measurement system in the diagnosis of hepatic cancer, and it is possible to establish a cancer diagnostic method with high sensitivity and specificity by combining ROBO1 with existing cancer markers.

Figure 11:
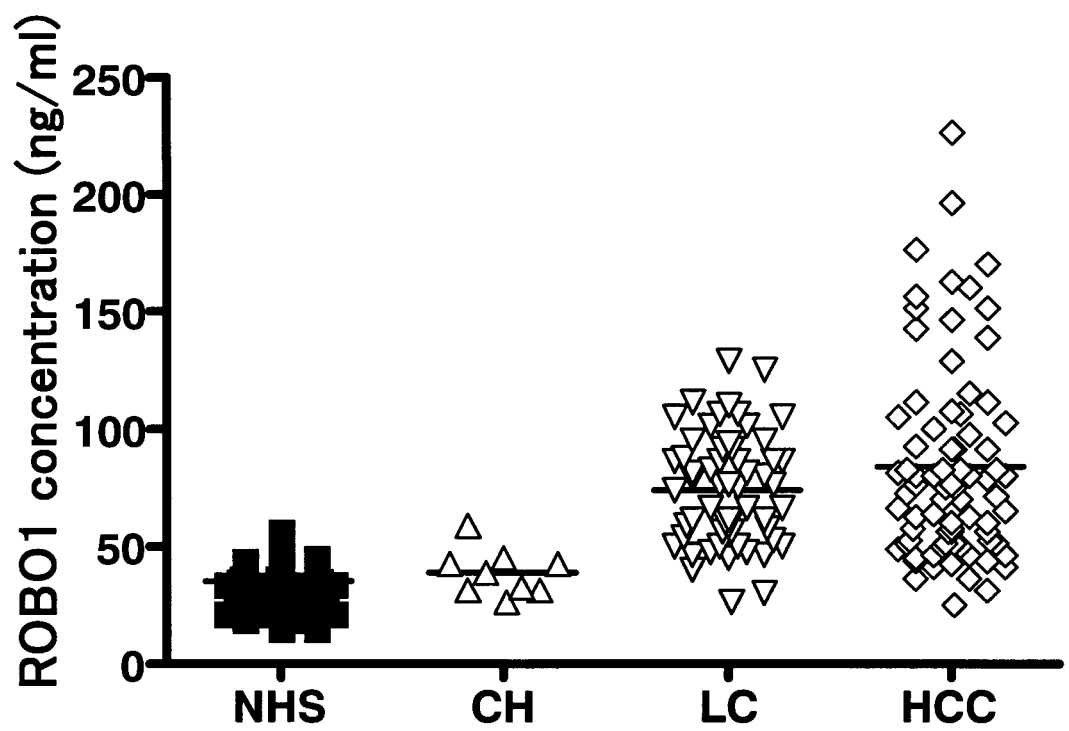
FIG. 11 shows the correlation between ROBO1 concentration and the severity of liver diseases.

The values shown in Tables 3, 4, 5 and 6 are plotted by disease and shown in FIG. 11. The mean ROBO1 concentration in sera of healthy subjects (NHS), chronic hepatitis (CH), hepatic cirrhosis (LC) and hepatic cancer (HCC), were 34.8, 39.3, 74.0 and 84.4 ng/mL, respectively. This result clearly shows that the ROBO1 concentration in the sera from each group of healthy subject, chronic hepatitis, hepatic cirrhosis and hepatic cancer patients increased proportionally to the progression of liver disease.

Figure 12:
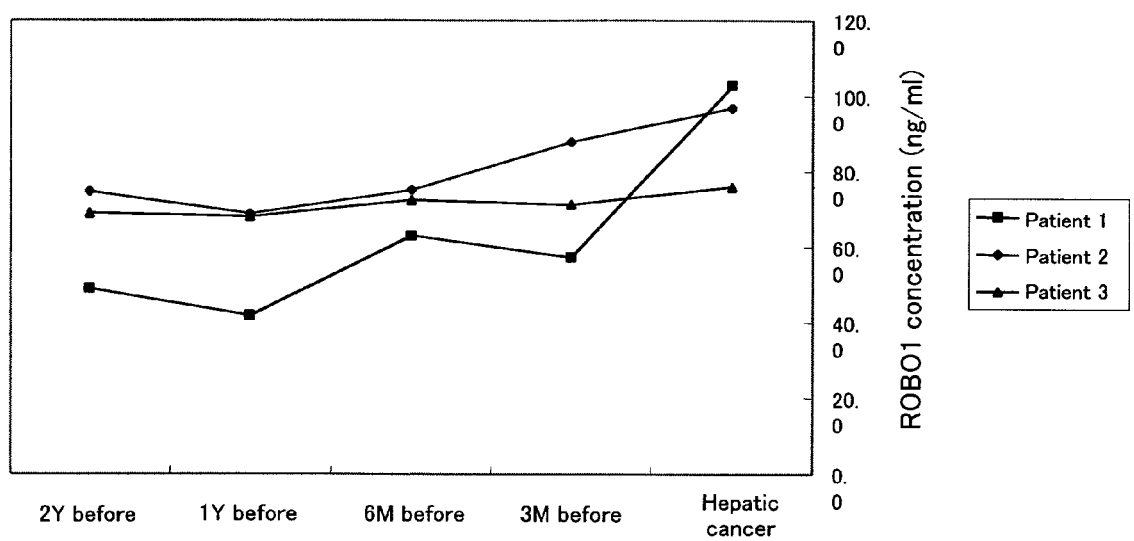
FIG. 12 shows the variation in ROBO1 concentration of liver disease patients.

Next, in order to determine whether the ROBO1 concentration varies also in time-course measurements for each individual, ROBO1 concentration in blood samples collected before onset of hepatic cancer was measured. ROBO1 concentration in blood was observed to be increased proportionally to progression in 2 out of 3 cases tested (FIG. 12). No increase proportional to progression was observed in one case, probably because the maximum value had been reached, which is higher than the healthy subject (30 to 40 ng/mL).

These results show that not only the diagnosis of hepatic cancer but also the severity of liver disease in the patient can be managed by measuring or monitoring the time-course of the ROBO1 concentration in serum from the patients with liver disease.

Example 11

Measurement of Complement-Dependent Cytotoxicity (CDC Activity)
Creation of Human Albumin Veronal Buffer (HAVB)

A solution was prepared by dissolving 12.75 g of NaCl (Special Grade, Wako Pure Chemical Industries, Ltd.), 0.5625 g of Na-barbital (Special Grade, Wako Pure Chemical Industries, Ltd.), and 0.8625 g of barbital (Special Grade, Wako Pure Chemical Industries, Ltd.) in Milli Q water and filled to 200 mL, and autoclaveed (121° C., 20 minutes). A volume of 100 mL of autoclaved hot Milli Q water was added and found to be pH 7.43 (recommended pH: 7.5), which served as 5× veronal buffer. An amount of 0.2205 g of $CaCl_2.2H_2O$ (Special Grade, Junsei Chemical Co., Ltd.) was dissolved in 50 mL Milli Q water to obtain 0.03 mol/L, which served as a $CaCl_2$ solution. An amount of 1.0165 g of $MgCl_2.6H_2O$ (Special Grade, Junsei Chemical Co., Ltd.) was dissolved in 50 mL Milli Q water to obtain 0.1 mol/L, which served as a $MgCl_2$ solution. A volume of 100 mL of 5× veronal buffer, 4 mL of human serum albumin (25% Buminate®, 250 mg/mL human serum albumin concentration, Baxter), 2.5 mL of $CaCl_2$ solution, 2.5 mL of $MgCl_2$ solution, 0.1 g of KCl (Special Grade, Junsei Chemical Co., Ltd.), and 0.5 g of glucose (D(+)-glucose, glucose anhydrous, Special Grade, Wako Pure Chemical Industries, Ltd.) were dissolved in Milli Q water, and brought to 500 mL. This served as HAVB. After sterilization by filtration, the solution was stored at a set temperature of 5° C.

Preparation of Target Cell

HEK293 cell forced to express ROBO1 was cultured in a DMEM culture medium (SIGMA) supplemented with 10% FBS (Thermo Trace) and 0.5 mg/mL Geneticin (GIBCO), released from the dish using cell detachment buffer solution (GIBCO), dispensed at 1×10⁴ cells/well in each well of a 96-well U bottomed plate (BECTON DICKINSON), and cultured overnight. To the culture 5.55 MBq of chromium-51 was added and incubated in a 5% carbon dioxide incubator at 37° C. for one hour. The cells were washed twice with HAVB, and 50 µL of HAVB was added to prepare a target cell.

Preparation of Baby Rabbit Complement

For a complement solution, baby rabbit complement (BABY RABBIT COMPLEMENT, CEDARLANE), which was prepared immediately before use, was dissolved in 1 mL per vial of injectable distilled water (Fuso Pharmaceutical Industries, Ltd.) at the time of examination.

Chromium Release Test (CDC Activity)

Anti-ROBO1 antiserum (anti-ROBO1 rabbit polyclonal antibody) was diluted with HAVB to obtain 1/50 and 1/500 fold antibody solutions. A volume of 50 µL each of antibody solution was added to target cells, and let to stand on ice for 15 minutes. Next, 100 µL/mL each of complement solution was added to each well (with final antibody dilution ratios of 1/200 and 1/2000), and was let to stand in a 5% carbon dioxide incubator at 37° C. for 90 minutes. After centrifugation of the plate, 100 µL each of supernatant was collected from each well, and the radioactivity was measured with a gamma counter. The specific chromium release rate was determined according to the following equation:

specific chromium release rate (%)=(A−C)/(B−C)×100 where A represents the radioactivity (cpm) in a well, B represents the mean value of radioactivity (cpm) in a well where 100 µL of 2% NP-40 aqueous solution (Nonidet P-40, Nacalai Tesque Co, Ltd.) and 50 µL of HAVB were added to the target cells, and C represents the mean value of radioactivity (cpm) in a well where 150 µL of HAVB was added to the target cells. The test was carried out in triplicate, and mean value and standard deviation were calculated for the CDC activity (%).

Figure 13:
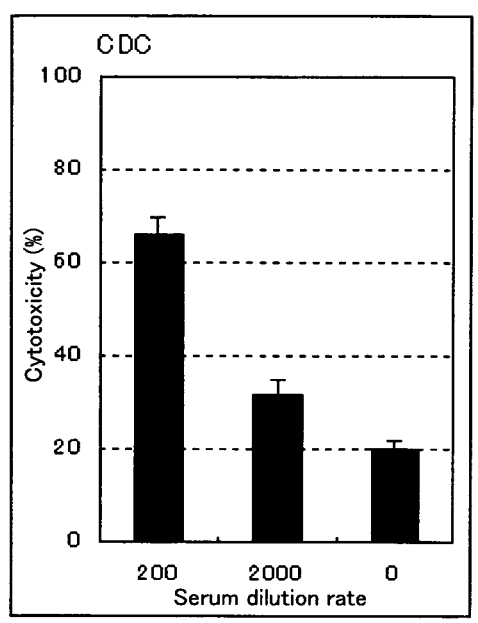
FIG. 13 shows the results of measurement of CDC activity of anti-ROBO1 antiserum against ROBO1-expressing HEK293 cell.

The results are shown in FIG. 13. It was apparent that the anti-ROBO1 antiserum, that is the anti-ROBO1 polyclonal antibody, showed dose-dependent CDC activity against ROBO1 expressing HEK293 cells. No CDC activity was detected with rabbit preserum or without addition of antibody.

Example 12

Preparation of Monoclonal Antibody that Binds to Extracellular Region of ROBO1

12-1. Preparation of Recombinant Baculovirus Expressing the N-Terminal Region of ROBO1

The fibronectin III region (FnIII) present in the extracellular region of ROBO1 was expressed as a fusion protein with the baculovial membrane protein gp64. A gene coding for the third fibronectin region of ROBO1 was amplified by the PCR method with the ROBO1 cDNA as a template, using the gp4F primer (SEQ ID NO: 15) and the gp4R primer (SEQ ID NO: 16), and inserted into the pGEM-Te vector (manufactured by Promega). After the nucleotide sequence was confirmed by an established method, a gene fragment cleaved by restriction endonuclease KpnI was inserted into the pBucSurf vector (manufactured by Novagen), to construct the transfer vector ROBO1gp4/pBS. Then, 4 µg of ROBO1gp4/pBS was cut and linearized with the restriction endonuclease BplI (manufactured by Fermentas), and introduced together with a Bac-N-Blue DNA into Sf9 cell according to the instructions from Invitrogen, to prepare a recombinant baculovirus that expresses a fusion protein of FnIII from ROBO1 and gp64.

SEQ ID NO: 15: GGTACCCGCACCCAGTGCCCCACCCCAAGG

SEQ ID NO: 16: GGTACCGCATCTGAAATCTGCTGAGCGAGG

The recombinant virus prepared as described above was added to infect Sf9 cells (2×10⁶ cells/mL) at an MOI of 5, which were cultured at 27° C. for 3 days. Budding baculoviruses (BV) expressing the fusion protein of ROBO1-FnIII and gp64 were recovered from the culture supernatant after 3 days culture. The culture solution was centrifuged at 800×g for 15 minutes to remove cells and cell debris, and the culture supernatant was centrifuged at 45,000×g for 30 minutes. The precipitate was suspended in PBS and further centrifuged at 800×g to remove cell constituents. The supernatant was centrifuged again at 45,000×g and the precipitate was suspended in PBS to serve as BV fraction for use in immunization.

12-2. Preparation of Anti-ROBO1 Monoclonal Antibody

The ROBO1-FnIII expressing BV prepared by the above method was used as an antigen to generate an anti-ROBO1 monoclonal antibody. ROBO1-FnIII expressing BV corresponding to a protein amount of 1 mg was suspended in PBS and mixed with 200 ng of pertussis, and then subcutaneously injected into a gp64 transgenic mouse (WO03/104453) for an initial immunization. In a subsequent immunization, only ROBO1-FnIII expressing BV corresponding to a protein amount of 500 µg was injected subcutaneously. As a final immunization, 250 µg of ROBO1-FnIII expressing BV was administered intravascularly. After 3 days, spleen cells were isolated from the mouse and fused with mouse NS-1 cells according to conventional methods to establish a hybridoma cell. Hybridoma cell producing anti-ROBO1 antibody was selected by ELISA using the solid-phased ROBO1-FnIII expressing BV, the antigen used for immunization. In the ELISA method, ROBO1-FnIII expressing BV was left for one day and night in a 96-well flat-bottomed plate (manufactured by Falcon) at 4° C. at final concentration of 10 µg/ml, and blocked with a TBS buffer solution containing 40% Block Ace reagent (manufactured by Dainippon Pharmaceutical Co., Ltd.). A hybridoma culture supernatant was added, and the reaction was let to take place at room temperature for one hour. Next, HRP labeled antimouse IgG antibody (manufactured by Jackson) was added at room temperature for one hour, washed 4 times, and 3,3',5,5'-tetramethylbenzin (TMB) reagent (manufactured by Sigma) was added at room temperature for one hour. The reaction was stopped with 0.5N sulfuric acid, and the optical density at 492 nm was measured with the microplate reader Multickan JX (manufactured by Labsystems).

A hybridoma cell B2318C producing a monoclonal antibody that binds to ROBO1 was established successfully. The monoclonal antibody was prepared from the culture supernatant of the hybridoma cells by the ammonium sulfate precipitation method.

Example 13

Measurement of Complement-Dependent Cytotoxicity (CDC Activity)

Preparation of human albumin•veronal•buffer (HAVB), target cells, and baby rabbit complement were carried out similarly to Example 11.

B2318C antibody (anti-ROBO1 monoclonal antibody) was diluted with HAVB, 50 µL each was added to target cells, and let to stand on ice for 15 minutes. Next, 100 µL/mL each of complement solution was added to each well (prepared with final concentrations of antibody of 1 µg/mL and 10 µg/mL), and incubated in a 5% carbon dioxide incubator at 37° C. for 90 minutes. After centrifugation of the plate, 100 μL each of supernatant was collected from each well, and the radioactivity was measured with a gamma counter. The specific chromium release rate was determined according to the following equation:

specific chromium release rate (%)=$(A-C)/(B-C) \times 100$ where A represents the radioactivity (cpm) in a well, B represents the mean value of radioactivity (cpm) in a well where 100 μL of 2% NP-40 aqueous solution (Nonidet P-40, Nacalai Tesque Co, Ltd.) and 50 μL of HAVB were added to the target cells, and C represents the mean value of radioactivity (cpm) in a well where 150 μL of HAVB was added to the target cells. The test was carried out in triplicate, and mean value and standard deviation were calculated for the CDC activity (%).

Figure 14:
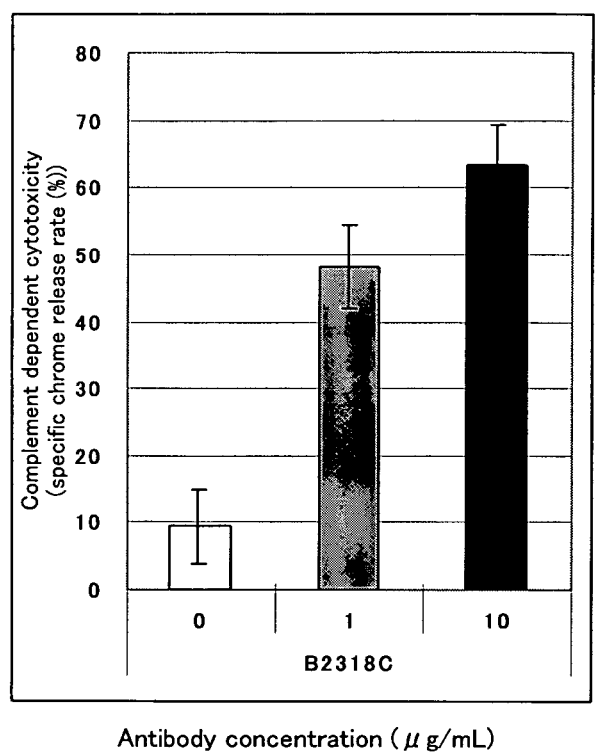
FIG. 14 shows the results of measurement of CDC activity of anti-ROBO1 monoclonal antibody against ROBO1-expressing HEK293 cell.

The results are shown in FIG. 14. The anti-ROBO1 monoclonal antibody B2318C demonstrated dose-dependent CDC activity against ROBO1 expressing HEK293 cells.

Figure 15:
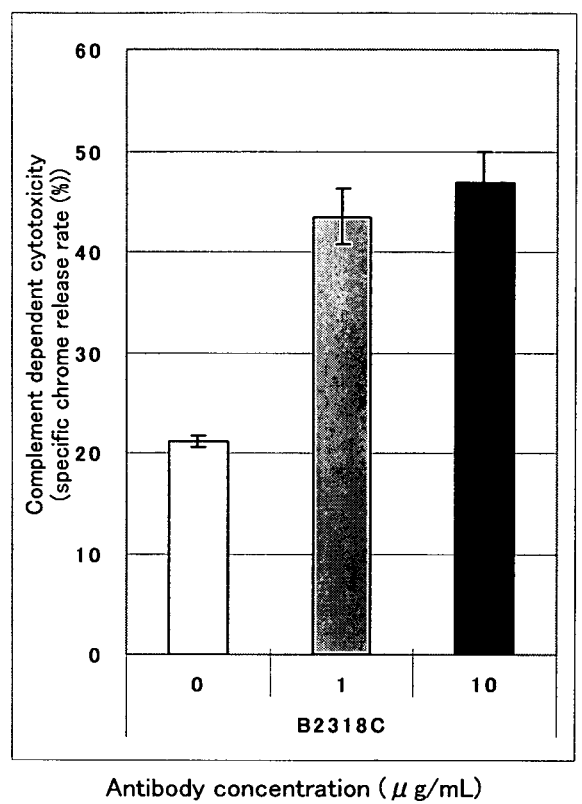
FIG. 15 shows the results of measurement of CDC activity of anti-ROBO1 monoclonal antibody against ROBO1-expressing Alexander cell.

The anti-ROBO1 monoclonal antibody B2318C demonstrated dose-dependent CDC activity on Alexander (PLC/PRF/5) cells, also a liver cancer cell line, which is similar to the effect against ROBO1 expressing HEK293 cell (FIG. 15).

Example 14

Measurement of ADCC Activity Using Mouse Bone Marrow-Derived Effector Cells 14-1. Preparation of Mouse Bone Marrow-Derived Effector Cell Solution Bone marrow cells were collected from the femoral bone of a SCID mouse (10 weeks old male, Clea Japan), and suspended at $5 \times 10^5$ cells/mL in a 10% FBS/RPMI 1640 culture medium. Mouse GM-CSF (PeproTech) and human IL-2 (PeproTech) were added at 10 ng/mL and 50 ng/mL, respectively, and the cells were cultured in a 5% carbon dioxide incubator at 37° C. for 5 days. After the culture, the cells were peeled with a scraper, washed once with culture medium, suspended at $5 \times 10^6$/cells/mL in 10% FBS/RPMI 1640 culture medium to prepare a mouse bone marrow-derived effector cell solution.

14-2. Preparation of Target Cell

HEK293 cells overexpressing ROBO1 were maintained in a DMEM culture medium (manufactured by Sigma) containing 10% FBS (manufactured by ThermoTrace) and 500 ng/mL Geneticine (Invitrogen), and removed from the dish using the Cell Dissociation Buffer (Invitrogen). The cells were dispensed at $1 \times 10^4$ cells/well in each well of a 96-well U bottomed plate (Falcon), and cultured overnight. After the culture, 5.55 MBq of chromium-51 was added and incubated in a 5% carbon dioxide incubator at 37° C. for four hours. The cells were washed three times with culture medium, and 50 μL of 10% FBS/RPMI1640 culture medium was added to prepare a target cell.

14-3. Chromium Release Test (ADCC Activity)

A volume of 50 μL of B2318C antibody (anti-ROBO1 monoclonal antibody) solution was added to target cells, and let to stand on ice for 15 minutes. Then, 100 μL of mouse bone marrow-derived effector cell solution ($5 \times 10^5$ cells/well) was added, and incubated in a 5% carbon dioxide incubator at 37° C. for 4 hours (prepared at final antibody concentrations of 1 μg/mL and 10 μg/mL). The plate was centrifuged and the radioactivity in 100 μL of culture supernatant was measured with a gamma counter. The specific chromium release rate was determined according to the following equation:

specific chromium release rate (%)=$(A-C) \times 100/(B-C)$ where A represents the mean value of radioactivity (cpm) in a well, B represents the mean value of radioactivity (cpm) in a well where 100 μL of 2% NP-40 aqueous solution (Nonidet P-40, Code No. 252-23, Nacalai Tesque Co, Ltd.) and 50 μL of 10% FBS/RPMI culture medium were added to the target cells, and C represents the mean value of radioactivity (cpm) in a well where 150 μL of 10% FBS/RPMI culture medium was added to the target cells. The test was carried out in triplicate, and mean value and standard deviation were calculated for the ADCC activity (%).

Figure 16:
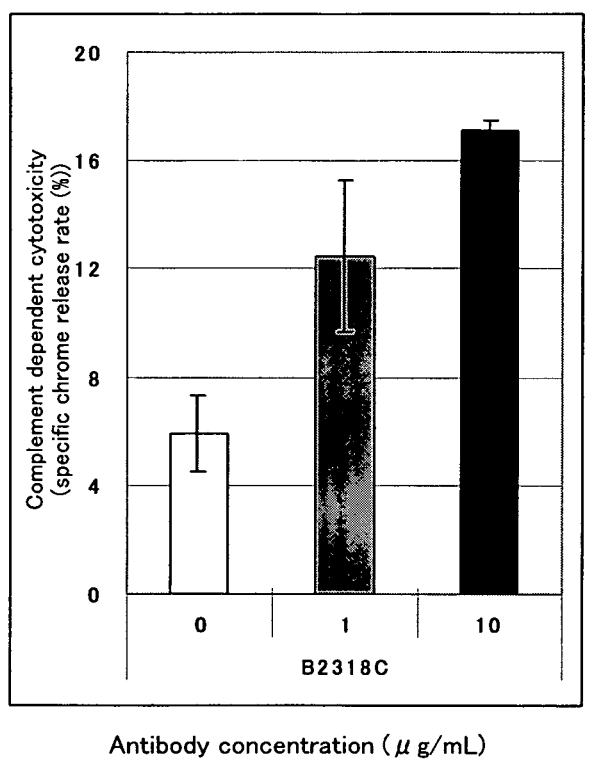
FIG. 16 shows the results of measurement of ADCC activity of anti-ROBO1 monoclonal antibody against ROBO1-expressing HEK293 cell.

The results are shown in FIG. 16. The anti-ROBO1 monoclonal antibody B2318C demonstrated dose-dependent ADCC activity against ROBO1 expressing HEK293 cells.

These results demonstrated that anti-ROBO1 monoclonal antibody would be effective in the treatment of ROBO1-expressing cancer.

The present invention is useful in the diagnosis and treatment of cancers, as well as in monitoring of progression of hepatitis.

The invention claimed is:

1. A method for diagnosing cancer comprising the steps of:
   (a) collecting a test sample selected from blood, serum or plasma from a subject,
   (b) contacting an anti-ROBO1 antibody which binds to 1-898 of the amino acid sequence of SEQ ID NO: 9 or 1-859 of the amino acid sequence of SEQ ID NO: 11 to the test sample,
   (c) detecting a first complex comprising the anti-ROBO1 antibody,
   (d) contacting a control sample selected from blood serum or plasma from a healthy subject with an anti-ROBO1 antibody which binds to 1-898 of the amino acid sequence of SEQ ID NO: 9 or 1-859 of the amino acid sequence of SEQ ID NO: 11,
   (e) detecting a second complex comprising the anti-ROBO1 antibody,
   (f) comparing the level of the first complex detected in step (c) to the level of the second complex detected in step (e), and
   (g) diagnosing the subject as having cancer when the level of the first complex is higher than the level of the second complex; and
   wherein the cancer is selected from the group consisting of, breast cancer, gastric cancer, hepatic cancer, large intestine cancer, and lung cancer.

2. A method for monitoring progression of hepatitis comprising the steps of:
   (a) collecting a first sample selected from blood, serum or plasma from a subject,
   (b) contacting an anti-ROBO 1 antibody which binds to 1-898 of the amino acid sequence of SEQ ID NO: 9 or 1-859 of the amino acid sequence of SEQ ID NO:11 to the collected sample,
   (c) detecting a first complex comprising the anti-ROBO1 antibody,
   (d) collecting a second sample selected from blood, serum or plasma from a subject at a later point in time,
   (e) contacting an anti-ROBO1 antibody which binds 1-898 of to the amino acid sequence of SEQ ID NO: 9 or 1-859 of the amino acid sequence of SEQ ID NO:11 to the second collected sample,
   (f) detecting a second complex comprising the anti-ROBO1 antibody,
   (g) comparing the level of the second complex detected in the second sample from the subject to the level of the first complex detected in the first sample collected from the same subject at a previous time point, and
   (h) determining that hepatitis has progressed when the level of the second complex is higher than the level of the first complex collected at the previous point in time.

3. The method according to claim 2 comprising predicting the progression from hepatitis or hepatic cirrhosis to hepatic cancer.

4. The method according to any one of claim 1, 2 or 3 wherein a first anti-ROBO1 antibody immobilized on a support and a second anti-ROBO1 antibody labeled with a labeling substance are used.

5. The method according to claim 1 wherein the collected test sample is blood.

6. The method according to claim 1 wherein the collected test sample is serum.

7. The method according to claim 1 wherein the collected test sample is plasma.

8. The method according to claim 1 wherein an anti-ROBO1 antibody binds 1-898 of the amino acid sequence of SEQ ID NO: 9.

9. The method according to claim 1 wherein an anti-ROBO1 antibody binds 1-859 of the amino acid sequence of SEQ ID NO:11.

10. The method according to claim 1 wherein the anti-ROBO1 antibody of step (b) and the anti-ROBO 1 antibody of step (d) are the same.

11. The method according to claim 1 wherein the cancer is breast cancer.

12. The method according to claim 1 wherein the cancer is gastric cancer.

13. The method according to claim 1 wherein the cancer is hepatic cancer.

14. The method according to claim 1 wherein the cancer is large intestine cancer.

15. The method according to claim 1 wherein the cancer is lung cancer.

16. The method according to claim 2 wherein the collected first sample is blood.

17. The method according to claim 2 wherein the collected first sample is serum.

18. The method according to claim 2 wherein the collected first sample is plasma.

19. The method according to claim 2 wherein an anti-ROBO1 antibody binds 1-898 of the amino acid sequence of SEQ ID NO 9.

20. The method according to claim 2 wherein an anti-ROBO1 antibody binds 1-859 of the amino acid sequence of SEQ ID NO:11.

21. The method according to claim 2 wherein the anti-ROBO1 antibody of step (b) and the anti-ROBO1 antibody of step (e) are the same.

22. The method according to claim 2 comprising predicting the progression from hepatic cirrhosis to hepatic cancer.

* * * * *

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: PCR primer

<400> SEQUENCE: 1
gtggagggag gcctggac                                                        18

<210> SEQ ID NO 2
<211> LENGTH: 19
<212> TYPE: DNA
<213> ORGANISM: Artificial Sequence
<220> FEATURE:
<223> OTHER INFORMATION: PCR primer

<400> SEQUENCE: 2
```
ttaggccacg tgtctgcca                                                    19

<210> SEQ ID NO 3
<211> LENGTH: 25
<212> TYPE: DNA
<213> ORGANISM: Artificial Sequence
<220> FEATURE:
<223> OTHER INFORMATION: PCR primer

<400> SEQUENCE: 3
agaaggagat cactgccctg gcacc                                             25

<210> SEQ ID NO 4
<211> LENGTH: 25
<212> TYPE: DNA
<213> ORGANISM: Artificial Sequence
<220> FEATURE:
<223> OTHER INFORMATION: PCR primer

<400> SEQUENCE: 4
cctgcttgct gatccacatc tgctg                                             25

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
accatgattg cggagcccgc tcac                                              24

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
gctttcagtt tcctctaatt c                                                 21

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
ggtacccctt cgtcaggaag attttccac                                         29

<210> SEQ ID NO 8
<211> LENGTH: 26
<212> TYPE: DNA
<213> ORGANISM: Artificial Sequence
<220> FEATURE:
<223> OTHER INFORMATION: PCR primer

<400> SEQUENCE: 8
ggtaccgagt aattccttgc tacaca                                            26

<210> SEQ ID NO 9
<211> LENGTH: 1651
<212> TYPE: PRT

<213> ORGANISM: homo sapiens

<400> SEQUENCE: 9

Met Lys Trp Lys His Val Pro Phe Leu Val Met Ile Ser Leu Leu Ser
1               5                   10                  15

Leu Ser Pro Asn His Leu Phe Leu Ala Gln Leu Ile Pro Asp Pro Glu
            20                  25                  30

Asp Val Glu Arg Gly Asn Asp His Gly Thr Pro Ile Pro Thr Ser Asp
        35                  40                  45

Asn Asp Asp Asn Ser Leu Gly Tyr Thr Gly Ser Arg Leu Arg Gln Glu
    50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
130                 135                 140

Tyr Val Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
290                 295                 300

Ser Arg Tyr Glu Ile Arg Asp Asp His Thr Leu Lys Ile Arg Lys Val
305                 310                 315                 320

Thr Ala Gly Asp Met Gly Ser Tyr Thr Cys Val Ala Glu Asn Met Val
                325                 330                 335

Gly Lys Ala Glu Ala Ser Ala Thr Leu Thr Val Gln Glu Pro Pro His
            340                 345                 350

Phe Val Val Lys Pro Arg Asp Gln Val Val Ala Leu Gly Arg Thr Val
        355                 360                 365

Thr Phe Gln Cys Glu Ala Thr Gly Asn Pro Gln Pro Ala Ile Phe Trp
370                 375                 380

Arg Arg Glu Gly Ser Gln Asn Leu Leu Phe Ser Tyr Gln Pro Pro Gln
385                 390                 395                 400

-continued

```
Ser Ser Ser Arg Phe Ser Val Ser Gln Thr Gly Asp Leu Thr Ile Thr
                405                 410                 415
Asn Val Gln Arg Ser Asp Val Gly Tyr Tyr Ile Cys Gln Thr Leu Asn
            420                 425                 430
Val Ala Gly Ser Ile Ile Thr Lys Ala Tyr Leu Glu Val Thr Asp Val
        435                 440                 445
Ile Ala Asp Arg Pro Pro Val Ile Arg Gln Gly Pro Val Asn Gln
450                 455                 460
Thr Val Ala Val Asp Gly Thr Phe Val Leu Ser Cys Val Ala Thr Gly
465                 470                 475                 480
Ser Pro Val Pro Thr Ile Leu Trp Arg Lys Asp Gly Val Leu Val Ser
                485                 490                 495
Thr Gln Asp Ser Arg Ile Lys Gln Leu Glu Asn Gly Val Leu Gln Ile
            500                 505                 510
Arg Tyr Ala Lys Leu Gly Asp Thr Gly Arg Tyr Thr Cys Ile Ala Ser
        515                 520                 525
Thr Pro Ser Gly Glu Ala Thr Trp Ser Ala Tyr Ile Glu Val Gln Glu
    530                 535                 540
Phe Gly Val Pro Val Gln Pro Pro Arg Pro Thr Asp Pro Asn Leu Ile
545                 550                 555                 560
Pro Ser Ala Pro Ser Lys Pro Glu Val Thr Asp Val Ser Arg Asn Thr
                565                 570                 575
Val Thr Leu Ser Trp Gln Pro Asn Leu Asn Ser Gly Ala Thr Pro Thr
            580                 585                 590
Ser Tyr Ile Ile Glu Ala Phe Ser His Ala Ser Gly Ser Ser Trp Gln
        595                 600                 605
Thr Val Ala Glu Asn Val Lys Thr Glu Thr Ser Ala Ile Lys Gly Leu
    610                 615                 620
Lys Pro Asn Ala Ile Tyr Leu Phe Leu Val Arg Ala Ala Asn Ala Tyr
625                 630                 635                 640
Gly Ile Ser Asp Pro Ser Gln Ile Ser Asp Pro Val Lys Thr Gln Asp
                645                 650                 655
Val Leu Pro Thr Ser Gln Gly Val Asp His Lys Gln Val Gln Arg Glu
            660                 665                 670
Leu Gly Asn Ala Val Leu His Leu His Asn Pro Thr Val Leu Ser Ser
        675                 680                 685
Ser Ser Ile Glu Val His Trp Thr Val Asp Gln Gln Ser Gln Tyr Ile
    690                 695                 700
Gln Gly Tyr Lys Ile Leu Tyr Arg Pro Ser Gly Ala Asn His Gly Glu
705                 710                 715                 720
Ser Asp Trp Leu Val Phe Glu Val Arg Thr Pro Ala Lys Asn Ser Val
                725                 730                 735
Val Ile Pro Asp Leu Arg Lys Gly Val Asn Tyr Glu Ile Lys Ala Arg
            740                 745                 750
Pro Phe Phe Asn Glu Phe Gln Gly Ala Asp Ser Glu Ile Lys Phe Ala
        755                 760                 765
Lys Thr Leu Glu Glu Ala Pro Ser Ala Pro Gln Gly Val Thr Val
    770                 775                 780
Ser Lys Asn Asp Gly Asn Gly Thr Ala Ile Leu Val Ser Trp Gln Pro
785                 790                 795                 800
Pro Pro Glu Asp Thr Gln Asn Gly Met Val Gln Glu Tyr Lys Val Trp
                805                 810                 815
Cys Leu Gly Asn Glu Thr Arg Tyr His Ile Asn Lys Thr Val Asp Gly
```

```
              820                825                830
Ser Thr Phe Ser Val Ile Pro Phe Leu Val Pro Gly Ile Arg Tyr
            835                840                845
Ser Val Glu Val Ala Ala Ser Thr Gly Ala Gly Ser Gly Val Lys Ser
850                     855                860
Glu Pro Gln Phe Ile Gln Leu Asp Ala His Gly Asn Pro Val Ser Pro
865                     870                875                880
Glu Asp Gln Val Ser Leu Ala Gln Gln Ile Ser Asp Val Val Lys Gln
                  885                890                895
Pro Ala Phe Ile Ala Gly Ile Gly Ala Ala Cys Trp Ile Ile Leu Met
                900                905                910
Val Phe Ser Ile Trp Leu Tyr Arg His Arg Lys Lys Arg Asn Gly Leu
              915                920                925
Thr Ser Thr Tyr Ala Gly Ile Arg Lys Val Pro Ser Phe Thr Phe Thr
            930                935                940
Pro Thr Val Thr Tyr Gln Arg Gly Gly Glu Ala Val Ser Ser Gly Gly
945                     950                955                960
Arg Pro Gly Leu Leu Asn Ile Ser Glu Pro Ala Ala Gln Pro Trp Leu
                  965                970                975
Ala Asp Thr Trp Pro Asn Thr Gly Asn Asn His Asn Asp Cys Ser Ile
                980                985                990
Ser Cys Cys Thr Ala Gly Asn Gly  Asn Ser Asp Ser Asn  Leu Thr Thr
            995                1000                1005
Tyr Ser  Arg Pro Ala Asp Cys  Ile Ala Asn Tyr Asn  Asn Gln Leu
        1010                1015                1020
Asp Asn  Lys Gln Thr Asn Leu  Met Leu Pro Glu Ser  Thr Val Tyr
        1025                1030                1035
Gly Asp  Val Asp Leu Ser Asn  Lys Ile Asn Glu Met  Lys Thr Phe
        1040                1045                1050
Asn Ser  Pro Asn Leu Lys Asp  Gly Arg Phe Val Asn  Pro Ser Gly
        1055                1060                1065
Gln Pro  Thr Pro Tyr Ala Thr  Thr Gln Leu Ile Gln  Ser Asn Leu
        1070                1075                1080
Ser Asn  Asn Met Asn Asn Gly  Ser Gly Asp Ser Gly  Glu Lys His
        1085                1090                1095
Trp Lys  Pro Leu Gly Gln Gln  Lys Gln Glu Val Ala  Pro Val Gln
        1100                1105                1110
Tyr Asn  Ile Val Glu Gln Asn  Lys Leu Asn Lys Asp  Tyr Arg Ala
        1115                1120                1125
Asn Asp  Thr Val Pro Pro Thr  Ile Pro Tyr Asn Gln  Ser Tyr Asp
        1130                1135                1140
Gln Asn  Thr Gly Gly Ser Tyr  Asn Ser Ser Asp Arg  Gly Ser Ser
        1145                1150                1155
Thr Ser  Gly Ser Gln Gly His  Lys Lys Gly Ala Arg  Thr Pro Lys
        1160                1165                1170
Val Pro  Lys Gln Gly Gly Met  Asn Trp Ala Asp Leu  Leu Pro Pro
        1175                1180                1185
Pro Pro  Ala His Pro Pro His  Ser Asn Ser Glu Glu  Tyr Asn
        1190                1195                1200
Ile Ser  Val Asp Glu Ser Tyr  Asp Gln Glu Met Pro  Cys Pro Val
        1205                1210                1215
Pro Pro  Ala Arg Met Tyr Leu  Gln Gln Asp Glu Leu  Glu Glu Glu
        1220                1225                1230
```

-continued

```
Glu Asp Glu Arg Gly Pro Thr Pro Pro Val Arg Gly Ala Ala Ser
    1235                1240                1245

Ser Pro Ala Ala Val Ser Tyr Ser His Gln Ser Thr Ala Thr Leu
    1250                1255                1260

Thr Pro Ser Pro Gln Glu Glu Leu Gln Pro Met Leu Gln Asp Cys
    1265                1270                1275

Pro Glu Glu Thr Gly His Met Gln His Gln Pro Asp Arg Arg Arg
    1280                1285                1290

Gln Pro Val Ser Pro Pro Pro Pro Arg Pro Ile Ser Pro Pro
    1295                1300                1305

His Thr Tyr Gly Tyr Ile Ser Gly Pro Leu Val Ser Asp Met Asp
    1310                1315                1320

Thr Asp Ala Pro Glu Glu Glu Asp Glu Ala Asp Met Glu Val
    1325                1330                1335

Ala Lys Met Gln Thr Arg Arg Leu Leu Leu Arg Gly Leu Glu Gln
    1340                1345                1350

Thr Pro Ala Ser Ser Val Gly Asp Leu Glu Ser Ser Val Thr Gly
    1355                1360                1365

Ser Met Ile Asn Gly Trp Gly Ser Ala Ser Glu Glu Asp Asn Ile
    1370                1375                1380

Ser Ser Gly Arg Ser Ser Val Ser Ser Ser Asp Gly Ser Phe Phe
    1385                1390                1395

Thr Asp Ala Asp Phe Ala Gln Ala Val Ala Ala Ala Glu Tyr
    1400                1405                1410

Ala Gly Leu Lys Val Ala Arg Arg Gln Met Gln Asp Ala Ala Gly
    1415                1420                1425

Arg Arg His Phe His Ala Ser Gln Cys Pro Arg Pro Thr Ser Pro
    1430                1435                1440

Val Ser Thr Asp Ser Asn Met Ser Ala Ala Val Met Gln Lys Thr
    1445                1450                1455

Arg Pro Ala Lys Lys Leu Lys His Gln Pro Gly His Leu Arg Arg
    1460                1465                1470

Glu Thr Tyr Thr Asp Asp Leu Pro Pro Pro Val Pro Pro Pro
    1475                1480                1485

Ala Ile Lys Ser Pro Thr Ala Gln Ser Lys Thr Gln Leu Glu Val
    1490                1495                1500

Arg Pro Val Val Val Pro Lys Leu Pro Ser Met Asp Ala Arg Thr
    1505                1510                1515

Asp Arg Ser Ser Asp Arg Lys Gly Ser Ser Tyr Lys Gly Arg Glu
    1520                1525                1530

Val Leu Asp Gly Arg Gln Val Val Asp Met Arg Thr Asn Pro Gly
    1535                1540                1545

Asp Pro Arg Glu Ala Gln Glu Gln Gln Asn Asp Gly Lys Gly Arg
    1550                1555                1560

Gly Asn Lys Ala Ala Lys Arg Asp Leu Pro Pro Ala Lys Thr His
    1565                1570                1575

Leu Ile Gln Glu Asp Ile Leu Pro Tyr Cys Arg Pro Thr Phe Pro
    1580                1585                1590

Thr Ser Asn Asn Pro Arg Asp Pro Ser Ser Ser Ser Met Ser
    1595                1600                1605

Ser Arg Gly Ser Gly Ser Arg Gln Arg Glu Gln Ala Asn Val Gly
    1610                1615                1620
```

| | | | | |
|---|---|---|---|---|
| Arg | Arg | Asn Ile Ala Glu Met | Gln Val Leu Gly Gly | Tyr Glu Arg |
| | 1625 | 1630 | 1635 | |
| Gly Glu | Asp Asn Asn Glu Glu | Leu Glu Glu Thr Glu | Ser | |
| 1640 | | 1645 | 1650 | |

<210> SEQ ID NO 10
<211> LENGTH: 6629
<212> TYPE: DNA
<213> ORGANISM: homo sapiens

<400> SEQUENCE: 10

```
atgaaatgga aacatgttcc ttttttggtc atgatatcac tcctcagctt atccccaaat      60
cacctgtttc tggcccagct tattccagac cctgaagatg tagagagggg gaacgaccac     120
gggacgccaa tccccacctc tgataacgat gacaattcgc tgggctatac aggctcccgt     180
cttcgtcagg aagattttcc acctcgcatt gttgaacacc cttcagacct gattgtctca     240
aaaggagaac ctgcaacttt gaactgcaaa gctgaaggcc gccccacacc cactattgaa     300
tggtacaaag ggggagagag agtggagaca gacaaagatg accctcgctc acaccgaatg     360
ttgctgccga gtggatcttt attttttctta cgtatagtac atggacggaa agtagacct     420
gatgaaggag tctatgtctg tgtagcaagg aattaccttg agaggctgt gagccacaat     480
gcatcgctgg aagtagccat acttcgggat gacttcagac aaaacccttc ggatgtcatg     540
gttgcagtag agagcctgc agtaatgaa tgccaacctc cacgaggcca tcctgagccc     600
accatttcat ggaagaaaga tggctctcca ctggatgata aagatgaaag aataactata     660
cgaggaggaa agctcatgat cacttacacc cgtaaaagtg acgctggcaa atatgtttgt     720
gttggtacca atatggttgg ggaacgtgag agtgaagtag ccgagctgac tgtcttagag     780
agaccatcat ttgtgaagag acccagtaac ttggcagtaa ctgtggatga cagtgcagaa     840
tttaaatgtg aggcccgagg tgaccctgta cctacagtac gatggaggaa agatgatgga     900
gagctgccca atccagata tgaaatccga gatgatcata ccttgaaaat taggaaggtg     960
acagctggtg acatgggttc atacacttgt gttgcagaaa atatggtggg caaagctgaa    1020
gcatctgcta ctctgactgt tcaagaacct ccacattttg ttgtgaaacc ccgtgaccag    1080
gttgttgctt tgggacggac tgtaactttt cagtgtgaag caaccggaaa tcctcaacca    1140
gctatttctct ggaggagaga agggagtcag aatctacttt tctcatatca accaccacag    1200
tcatccagcc gattttcagt ctcccagact ggcgacctca caattactaa tgtccagcga    1260
tctgatgttg gttattacat ctgccagact ttaaatgttg ctggaagcat catcacaaag    1320
gcatatttgg aagttacaga tgtgattgca gatcggcctc ccccagttat tcgacaaggt    1380
cctgtgaatc agactgtagc cgtggatggc acttttcgtcc tcagctgtgt ggccacaggc    1440
agtccagtgc ccaccattct gtggagaaag gatggagtcc tcgtttcaac ccaagactct    1500
cgaatcaaac agttggagaa tggagtactg cagatccgat atgctaagct gggtgatact    1560
ggtcggtaca cctgcattgc atcaaccccc agtggtgaag caacatggag tgcttacatt    1620
gaagttcaag aatttggagt tccagttcag cctccaagac tactgaccc aaatttaatc    1680
cctagtgccc catcaaaacc tgaagtgaca gatgtcagca gaaatacagt cacattatcg    1740
tggcaaccaa atttgaattc aggagcaact ccaacatctt atattataga agccttcagc    1800
catgcatctg gtagcagctg gcagaccgta gcagagaatg tgaaaacaga acatctgcc    1860
attaaaggac tcaaacctaa tgcaatttac cttttccttg tgagggcagc taatgcatat    1920
ggaattagtg atccaagcca aatatcagat ccagtgaaaa cacaagatgt cctaccaaca    1980
```

```
agtcagggggg tggaccacaa gcaggtccag agagagctgg gaaatgctgt tctgcacctc   2040
cacaacccca ccgtcctttc ttcctcttcc atcgaagtgc actggacagt agatcaacag   2100
tctcagtata tacaaggata taaaattctc tatcggccat ctggagccaa ccacggagaa   2160
tcagactggt tagttttga agtgaggacg ccagccaaaa acagtgtggt aatccctgat   2220
ctcagaaagg gagtcaacta tgaaattaag gctcgcccct tttttaatga atttcaagga   2280
gcagatagtg aaatcaagtt tgccaaaacc ctggaagaag cacccagtgc cccacccaa    2340 ggtgtaactg tatccaagaa tgatggaaac ggaactgcaa ttctagttag ttggcagcca   2400
cctccagaag acactcaaaa tggaatggtc caagagtata aggtttggtg tctgggcaat   2460
gaaactcgat accacatcaa caaaacagtg gatggttcca cctttccgt ggtcattccc     2520 tttcttgttc ctggaatccg atacagtgtg gaagtggcag ccagcactgg ggctgggtct   2580
ggggtaaaga gtgagcctca gttcatccag ctggatgccc atggaaaccc tgtgtcacct   2640
gaggaccaag tcagcctcgc tcagcagatt tcagatgtgg tgaagcagcc ggccttcata   2700
gcaggtattg gagcagcctg ttggatcatc ctcatggtct tcagcatctg gctttatcga   2760
caccgcaaga gagaaacgg acttactagt acctacgcgg gtatcagaaa agtcccgtct   2820
tttaccttca caccaacagt aacttaccag agaggaggcg aagctgtcag cagtggaggg   2880
aggcctggac ttctcaacat cagtgaacct gccgcgcagc catggctggc agacacgtgg   2940
cctaatactg gcaacaacca caatgactgc tccatcagct gctgcacggc aggcaatgga   3000
aacagcgaca gcaacctcac tacctacagt cgcccagctg attgtatagc aaattataac   3060
aaccaactgg ataacaaaca aacaaatctg atgctccctg agtcaactgt ttatggtgat   3120
gtggacctta gtaacaaaat caatgagatg aaaaccttca atagcccaaa tctgaaggat   3180
gggcgttttg tcaatccatc agggcagcct actccttacg ccaccactca gctcatccag   3240
tcaaacctca gcaacaacat gaacaatggc agcggggact ctggcgagaa gcactggaaa   3300
ccactgggac agcagaaaca agaagtggca ccagttcagt acaacatcgt ggagcaaaac   3360
aagctgaaca agattatcg agcaaatgac acagttcctc caactatccc atacaaccaa   3420
tcatacgacc agaacacagg aggatcctac aacagctcag accggggcag tagtacatct   3480
gggagtcagg ggcacaagaa aggggcaaga cacccaagg taccaaaaca gggtggcatg   3540
aactgggcag acctgcttcc tcctccccca gcacatcctc ctccacacag caatagcgaa   3600
gagtacaaca tttctgtaga tgaaagctat gaccaagaaa tgccatgtcc cgtgccacca   3660
gcaaggatgt atttgcaaca agatgaatta agaggaggg aagatgaacg aggccccact   3720 cccctgttc ggggagcagc ttcttctcca gctgccgtgt cctatagcca tcagtccact    3780
gccactctga ctccctcccc acaggaagaa ctccagccca tgttacagga ttgtccagag   3840
gagactggcc acatgcagca ccagcccgac aggagacggc agcctgtgag tcctcctcca   3900
ccaccacggc cgatctcccc tccacatacc tatggctaca tttcaggacc cctggtctca   3960
gatatggata cggatgcgcc agaagaggaa gaagacgaag ccgacatgga ggtagccaag   4020
atgcaaacca gaaggctttt gttacgtggg cttgagcaga cacctgcctc cagtgttggg   4080
gacctggaga gctctgtcac ggggtccatg atcaacggct ggggctcagc ctcagaggag   4140
gacaacattt ccagcggacg ctccagtgtt agttcttcgg acggctcctt tttcactgat   4200
gctgactttg cccaggcagt cgcagcagcg gcagagtatg ctggtctgaa agtagcacga   4260
cggcaaatgc aggatgctgc tggccgtcga catttcatg cgtctcagtg ccctaggccc    4320
```

```
acaagtcccg tgtctacaga cagcaacatg agtgccgccg taatgcagaa aaccagacca    4380
gccaagaaac tgaaacacca gccaggacat ctgcgcagag aaacctacac agatgatctt    4440
ccaccacctc ctgtgccgcc acctgctata aagtcaccta ctgcccaatc aagacacag     4500 ctggaagtac gacctgtagt ggtgccaaaa ctcccttcta tggatgcaag aacagacaga    4560
tcatcagaca gaaaaggaag cagttacaag gggagagaag tgttggatgg aagacaggtt    4620
gttgacatgc gaacaaatcc aggtgatccc agagaagcac aggaacagca aaatgacggg    4680 aaggacgtg gaaacaaggc agcaaaacga gaccttccac cagcaaagac tcatctcatc      4740
caagaggata ttctacctta ttgtagacct acttttccaa catcaaataa tcccagagat    4800
cccagttcct caagctcaat gtcatcaaga ggatcaggaa gcagacaaag agaacaagca    4860
aatgtaggtc gaagaaatat tgcagaaatg caggtacttg gaggatatga agaggagaa     4920 gataataatg aagaattaga ggaaactgaa agctgaagac aaccaagagg cttatgagat    4980
ctaatgtgaa aatcatcact caagatgcct cctgtcagat gacacatgac gccagataaa    5040
atgttcagtg caatcagagt gtacaaattg tcgttttat tcctcttatt gggatatcat     5100
tttaaaaact ttattgggtt tttattgttg ttgtttgatc cctaaccta caaagagcct     5160 tcctattccc ctcgctgttg gagcaaacca ttataccta cttccagcaa gcaaagtgct    5220
ttgacttctt gcttcagtca tcagccagca agagggaaca aaactgttct tttgcatttt    5280
gccgctgaga tatggcattg cactgcttat atgccaagct aatttatagc aagatattga    5340
tcaaatatag aaagttgata ttcaacctca caagggctct caaagtataa tctttctata    5400
gccaactgct aatgcaaatt aaaacatatt tcattttaac atgatttcaa aatcagtttt    5460
tcatactacc ctttgctgga agaaactaaa aatatagcaa atgcagaacc acaaacaatt    5520
cgaatggggt agaaacattg taaatattta ctctttgcaa accctggtgg tattttattt    5580
tggcttcatt tcaatcattg aagtatattc ttattggaaa tgtacttttg gataagtagg    5640
gctaagccag ttggatctct ggttgtctag tcattgtcat aagtaaacct agtaaaacct    5700
tgttctattt ttcaatcatc aaaaagtaat tataaatacg tattacaaac aagtggatgt    5760
ttttaatgac caattgagta agaacatccc tgtcttaact ggcctaaatt tcttctggta    5820
gtgtcagttc aactttcaga agtgccactt aaggaagttt gattttttgtt tttgtaatgc    5880 actgttttta atctctctct ctttttttt ttttttttgg ttttaaaagc acaatcacta     5940
aactttattt gtaaaccatt gtaactatta acctttttg tcttattgaa aaaaaaatg      6000 ttgagaagcg tttttaacct gttttgttaa tgctctatgt ttgtatttgg aatatttgaa    6060
taatgacaga tggtgaagta acatgcatac tttattgtgg gccatgaacc aaatggttct    6120 tactttttcct ggacttaaag aaaaaaagag gtttaagttt gttgtggcca atgtcgaaac   6180
ctacaagatt tccttaaaat ctctaataga ggcattactt gctttcaatt gacaaatgat    6240
gccctctgac tagtagattt ctatgatcct ttttgtcat tttatgaata tcattgattt     6300
tataattggt gctatttgaa gaaaaaaatg tacatttatt catagataga taagtatcag    6360
gtctgacccc agtggaaaac aaagccaaac aaaactgaac cacaaaaaaa aaggctggtg    6420
ttcaccaaaa ccaaacttgt tcatttagat aatttgaaaa agttccatag aaaaggcgtg    6480
cagtactaag ggaacaatcc atgtgattaa tgttttcatt atgttcatgt aagaagcccc    6540
ttatttttag ccataatttt gcatactgaa aatccaataa tcagaaaagt aattttgtca    6600
cattatttat taaaaatgtt ctcaaatac                                       6629
```

<210> SEQ ID NO 11
<211> LENGTH: 1612
<212> TYPE: PRT
<213> ORGANISM: homo sapiens

<400> SEQUENCE: 11

| Met | Ile | Ala | Glu | Pro | Ala | His | Phe | Tyr | Leu | Phe | Gly | Leu | Ile | Cys | Leu |
|---|---|---|---|---|---|---|---|---|---|---|---|---|---|---|---|
| 1 | | | | 5 | | | | | 10 | | | | | 15 | |

| Cys | Ser | Gly | Ser | Arg | Leu | Arg | Gln | Glu | Asp | Phe | Pro | Pro | Arg | Ile | Val |
|---|---|---|---|---|---|---|---|---|---|---|---|---|---|---|---|
| | | | 20 | | | | | 25 | | | | | 30 | | |

| Glu | His | Pro | Ser | Asp | Leu | Ile | Val | Ser | Lys | Gly | Glu | Pro | Ala | Thr | Leu |
|---|---|---|---|---|---|---|---|---|---|---|---|---|---|---|---|
| | | 35 | | | | | 40 | | | | | 45 | | | |

| Asn | Cys | Lys | Ala | Glu | Gly | Arg | Pro | Thr | Pro | Thr | Ile | Glu | Trp | Tyr | Lys |
|---|---|---|---|---|---|---|---|---|---|---|---|---|---|---|---|
| 50 | | | | | 55 | | | | | 60 | | | | | |

| Gly | Gly | Glu | Arg | Val | Glu | Thr | Asp | Lys | Asp | Asp | Pro | Arg | Ser | His | Arg |
|---|---|---|---|---|---|---|---|---|---|---|---|---|---|---|---|
| 65 | | | | 70 | | | | | 75 | | | | | 80 | |

| Met | Leu | Leu | Pro | Ser | Gly | Ser | Leu | Phe | Phe | Leu | Arg | Ile | Val | His | Gly |
|---|---|---|---|---|---|---|---|---|---|---|---|---|---|---|---|
| | | | | 85 | | | | | 90 | | | | | 95 | |

| Arg | Lys | Ser | Arg | Pro | Asp | Glu | Gly | Val | Tyr | Val | Cys | Val | Ala | Arg | Asn |
|---|---|---|---|---|---|---|---|---|---|---|---|---|---|---|---|
| | | | 100 | | | | | 105 | | | | | 110 | | |

| Tyr | Leu | Gly | Glu | Ala | Val | Ser | His | Asn | Ala | Ser | Leu | Glu | Val | Ala | Ile |
|---|---|---|---|---|---|---|---|---|---|---|---|---|---|---|---|
| | | 115 | | | | | 120 | | | | | 125 | | | |

| Leu | Arg | Asp | Asp | Phe | Arg | Gln | Asn | Pro | Ser | Asp | Val | Met | Val | Ala | Val |
|---|---|---|---|---|---|---|---|---|---|---|---|---|---|---|---|
| | 130 | | | | | 135 | | | | | 140 | | | | |

| Gly | Glu | Pro | Ala | Val | Met | Glu | Cys | Gln | Pro | Pro | Arg | Gly | His | Pro | Glu |
|---|---|---|---|---|---|---|---|---|---|---|---|---|---|---|---|
| 145 | | | | | 150 | | | | | 155 | | | | | 160 |

| Pro | Thr | Ile | Ser | Trp | Lys | Lys | Asp | Gly | Ser | Pro | Leu | Asp | Asp | Lys | Asp |
|---|---|---|---|---|---|---|---|---|---|---|---|---|---|---|---|
| | | | 165 | | | | | 170 | | | | | 175 | | |

| Glu | Arg | Ile | Thr | Ile | Arg | Gly | Gly | Lys | Leu | Met | Ile | Thr | Tyr | Thr | Arg |
|---|---|---|---|---|---|---|---|---|---|---|---|---|---|---|---|
| | | | 180 | | | | | 185 | | | | | 190 | | |

| Lys | Ser | Asp | Ala | Gly | Lys | Tyr | Val | Cys | Val | Gly | Thr | Asn | Met | Val | Gly |
|---|---|---|---|---|---|---|---|---|---|---|---|---|---|---|---|
| | | | 195 | | | | | 200 | | | | | 205 | | |

| Glu | Arg | Glu | Ser | Glu | Val | Ala | Glu | Leu | Thr | Val | Leu | Glu | Arg | Pro | Ser |
|---|---|---|---|---|---|---|---|---|---|---|---|---|---|---|---|
| | 210 | | | | | 215 | | | | | 220 | | | | |

| Phe | Val | Lys | Arg | Pro | Ser | Asn | Leu | Ala | Val | Thr | Val | Asp | Ser | Ala |
|---|---|---|---|---|---|---|---|---|---|---|---|---|---|---|
| 225 | | | | | 230 | | | | | 235 | | | | | 240 |

| Glu | Phe | Lys | Cys | Glu | Ala | Arg | Gly | Asp | Pro | Val | Pro | Thr | Val | Arg | Trp |
|---|---|---|---|---|---|---|---|---|---|---|---|---|---|---|---|
| | | | | 245 | | | | | 250 | | | | | 255 | |

| Arg | Lys | Asp | Asp | Gly | Glu | Leu | Pro | Lys | Ser | Arg | Tyr | Glu | Ile | Arg | Asp |
|---|---|---|---|---|---|---|---|---|---|---|---|---|---|---|---|
| | | | 260 | | | | | 265 | | | | | 270 | | |

| Asp | His | Thr | Leu | Lys | Ile | Arg | Lys | Val | Thr | Ala | Gly | Asp | Met | Gly | Ser |
|---|---|---|---|---|---|---|---|---|---|---|---|---|---|---|---|
| | | 275 | | | | | 280 | | | | | 285 | | | |

| Tyr | Thr | Cys | Val | Ala | Glu | Asn | Met | Val | Gly | Lys | Ala | Glu | Ala | Ser | Ala |
|---|---|---|---|---|---|---|---|---|---|---|---|---|---|---|---|
| | 290 | | | | | 295 | | | | | 300 | | | | |

| Thr | Leu | Thr | Val | Gln | Glu | Pro | Pro | His | Phe | Val | Val | Lys | Pro | Arg | Asp |
|---|---|---|---|---|---|---|---|---|---|---|---|---|---|---|---|
| 305 | | | | | 310 | | | | | 315 | | | | | 320 |

| Gln | Val | Val | Ala | Leu | Gly | Arg | Thr | Val | Thr | Phe | Gln | Cys | Glu | Ala | Thr |
|---|---|---|---|---|---|---|---|---|---|---|---|---|---|---|---|
| | | | | 325 | | | | | 330 | | | | | 335 | |

| Gly | Asn | Pro | Gln | Pro | Ala | Ile | Phe | Trp | Arg | Arg | Glu | Gly | Ser | Gln | Asn |
|---|---|---|---|---|---|---|---|---|---|---|---|---|---|---|---|
| | | | 340 | | | | | 345 | | | | | 350 | | |

| Leu | Leu | Phe | Ser | Tyr | Gln | Pro | Pro | Gln | Ser | Ser | Arg | Phe | Ser | Val |
|---|---|---|---|---|---|---|---|---|---|---|---|---|---|---|
| | | | 355 | | | | | 360 | | | | | 365 | | |

| Ser | Gln | Thr | Gly | Asp | Leu | Thr | Ile | Thr | Asn | Val | Gln | Arg | Ser | Asp | Val |
|---|---|---|---|---|---|---|---|---|---|---|---|---|---|---|---|
| | 370 | | | | | 375 | | | | | 380 | | | | |

```
Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
                405                 410                 415

Val Ile Arg Gln Gly Pro Val Asn Gln Thr Val Ala Val Asp Gly Thr
            420                 425                 430

Phe Val Leu Ser Cys Val Ala Thr Gly Ser Pro Val Pro Thr Ile Leu
            435                 440                 445

Trp Arg Lys Asp Gly Val Leu Val Ser Thr Gln Asp Ser Arg Ile Lys
450                 455                 460

Gln Leu Glu Asn Gly Val Leu Gln Ile Arg Tyr Ala Lys Leu Gly Asp
465                 470                 475                 480

Thr Gly Arg Tyr Thr Cys Ile Ala Ser Thr Pro Ser Gly Glu Ala Thr
                485                 490                 495

Trp Ser Ala Tyr Ile Glu Val Gln Glu Phe Gly Val Pro Val Gln Pro
                500                 505                 510

Pro Arg Pro Thr Asp Pro Asn Leu Ile Pro Ser Ala Pro Ser Lys Pro
            515                 520                 525

Glu Val Thr Asp Val Ser Arg Asn Thr Val Thr Leu Ser Trp Gln Pro
530                 535                 540

Asn Leu Asn Ser Gly Ala Thr Pro Thr Ser Tyr Ile Ile Glu Ala Phe
545                 550                 555                 560

Ser His Ala Ser Gly Ser Ser Trp Gln Thr Val Ala Glu Asn Val Lys
                565                 570                 575

Thr Glu Thr Ser Ala Ile Lys Gly Leu Lys Pro Asn Ala Ile Tyr Leu
                580                 585                 590

Phe Leu Val Arg Ala Ala Asn Ala Tyr Gly Ile Ser Asp Pro Ser Gln
            595                 600                 605

Ile Ser Asp Pro Val Lys Thr Gln Asp Val Leu Pro Thr Ser Gln Gly
            610                 615                 620

Val Asp His Lys Gln Val Gln Arg Glu Leu Gly Asn Ala Val Leu His
625                 630                 635                 640

Leu His Asn Pro Thr Val Leu Ser Ser Ser Ile Glu Val His Trp
                645                 650                 655

Thr Val Asp Gln Gln Ser Gln Tyr Ile Gln Gly Tyr Lys Ile Leu Tyr
                660                 665                 670

Arg Pro Ser Gly Ala Asn His Gly Glu Ser Asp Trp Leu Val Phe Glu
            675                 680                 685

Val Arg Thr Pro Ala Lys Asn Ser Val Val Ile Pro Asp Leu Arg Lys
690                 695                 700

Gly Val Asn Tyr Glu Ile Lys Ala Arg Pro Phe Phe Asn Glu Phe Gln
705                 710                 715                 720

Gly Ala Asp Ser Glu Ile Lys Phe Ala Lys Thr Leu Glu Glu Ala Pro
            725                 730                 735

Ser Ala Pro Pro Gln Gly Val Thr Val Ser Lys Asn Asp Gly Asn Gly
            740                 745                 750

Thr Ala Ile Leu Val Ser Trp Gln Pro Pro Glu Asp Thr Gln Asn
            755                 760                 765

Gly Met Val Gln Glu Tyr Lys Val Trp Cys Leu Gly Asn Glu Thr Arg
            770                 775                 780

Tyr His Ile Asn Lys Thr Val Asp Gly Ser Thr Phe Ser Val Val Ile
785                 790                 795                 800

Pro Phe Leu Val Pro Gly Ile Arg Tyr Ser Val Glu Val Ala Ala Ser
```

```
                        805                 810                 815
Thr Gly Ala Gly Ser Gly Val Lys Ser Glu Pro Gln Phe Ile Gln Leu
                820                 825                 830

Asp Ala His Gly Asn Pro Val Ser Pro Glu Asp Gln Val Ser Leu Ala
            835                 840                 845

Gln Gln Ile Ser Asp Val Val Lys Gln Pro Ala Phe Ile Ala Gly Ile
        850                 855                 860

Gly Ala Ala Cys Trp Ile Ile Leu Met Val Phe Ser Ile Trp Leu Tyr
865                 870                 875                 880

Arg His Arg Lys Lys Arg Asn Gly Leu Thr Ser Thr Tyr Ala Gly Ile
                885                 890                 895

Arg Lys Val Pro Ser Phe Thr Phe Thr Pro Thr Val Thr Tyr Gln Arg
            900                 905                 910

Gly Gly Glu Ala Val Ser Ser Gly Gly Arg Pro Gly Leu Leu Asn Ile
        915                 920                 925

Ser Glu Pro Ala Ala Gln Pro Trp Leu Ala Asp Thr Trp Pro Asn Thr
930                 935                 940

Gly Asn Asn His Asn Asp Cys Ser Ile Ser Cys Cys Thr Ala Gly Asn
945                 950                 955                 960

Gly Asn Ser Asp Ser Asn Leu Thr Thr Tyr Ser Arg Pro Ala Asp Cys
                965                 970                 975

Ile Ala Asn Tyr Asn Asn Gln Leu Asp Asn Lys Gln Thr Asn Leu Met
            980                 985                 990

Leu Pro Glu Ser Thr Val Tyr Gly Asp Val Asp Leu Ser Asn Lys Ile
        995                 1000                1005

Asn Glu Met Lys Thr Phe Asn Ser Pro Asn Leu Lys Asp Gly Arg
    1010                1015                1020

Phe Val Asn Pro Ser Gly Gln Pro Thr Pro Tyr Ala Thr Thr Gln
    1025                1030                1035

Leu Ile Gln Ser Asn Leu Ser Asn Asn Met Asn Asn Gly Ser Gly
    1040                1045                1050

Asp Ser Gly Glu Lys His Trp Lys Pro Leu Gly Gln Gln Lys Gln
    1055                1060                1065

Glu Val Ala Pro Val Gln Tyr Asn Ile Val Glu Gln Asn Lys Leu
    1070                1075                1080

Asn Lys Asp Tyr Arg Ala Asn Asp Thr Val Pro Pro Thr Ile Pro
    1085                1090                1095

Tyr Asn Gln Ser Tyr Asp Gln Asn Thr Gly Gly Ser Tyr Asn Ser
    1100                1105                1110

Ser Asp Arg Gly Ser Ser Thr Ser Gly Ser Gln Gly His Lys Lys
    1115                1120                1125

Gly Ala Arg Thr Pro Lys Val Pro Lys Gln Gly Gly Met Asn Trp
    1130                1135                1140

Ala Asp Leu Leu Pro Pro Pro Ala His Pro Pro His Ser
    1145                1150                1155

Asn Ser Glu Glu Tyr Asn Ile Ser Val Asp Glu Ser Tyr Asp Gln
    1160                1165                1170

Glu Met Pro Cys Pro Val Pro Ala Arg Met Tyr Leu Gln Gln
    1175                1180                1185

Asp Glu Leu Glu Glu Glu Glu Asp Glu Arg Gly Pro Thr Pro Pro
    1190                1195                1200

Val Arg Gly Ala Ala Ser Ser Pro Ala Ala Val Ser Tyr Ser His
    1205                1210                1215
```

```
Gln Ser Thr Ala Thr Leu Thr Pro Ser Pro Gln Glu Glu Leu Gln
1220                1225                1230

Pro Met Leu Gln Asp Cys Pro Glu Glu Thr Gly His Met Gln His
1235                1240                1245

Gln Pro Asp Arg Arg Gln Pro Val Ser Pro Pro Pro Pro
1250                1255                1260

Arg Pro Ile Ser Pro Pro His Thr Tyr Gly Tyr Ile Ser Gly Pro
1265                1270                1275

Leu Val Ser Asp Met Asp Thr Asp Ala Pro Glu Glu Glu Glu Asp
1280                1285                1290

Glu Ala Asp Met Glu Val Ala Lys Met Gln Thr Arg Arg Leu Leu
1295                1300                1305

Leu Arg Gly Leu Glu Gln Thr Pro Ala Ser Ser Val Gly Asp Leu
1310                1315                1320

Glu Ser Ser Val Thr Gly Ser Met Ile Asn Gly Trp Gly Ser Ala
1325                1330                1335

Ser Glu Glu Asp Asn Ile Ser Ser Gly Arg Ser Ser Val Ser Ser
1340                1345                1350

Ser Asp Gly Ser Phe Phe Thr Asp Ala Asp Phe Ala Gln Ala Val
1355                1360                1365

Ala Ala Ala Ala Glu Tyr Ala Gly Leu Lys Val Ala Arg Arg Gln
1370                1375                1380

Met Gln Asp Ala Ala Gly Arg Arg His Phe His Ala Ser Gln Cys
1385                1390                1395

Pro Arg Pro Thr Ser Pro Val Ser Thr Asp Ser Asn Met Ser Ala
1400                1405                1410

Ala Val Met Gln Lys Thr Arg Pro Ala Lys Lys Leu Lys His Gln
1415                1420                1425

Pro Gly His Leu Arg Arg Glu Thr Tyr Thr Asp Asp Leu Pro Pro
1430                1435                1440

Pro Pro Val Pro Pro Ala Ile Lys Ser Pro Thr Ala Gln Ser
1445                1450                1455

Lys Thr Gln Leu Glu Val Arg Pro Val Val Val Pro Lys Leu Pro
1460                1465                1470

Ser Met Asp Ala Arg Thr Asp Arg Ser Ser Asp Arg Lys Gly Ser
1475                1480                1485

Ser Tyr Lys Gly Arg Glu Val Leu Asp Gly Arg Gln Val Val Asp
1490                1495                1500

Met Arg Thr Asn Pro Gly Asp Pro Arg Glu Ala Gln Glu Gln Gln
1505                1510                1515

Asn Asp Gly Lys Gly Arg Gly Asn Lys Ala Ala Lys Arg Asp Leu
1520                1525                1530

Pro Pro Ala Lys Thr His Leu Ile Gln Glu Asp Ile Leu Pro Tyr
1535                1540                1545

Cys Arg Pro Thr Phe Pro Thr Ser Asn Asn Pro Arg Asp Pro Ser
1550                1555                1560

Ser Ser Ser Ser Met Ser Ser Arg Gly Ser Gly Ser Arg Gln Arg
1565                1570                1575

Glu Gln Ala Asn Val Gly Arg Arg Asn Ile Ala Glu Met Gln Val
1580                1585                1590

Leu Gly Gly Tyr Glu Arg Gly Glu Asp Asn Asn Glu Glu Leu Glu
1595                1600                1605
```

Glu Thr   Glu Ser
    1610

<210> SEQ ID NO 12
<211> LENGTH: 7475
<212> TYPE: DNA
<213> ORGANISM: homo sapiens

<400> SEQUENCE: 12

| | | | | | |
|---|---|---|---|---|---|
| acttcagacg | ccgctgatcc | gggaggagct | ggggtgagcc | gcggcggccg | tctctcccac | 60 |
| ccgcagcagc | atcctctctg | cccttctctg | ccaccccggg | gagagccggg | agctgcctct | 120 |
| ttacagcttc | cacgagccag | gggtgcaggc | agctgccccc | aggaagtttg | gcttctgcg | 180 |
| tagtttaggg | gtgcctgcga | gcgcccaga | gggcgagggg | ccgagggcga | tgttgggcgc | 240 |
| cgcgcggggc | tggggcgcc | cagaagacgt | gcgagtgtcc | gcggtcctgc | tgctgtctcc | 300 |
| agtaccctcc | gcatccccca | agtgatggga | acaagggccc | gcccaggcag | ccgctgtcgc | 360 |
| cgcaccgccc | cctcgctcgc | tctctgcgcg | cggagtcacc | cagtcacact | cccggcaccc | 420 |
| cgagcccttc | ctccggagct | gctgcttcta | ctttggctgc | tatcgccgcc | gccgcgggtg | 480 |
| gcccgctgct | gactgggctc | gccgggagac | ggagaagcac | ttttttggccc | tccctcagca | 540 |
| gctctcacac | cccaactttg | ccgccgccgc | cgcgcctgcc | ctcgcagcgg | cgctcggccg | 600 |
| cacattgtgg | gggcgcacgc | cgggaggctc | cgcaagaccg | tggaggcagg | aaacggcact | 660 |
| actgcgcttc | tgcctcggct | cttttgttgtt | cgctttggat | ggttcttgaa | agtgtctgag | 720 |
| cctcctcgga | aatcctgggg | ccggagaaga | caaaccttgg | aattcttcct | ctgcaaaagt | 780 |
| ctctgagata | ctgacaagcg | tccggaaagg | tcgacgagta | attgccctga | aaactcttgg | 840 |
| ctaattgacc | cacgttgctt | atattaagcc | tttgtgtgtg | gtgtgtggct | tcatacattt | 900 |
| ggggacccta | tttccactcc | ctcctcttgg | catgagactg | tatacaggat | ccacccgagg | 960 |
| acaatgattg | cggagcccgc | tcacttttac | ctgtttggat | taatatgtct | ctgttcaggc | 1020 |
| tcccgtcttc | gtcaggaaga | ttttccacct | cgcattgttg | aacacccttc | agacctgatt | 1080 |
| gtctcaaaag | gagaacctgc | aactttgaac | tgcaaagctg | aaggccgccc | cacacccact | 1140 |
| attgaatggt | acaagggggg | agagagagtg | gagacagaca | aagatgaccc | tcgctcacac | 1200 |
| cgaatgttgc | tgccgagtgg | atcttttattt | ttcttacgta | tagtacatgg | acggaaaagt | 1260 |
| agacctgatg | aaggagtcta | tgtctgtgta | gcaaggaatt | accttggaga | ggctgtgagc | 1320 |
| cacaatgcat | cgctggaagt | agccatactt | cgggatgact | tcagacaaaa | cccttcggat | 1380 |
| gtcatggttg | cagtaggaga | gcctgcagta | atggaatgcc | aacctccacg | aggccatcct | 1440 |
| gagcccacca | tttcatggaa | gaaagatggc | tctccactgg | atgataaaga | tgaaagaata | 1500 |
| actatacgag | gaggaaagct | catgatcact | tacacccgta | aaagtgacgc | tggcaaatat | 1560 |
| gtttgtgttg | gtaccaatat | ggttgggaa | cgtgagagtg | aagtagccga | gctgactgtc | 1620 |
| ttagagagac | catcatttgt | gaagagaccc | agtaacttgg | cagtaactgt | ggatgacagt | 1680 |
| gcagaattta | atgtgaggc | ccgaggtgac | cctgtaccta | cagtacgatg | gaggaaagat | 1740 |
| gatggagagc | tgcccaaatc | cagatatgaa | atccgagatg | atcataccttt | gaaaattagg | 1800 |
| aaggtgacag | ctggtgacat | gggttcatac | acttgtgttg | cagaaaatat | ggtgggcaaa | 1860 |
| gctgaagcat | ctgctactct | gactgttcaa | gaacctccac | attttgttgt | gaaacccgt | 1920 |
| gaccaggttt | tgctttggg | acggactgta | acttttcagt | gtgaagcaac | cggaaatcct | 1980 |
| caaccagcta | ttttctggag | gagagaaggg | agtcagaatc | tactttttctc | atatcaacca | 2040 |

```
ccacagtcat ccagccgatt ttcagtctcc cagactggcg acctcacaat tactaatgtc    2100
cagcgatctg atgttggtta ttacatctgc cagactttaa atgttgctgg aagcatcatc    2160
acaaaggcat atttggaagt tacagatgtg attgcagatc ggcctccccc agttattcga    2220
caaggtcctg tgaatcagac tgtagccgtg atggcacttt cgtcctcag ctgtgtggcc     2280 acaggcagtc cagtgcccac cattctgtgg agaaaggatg gagtcctcgt ttcaacccaa    2340
gactctcgaa tcaaacagtt ggagaatgga gtactgcaga tccgatatgc taagctgggt    2400
gatactggtc ggtacacctg cattgcatca accccagtg gtgaagcaac atggagtgct     2460
tacattgaag ttcaagaatt tggagttcca gttcagcctc caagacctac tgacccaaat    2520
ttaatcccta gtgccccatc aaaacctgaa gtgacagatg tcagcagaaa tacagtcaca    2580
ttatcgtggc aaccaaattt gaattcagga gcaactccaa catcttatat tatagaagcc    2640
ttcagccatg catctggtag cagctggcag accgtagcag agaatgtgaa aacagaaaca    2700
tctgccatta aaggactcaa acctaatgca atttaccttt tccttgtgag ggcagctaat    2760
gcatatggaa ttagtgatcc aagccaaata tcagatccag tgaaaacaca agatgtccta    2820
ccaacaagtc agggggtgga ccacaagcag gtccagagag agctgggaaa tgctgttctg    2880
cacctccaca accccaccgt cctttcttcc tcttccatcg aagtgcactg acagtagat     2940 caacagtctc agtatataca aggatataaa attctctatc ggccatctgg agccaaccac    3000
ggagaatcag actggttagt ttttgaagtg aggacgccag ccaaaaacag tgtggtaatc    3060
cctgatctca gaaagggagt caactatgaa attaaggctc gccctttttt taatgaattt    3120
caaggagcag atagtgaaat caagtttgcc aaaaccctgg aagaagcacc cagtgcccca    3180
ccccaaggtg taactgtatc caagaatgat ggaaacggaa ctgcaattct agttagttgg    3240
cagccacctc cagaagacac tcaaaatgga atggtccaag agtataaggt ttggtgtctg    3300
ggcaatgaaa ctcgatacca catcaacaaa acagtggatg gttccacctt tccgtggtc    3360 attccctttc ttgttcctgg aatccgatac agtgtgaag tggcagccag cactggggct     3420
gggtctgggg taaagagtga gcctcagttc atccagctgg atgcccatgg aaaccctgtg    3480
tcacctgagg accaagtcag cctcgctcag cagatttcag atgtggtgaa gcagccggcc    3540
ttcatagcag gtattggagc agcctgttgg atcatcctca tggtcttcag catctggctt    3600
tatcgacacc gcaagaagag aaacggactt actagtacct acgcgggtat cagaaaagtc    3660
ccgtctttta ccttcacacc aacagtaact taccagagag gaggcgaagc tgtcagcagt    3720
ggagggaggc ctggacttct caacatcagt gaacctgccg cgcagccatg gctggcagac    3780
acgtggccta atactggcaa caaccacaat gactgctcca tcagctgctg cacggcaggc    3840
aatggaaaca cgcgacagca acctcactac tacagtcgcc cagctgattg tatagcaaat    3900
tataacaacc aactggataa caaacaaaca aatctgatgc tccctgagtc aactgtttat    3960
ggtgatgtgg accttagtaa caaaatcaat gagatgaaaa ccttcaatag cccaaatctg    4020
aaggatgggc gttttgtcaa tccatcaggg cagcctactc cttacgccac cactcagctc    4080
atccagtcaa acctcagcaa caacatgaac aatggcagcg gggactctgg cgagaagcac    4140
tggaaaccac tggacagca gaaacaagaa gtggcaccag ttcagtacaa catcgtggag    4200
caaaacaagc tgaacaaaga ttatcgagca aatgacacag ttcctccaac tatcccatac    4260
aaccaatcat cgaccagaa cacaggagga tcctacaaca gctcagaccg gggcagtagt    4320
acatctggga gtcaggggca caagaaaggg gcaagaacca ccaaggtacc aaaacagggt    4380
ggcatgaact gggcagacct gcttcctcct cccccagcac atcctcctcc acacagcaat    4440
```

```
agcgaagagt acaacatttc tgtagatgaa agctatgacc aagaaatgcc atgtcccgtg    4500
ccaccagcaa ggatgtattt gcaacaagat gaattagaag aggaggaaga tgaacgaggc    4560
cccactcccc ctgttcgggg agcagcttct tctccagctg ccgtgtccta tagccatcag    4620
tccactgcca ctctgactcc ctccccacag gaagaactcc agcccatgtt acaggattgt    4680
ccagaggaga ctggccacat gcagcaccag cccgacagga gacggcagcc tgtgagtcct    4740
cctccaccac cacggccgat ctcccctcca catacctatg gctacatttc aggacccctg    4800
gtctcagata tggatacgga tgcgccagaa gaggaagaag acgaagccga catggaggta    4860
gccaagatgc aaaccagaag gcttttgtta cgtgggcttg agcagacacc tgcctccagt    4920
gttggggacc tggagagctc tgtcacgggg tccatgatca acggctgggg ctcagcctca    4980
gaggaggaca acatttccag cggacgctcc agtgttagtt cttcggacgg ctccttttc     5040 actgatgctg actttgccca ggcagtcgca gcagcggcag agtatgctgg tctgaaagta    5100
gcacgacggc aaatgcagga tgctgctggc cgtcgacatt ttcatgcgtc tcagtgccct    5160
aggcccacaa gtcccgtgtc tacagacagc aacatgagtg ccgccgtaat gcagaaaacc    5220
agaccagcca agaaactgaa acaccagcca ggacatctgc gcagagaaac ctacacagat    5280
gatcttccac cacctcctgt gccgccacct gctataaagt cacctactgc ccaatccaag    5340
acacagctgg aagtacgacc tgtagtggtg ccaaaactcc cttctatgga tgcaagaaca    5400
gacagatcat cagacagaaa aggaagcagt tacaagggga gagaagtgtt ggatggaaga    5460
caggttgttg acatgcgaac aaatccaggt gatcccagag aagcacagga acagcaaaat    5520
gacgggaaag gacgtggaaa caaggcagca aaacgagacc ttccaccagc aaagactcat    5580
ctcatccaag aggatattct accttattgt agacctactt ttccaacatc aaataatccc    5640
agagatccca gttcctcaag ctcaatgtca tcaagaggat caggaagcag acaaagagaa    5700
caagcaaatg taggtcgaag aaatattgca gaaatgcagg tacttggagg atatgaaaga    5760
ggagaagata taatgaaga attagaggaa actgaaagct gaagcaacc aagaggctta      5820 tgagatctaa tgtgaaaatc atcactcaag atgcctcctg tcagatgaca catgacgcca    5880
gataaaatgt tcagtgcaat cagagtgtac aaattgtcgt tttattcct cttattggga     5940 tatcatttta aaaactttat tgggttttta ttgttgttgt ttgatcccta accctacaaa    6000
gagccttcct attcccctcg ctgttggagc aaaccattat accttacttc cagcaagcaa    6060
agtgctttga cttcttgctt cagtcatcag ccagcaagag ggaacaaaac tgttcttttg    6120
cattttgccg ctgagatatg gcattgcact gcttatatgc caagctaatt tatagcaaga    6180
tattgatcaa atatagaaag ttgatattca acctcacaag ggctctcaaa gtataatctt    6240
tctatagcca actgctaatg caaattaaaa catatttcat tttaacatga tttcaaaatc    6300 agttttcat actacccttt gctggaagaa actaaaaata tagcaaatgc agaaccacaa      6360
acaattcgaa tggggtagaa acattgtaaa tatttactct ttgcaaaccc tggtggtatt    6420
ttattttggc ttcatttcaa tcattgaagt atattcttat tggaaatgta cttttggata    6480
agtagggcta agccagttgg atctctggtt gtctagtcat tgtcataagt aaacctagta    6540
aaaccttgtt ctatttttca atcatcaaaa agtaattata aatacgtatt acaaacaagt    6600
ggatgttttt aatgaccaat tgagtaagaa catccctgtc ttaactggcc taaatttctt    6660
```

```
ctggtagtgt cagttcaact ttcagaagtg ccacttaagg aagtttgatt tttgttttg     6720 taatgcactg tttttaatct ctctctcttt tttttttttt ttttggtttt aaaagcacaa     6780
tcactaaact ttatttgtaa accattgtaa ctattaacct tttttgtctt attgaaaaaa     6840
aaaatgttga aagcgtttt taacctgttt tgttaatgct ctatgtttgt atttggaata     6900
tttgaataat gacagatggt gaagtaacat gcatacttta ttgtgggcca tgaaccaaat     6960
ggttcttact tttcctggac ttaaagaaaa aagaggttt aagtttgttg tggccaatgt     7020
cgaaacctac aagatttcct taaaatctct aatagaggca ttacttgctt tcaattgaca     7080
aatgatgccc tctgactagt agatttctat gatcctttt tgtcatttta tgaatatcat     7140
tgattttata attggtgcta tttgaagaaa aaatgtaca tttattcata gatagataag     7200
tatcaggtct gaccccagtg gaaaacaaag ccaaacaaaa ctgaaccaca aaaaaaagg     7260 ctggtgttca ccaaaaccaa acttgttcat ttagataatt tgaaaagtt ccatagaaaa     7320 ggcgtgcagt actaagggaa caatccatgt gattaatgtt ttcattatgt tcatgtaaga     7380
agccccttat ttttagccat aattttgcat actgaaaatc caataatcag aaaagtaatt     7440
ttgtcacatt atttattaaa aatgttctca aatac                                7475
```

```
<210> SEQ ID NO 13
<211> LENGTH: 24
<212> TYPE: DNA
<213> ORGANISM: Artificial Sequence
<220> FEATURE:
<223> OTHER INFORMATION: PCR primer

<400> SEQUENCE: 13
accatgattg cggagcccgc tcac                                              24

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
ggccggctgc ttcaccacat                                                   20

<210> SEQ ID NO 15
<211> LENGTH: 30
<212> TYPE: DNA
<213> ORGANISM: Artificial Sequence
<220> FEATURE:
<223> OTHER INFORMATION: PCR primer

<400> SEQUENCE: 15
ggtacccgca cccagtgccc caccccaagg                                        30

<210> SEQ ID NO 16
<211> LENGTH: 30
<212> TYPE: DNA
<213> ORGANISM: Artificial Sequence
<220> FEATURE:
<223> OTHER INFORMATION: PCR primer

<400> SEQUENCE: 16
ggtaccgcat ctgaaatctg ctgagcgagg                                        30
```